(12) United States Patent
Makarov et al.

(10) Patent No.: US 12,104,194 B2
(45) Date of Patent: *Oct. 1, 2024

(54) METHODS AND COMPOSITIONS FOR SIZE-CONTROLLED HOMOPOLYMER TAILING OF SUBSTRATE POLYNUCLEOTIDES BY A NUCLEIC ACID POLYMERASE

(71) Applicant: Integrated DNA Technologies, Inc., Coralville, IA (US)

(72) Inventors: Vladimir Makarov, Ann Arbor, MI (US); Laurie Kurihara, Ann Arbor, MI (US)

(73) Assignee: Integrated DNA Technologies, Inc., Coralville, IA (US)

( * ) Notice: Subject to any disclaimer, the term of this patent is extended or adjusted under 35 U.S.C. 154(b) by 452 days.

This patent is subject to a terminal disclaimer.

(21) Appl. No.: 17/398,967

(22) Filed: Aug. 10, 2021

(65) Prior Publication Data

US 2022/0186273 A1 Jun. 16, 2022

Related U.S. Application Data

(60) Continuation of application No. 16/906,165, filed on Jun. 19, 2020, now Pat. No. 11,118,207, which is a continuation of application No. 15/898,460, filed on Feb. 17, 2018, now Pat. No. 10,731,194, which is a division of application No. 14/384,113, filed as application No. PCT/US2013/031104 on Mar. 13, 2013, now Pat. No. 9,896,709.

(60) Provisional application No. 61/613,784, filed on Mar. 21, 2012, provisional application No. 61/610,296, filed on Mar. 13, 2012.

(51) Int. Cl.
| | |
|---|---|
| *C12Q 1/6855* | (2018.01) |
| *C12N 9/12* | (2006.01) |
| *C12P 19/34* | (2006.01) |
| *C12Q 1/6806* | (2018.01) |
| *C12Q 1/6869* | (2018.01) |

(52) U.S. Cl.
CPC ............ *C12P 19/34* (2013.01); *C12N 9/1241* (2013.01); *C12Q 1/6806* (2013.01); *C12Q 1/6855* (2013.01); *C12Q 1/6869* (2013.01); *C12Q 2521/131* (2013.01); *C12Q 2525/121* (2013.01); *C12Q 2525/173* (2013.01); *C12Q 2525/186* (2013.01); *C12Q 2525/191* (2013.01); *C12Q 2525/204* (2013.01)

(58) Field of Classification Search
CPC ..... C12P 19/34; C12Q 1/6806; C12Q 1/6855; C12Q 2521/131; C12Q 2525/121; C12Q 2525/173; C12Q 2525/186; C12Q 2525/191; C12Q 2525/204; C12Q 2537/163

See application file for complete search history.

(56) References Cited

U.S. PATENT DOCUMENTS

| | | | | |
|---|---|---|---|---|
| 5,334,515 A | * | 8/1994 | Rashtchian | C12Q 1/6865 435/91.51 |
| 6,406,890 B1 | * | 6/2002 | Mueller | C12N 9/1264 435/5 |
| 9,896,709 B2 | * | 2/2018 | Makarov | C12P 19/34 |

FOREIGN PATENT DOCUMENTS

WO WO-2010060132 A1 * 6/2010 ............. C12N 15/66

OTHER PUBLICATIONS

Higgins, N.P. & Cozzarelli, N.R. DNA-Joining Enzymes: A Review. Methods in Enzymology 1979; 68: 50-71 (Year: 1979).*

* cited by examiner

*Primary Examiner* — Angela M. Bertagna
(74) *Attorney, Agent, or Firm* — Barnes & Thornburg LLP

(57) ABSTRACT

The present invention is directed to methods and compositions for adding tails of specific lengths to a substrate polynucleotide. The invention also contemplates methods and compositions for immobilization of tailed substrates to a solid support. The disclosure contemplates that the attenuator molecule is any biomolecule that associates with a tail sequence added to a substrate polynucleotide and controls the addition of a tail sequence to the 3' end of the substrate polynucleotide. The sequence that is added to the substrate polynucleotide is referred to herein as a tail sequence, or simply a tail, and the process of adding a nucleotide to a substrate polynucleotide is referred to herein as tailing.

13 Claims, 43 Drawing Sheets

Specification includes a Sequence Listing.

DNA primer

5' ——▶ 3'    3'P-dT dT dT dU dT dT dT dT dU dT dT dT dT dU dT dT dT dT dU-5'

Attenuator Poly (dT₄dU)₆

⇩ Incubation with TdT enzyme and dATP in the presence of attenuator molecule (poly (dT₄dU)₆

Tailed DNA primer – Attenuator Poly(dT₄dU)₆ complex

5'————dA dA dA dA dA dA dA dA dA dA dA dA dA-3'
              | | | | | | | | | | | | |
       3'P-dT dT dT dU dT dT dT dT dU dT dT dT dT dU dT dT dT dT dU-5'

⇩ Heat inactivation of TdT by incubation at 94°C, followed by incubation with USER enzyme mix (New England Biolabs) to degrade the attenuator molecules Tailed DNA primer with limited poly(dA) tail ~13 b 5'————dA dA dA dA dA dA dA dA dA dA dA dA dA-3'        3' dT dT dT -5'

RNA primer

5' ——————→ 3'

⇩ Poly (U) polymerase + UTP

Attenuator (dA)$_{30}$

3'P –dA dA dA dA dA dA dA dA dA dA dA dA dA dA dA dA dA dA dA dA dA dA dA dA dA dA dA dA dA dA- 5'

Tailed RNA primer

5' ——————— rU rU rU rU rU rU rU rU rU -3'

Attenuator (dA)$_{30}$

3'P –dA dA dA dA dA dA dA dA dA dA dA dA dA dA dA dA dA dA dA dA dA dA dA dA dA dA dA dA dA dA- 5'

⇩

Tailed RNA primer – Attenuator (dA)$_{30}$ complex with Tm = or > 37°C

SEQUENCE LISTING

<160> NUMBER OF SEQ ID NOS: 92

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 1
ggtcgtagca gtcgttgatg                                                 20

<210> SEQ ID NO 2
<211> LENGTH: 50
<212> TYPE: DNA
<213> ORGANISM: Artificial Sequence
<220> FEATURE:
<223> OTHER INFORMATION: Description of Artificial Sequence: Synthetic oligonucleotide

<400> SEQUENCE: 2
tagttgctgc aacctagtct agatctataa acgcaccttt ggacacgggg                50

<210> SEQ ID NO 3
<211> LENGTH: 56
<212> TYPE: DNA
<213> ORGANISM: Artificial Sequence
<220> FEATURE:
<223> OTHER INFORMATION: Description of Artificial Sequence: Synthetic oligonucleotide
<220> FEATURE:
<223> OTHER INFORMATION: 3' Phosphate

<400> SEQUENCE: 3
ccccgtgtcc aaaggtgcgt ttatagatct agatctagac taggttgcag caacta         56

```
<210> SEQ ID NO 4
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 4
tagttgctgc aacctagtct agatctataa acgcaccttt ggacactttt          50

<210> SEQ ID NO 5
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 5
aaaagtgtcc aaaggtgcgt ttatagatct agactaggtt gcagcaacta          50

<210> SEQ ID NO 6
<211> LENGTH: 59
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 6
cgtgtccaaa ggtgcgttta tagatctaga tctagatcta gactaggttg cagcaacta    59

<210> SEQ ID NO 7
<211> LENGTH: 65
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 7
ggtccccgtg tccaaaggtg cgtttataga tctagatcta gatctagact aggttgcagc    60
aacta                                                              65

<210> SEQ ID NO 8
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
gtatcgctac gttgtcacac actacactgc tcgacagtaa atatgccaag          50

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
``` oligonucleotide
<220> FEATURE:
<221> NAME/KEY: modified_base
<222> LOCATION: (13)..(23)
<223> OTHER INFORMATION: a, c, t, g, unknown or other

<400> SEQUENCE: 9
gatcgtagct agnnnnnnnn nnng                                      24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(23)
<223> OTHER INFORMATION: a, c, t, g, unknown or other

<400> SEQUENCE: 10
gatcgtagct agnnnnnnnn nnnc                                      24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(23)
<223> OTHER INFORMATION: a, c, t, g, unknown or other

<400> SEQUENCE: 11
gatcgtagct agnnnnnnnn nnnt                                      24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: modified_base
<222> LOCATION: (13)..(23)
<223> OTHER INFORMATION: a, c, t, g, unknown or other

<400> SEQUENCE: 12
gatcgtagct agnnnnnnnn nnna                                      24

<210> SEQ ID NO 13
<211> LENGTH: 19
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 13
ggccuuguuc cugucccca                                            19

<210> SEQ ID NO 14
<211> LENGTH: 40
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3' Phosphate

<400> SEQUENCE: 14
tttttutttt tuttttutt tttutttttu ttttttutttt                           40

<210> SEQ ID NO 15
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 15
gatcgtautt tttttuu                                                    17

<210> SEQ ID NO 16
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 16
gatcgtautt ttttttuu                                                   18

<210> SEQ ID NO 17
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 17
gatcgtautt tttttttuu                                                  19

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 18
gatcgtautt ttttttttuu                                                 20

<210> SEQ ID NO 19
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 19
gatcgtautt tttttttttu u                                                    21

<210> SEQ ID NO 20
<211> LENGTH: 22
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 20
gatcgtautt tttttttttt uu                                                   22

<210> SEQ ID NO 21
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 21
aaaaaaaaaa aaaaaaaaaa                                                      20

<210> SEQ ID NO 22
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 22
cccccccccc cccccccccc                                                      20

<210> SEQ ID NO 23
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 23
gggggtgggg gtgggggtgg gggtgggggt ggggtgggg                                 40

<210> SEQ ID NO 24
<211> LENGTH: 40
<212> TYPE: DNA
```

<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: 3' Phosphate

<400> SEQUENCE: 24
aaaaaaaaaa aaaaaaaaaa aaaaaaaaaa aaaaaaaaaa                    40

<210> SEQ ID NO 25
<211> LENGTH: 30
<212> TYPE: RNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: 3' Phosphate

<400> SEQUENCE: 25
aaaaaaaaaa aaaaaaaaaa aaaaaaaaaa                               30

<210> SEQ ID NO 26
<211> LENGTH: 45
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: Description of Combined DNA/RNA Molecule:
     Synthetic oligonucleotide
<220> FEATURE:
<223> OTHER INFORMATION: 5' Biotin

<400> SEQUENCE: 26
tacactcttt ccctacacga cgctcttccg atctttttttt tttuu             45

<210> SEQ ID NO 27
<211> LENGTH: 33
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: 5' Phosphate
<220> FEATURE:
<223> OTHER INFORMATION: 3' Phosphate

<400> SEQUENCE: 27
gatcggaaga gcgtcgtgta gggaaagagt gta                           33

<210> SEQ ID NO 28
<211> LENGTH: 32
<212> TYPE: DNA
<213> ORGANISM: Artificial Sequence
<220> FEATURE:
<223> OTHER INFORMATION: Description of Artificial Sequence: Synthetic
     oligonucleotide
<220> FEATURE:
<223> OTHER INFORMATION: 5' Phosphate
<220> FEATURE:
<223> OTHER INFORMATION: 3' Phosphate

<400> SEQUENCE: 28
cttattgctg tggttggttc ctgtgctgtt tt                            32

```
<210> SEQ ID NO 29
<211> LENGTH: 36
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3' Phosphate

<400> SEQUENCE: 29
ccaaccacag caauaagutt tuttttuttt tutttt                               36

<210> SEQ ID NO 30
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
ggtcgtagca gtcgttgatg                                                 20

<210> SEQ ID NO 31
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
ggtcgtagca gtcgttgatg aaaaa                                           25

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
ggtcgtagca gtcgttgatg aaaaaaaaaa                                      30

<210> SEQ ID NO 33
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
ggtcgtagca gtcgttgatg aaaaaaaaaa aaaaa                                35

<210> SEQ ID NO 34
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
```
ggtcgtagca gtcgttgatg aaaaaaaaaa aaaaaaaaa      40

<210> SEQ ID NO 35
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
tagttgctgc aacctagtct agatctataa acgcaccttt ggacacgggg      50

<210> SEQ ID NO 36
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 36
ccccgtgtcc aaaggtgcgt ttatagatct agactaggtt gcagcaacta      50

<210> SEQ ID NO 37
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tagttgctgc aacctagtct agatctataa acgcaccttt ggacactttt      50

<210> SEQ ID NO 38
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 38
aaaagtgtcc aaaggtgcgt ttatagatct agactaggtt gcagcaacta      50

<210> SEQ ID NO 39
<211> LENGTH: 47
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 39
cgtgtccaaa ggtgcgttta tagatctaga ctaggttgca gcaacta      47

<210> SEQ ID NO 40
<211> LENGTH: 53
<212> TYPE: DNA
<213> ORGANISM: Artificial Sequence

```
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 40
ggtccccgtg tccaaaggtg cgtttataga tctagactag gttgcagcaa cta         53

<210> SEQ ID NO 41
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Phosphate
<220> FEATURE:
<223> OTHER INFORMATION: 3' Phosphate

<400> SEQUENCE: 41
gatcggaaga gcgtcgtgta gggaaagagt gta                               33

<210> SEQ ID NO 42
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 5' Biotin
<220> FEATURE:
<223> OTHER INFORMATION: 3' Phosphate

<400> SEQUENCE: 42
tacactcttt ccctacacga cgctcttccg atctttttttt tttuu                 45

<210> SEQ ID NO 43
<211> LENGTH: 39
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 43
tttttutttt tuttttttutt tttuttttttu tttttuttt                       39

<210> SEQ ID NO 44
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 44
ccatctcatc cctgcgtgtc tccgactcag                                   30

<210> SEQ ID NO 45
<211> LENGTH: 41
```

```
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 45
ccactacgcc tccgctttcc tctctatggg cagtcggtga t                    41

<210> SEQ ID NO 46
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Phosphate

<400> SEQUENCE: 46
gatcggaaga gctcgtatgc cgtcttctgc ttg                             33

<210> SEQ ID NO 47
<211> LENGTH: 33
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
acactctttc cctacacgac gctcttccga tct                             33

<210> SEQ ID NO 48
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
ccatctcatc cctgcgtgtc tccgactcag                                 30

<210> SEQ ID NO 49
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 49
cctatcccct gtgtgccttg gcagtctcag                                 30

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
ccactacgcc tccgctttcc tctctatggg cagtcggtga t                    41

<210> SEQ ID NO 51
```

```
<211> LENGTH: 25
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 51
agagaatgag gaacccgggg cagtt                                           25

<210> SEQ ID NO 52
<211> LENGTH: 44
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 5' Phosphate
<220> FEATURE:
<221> NAME/KEY: modified_base
<222> LOCATION: (1)..(10)
<223> OTHER INFORMATION: a, c, t, g, unknown or other
<220> FEATURE:
<221> NAME/KEY: modified_base
<222> LOCATION: (35)..(44)
<223> OTHER INFORMATION: a, c, t, g, unknown or other

<400> SEQUENCE: 52
nnnnnnnnnn tgcctcctgg actatgtccg ggtannnnnn nnnn                      44

<210> SEQ ID NO 53
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (13)..(19)
<223> OTHER INFORMATION: a, c, t, g, unknown or other
<220> FEATURE:
<223> OTHER INFORMATION: 3' 3SpC3 spacer

<400> SEQUENCE: 53
cagtcggtga ttnnnnnnn                                                  19

<210> SEQ ID NO 54
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (14)..(19)
<223> OTHER INFORMATION: a, c, t, g, unknown or other
<220> FEATURE:
<223> OTHER INFORMATION: 3' 3SpC3 spacer

<400> SEQUENCE: 54
cagtcggtga tttnnnnnn                                                  19
```

```
<210> SEQ ID NO 55
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (15)..(19)
<223> OTHER INFORMATION: a, c, t, g, unknown or other
<220> FEATURE:
<223> OTHER INFORMATION: 3' 3SpC3 spacer

<400> SEQUENCE: 55
cagtcgguga ttttnnnnn                                                  19

<210> SEQ ID NO 56
<211> LENGTH: 19
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<221> NAME/KEY: modified_base
<222> LOCATION: (17)..(19)
<223> OTHER INFORMATION: a, c, t, g, unknown or other
<220> FEATURE:
<223> OTHER INFORMATION: 3' 3SpC3 spacer

<400> SEQUENCE: 56
cagtcgguga tttttnnn                                                   19

<210> SEQ ID NO 57
<211> LENGTH: 23
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3' 3SpC3 spacer

<400> SEQUENCE: 57
cagtcggtga uttttuttt ttt                                              23

<210> SEQ ID NO 58
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3' 3SpC3 spacer

<400> SEQUENCE: 58
cagtcgguga tcccccc                                                    17
```

<210> SEQ ID NO 59
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<223> OTHER INFORMATION: 3' 3SpC3 spacer

<400> SEQUENCE: 59
cagtcgguga tkkkkkk                                                  17

<210> SEQ ID NO 60
<211> LENGTH: 17
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: Description of Combined DNA/RNA Molecule:
    Synthetic oligonucleotide
<220> FEATURE:
<223> OTHER INFORMATION: 3' 3SpC3 spacer

<400> SEQUENCE: 60
cagtcgguga trrrrrr                                                  17

<210> SEQ ID NO 61
<211> LENGTH: 23
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: 5' Phosphate
<220> FEATURE:
<223> OTHER INFORMATION: 3' Phosphate

<400> SEQUENCE: 61
atcaccgact gcccatagag agg                                           23

<210> SEQ ID NO 62
<211> LENGTH: 30
<212> TYPE: DNA
<213> ORGANISM: Artificial Sequence
<220> FEATURE:
<223> OTHER INFORMATION: Description of Artificial Sequence: Synthetic
    oligonucleotide
<220> FEATURE:
<223> OTHER INFORMATION: 3' Phosphate

<400> SEQUENCE: 62
tttttttttt tttttttttt tttttttttt                                    30

<210> SEQ ID NO 63
<211> LENGTH: 14
<212> TYPE: DNA
<213> ORGANISM: Artificial Sequence
<220> FEATURE:
<223> OTHER INFORMATION: Description of Artificial Sequence: Synthetic
    oligonucleotide

<400> SEQUENCE: 63
aaaaaaaaaa aaaa                                                        14

<210> SEQ ID NO 64
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 64
tttttttttt ttt                                                         13

<210> SEQ ID NO 65
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 65
aaaaaaaaaa a                                                           11

<210> SEQ ID NO 66
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 66
aaaaaaaaaa aaa                                                         13

<210> SEQ ID NO 67
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 67
aaaaaaaaaa aaaaaaa                                                     17

<210> SEQ ID NO 68
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 68
aaaaaaaaaa aaaaaaaaaa aaaaaaaaaa                                       30

<210> SEQ ID NO 69
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:

```
              Synthetic oligonucleotide
<220> FEATURE:
<223> OTHER INFORMATION: 3' Phosphate

<400> SEQUENCE: 69 uttttuttt uttttuttt uttttuttt                                   30

<210> SEQ ID NO 70
<211> LENGTH: 30
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3' Phosphate

<400> SEQUENCE: 70 uttttuttt uttttuttt uttttuttt                                   30

<210> SEQ ID NO 71
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 71
gggggggggg gggggggggg                                           20

<210> SEQ ID NO 72
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 72
uuuuuuuuuu uuu                                                  13

<210> SEQ ID NO 73
<211> LENGTH: 13
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 73
aaaaaaaaaa aaa                                                  13

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 74
aaaaaaaaaa aaaaaaaaaa                                           20
```

```
<210> SEQ ID NO 75
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 75
aaaaaaaaaa aaaaa                                                          15

<210> SEQ ID NO 76
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 76
aaaaaaaaaa                                                                10

<210> SEQ ID NO 77
<211> LENGTH: 60
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 77
aaaaaaaaaa aaaaaaaaaa aaaaaaaaaa aaaaaaaaaa aaaaaaaaaa aaaaaaaaaa         60

<210> SEQ ID NO 78
<211> LENGTH: 45
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 78
aaaaaaaaaa aaaaaaaaaa aaaaaaaaaa aaaaaaaaaa aaaaa                         45

<210> SEQ ID NO 79
<211> LENGTH: 300
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: misc_feature
<222> LOCATION: (1)..(300)
<223> OTHER INFORMATION: This sequence may encompass 100-300 nucleotides

<400> SEQUENCE: 79
aaaaaaaaaa aaaaaaaaaa aaaaaaaaaa aaaaaaaaaa aaaaaaaaaa aaaaaaaaaa         60
aaaaaaaaaa aaaaaaaaaa aaaaaaaaaa aaaaaaaaaa aaaaaaaaaa aaaaaaaaaa        120
aaaaaaaaaa aaaaaaaaaa aaaaaaaaaa aaaaaaaaaa aaaaaaaaaa aaaaaaaaaa        180
aaaaaaaaaa aaaaaaaaaa aaaaaaaaaa aaaaaaaaaa aaaaaaaaaa aaaaaaaaaa        240
aaaaaaaaaa aaaaaaaaaa aaaaaaaaaa aaaaaaaaaa aaaaaaaaaa aaaaaaaaaa        300
```

```
<210> SEQ ID NO 80
<211> LENGTH: 62
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 80
tagttgctgc aacctagtct agatctataa acgcaccttt ggacacgggg aaaaaaaaaa    60
aa                                                                  62

<210> SEQ ID NO 81
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 81
aaaaaaaaaa aa                                                       12

<210> SEQ ID NO 82
<211> LENGTH: 95
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: 3' Phosphate

<400> SEQUENCE: 82
tagttgctgc aacctagtct agatctataa acgcaccttt ggacacgggg aaaaaaaaaa    60
aagatcggaa gagcgtcgtg tagggaaaga gtgta                              95

<210> SEQ ID NO 83
<211> LENGTH: 37
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 83
ggccuuguuc cugucoccaa aaaaaaaaaa aaaaaaa                            37

<210> SEQ ID NO 84
<211> LENGTH: 69
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide
<220> FEATURE:
<223> OTHER INFORMATION: 3' Phosphate

<400> SEQUENCE: 84
ggccuuguuc cugucoccaa aaaaaaaaaa aaaaaaactt attgctgtgg ttggttcctg    60
tgctgtttt                                                           69

<210> SEQ ID NO 85
```

```
<211> LENGTH: 40
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 85
tttttttttt tttttttttt tttttttttt tttttttttt                             40

<210> SEQ ID NO 86
<211> LENGTH: 13
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<221> NAME/KEY: misc_feature
<222> LOCATION: (1)..(13)
<223> OTHER INFORMATION: This sequence may encompass 12-13 nucleotides

<400> SEQUENCE: 86
aaaaaaaaaa aaa                                                          13

<210> SEQ ID NO 87
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 87
aaaaaaaaaa aaaaaaaaaa                                                   20

<210> SEQ ID NO 88
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 88
ttttttttuu                                                              10

<210> SEQ ID NO 89
<211> LENGTH: 11
<212> TYPE: DNA
<213> ORGANISM: Artificial Sequence
<220> FEATURE:
<223> OTHER INFORMATION: Description of Artificial Sequence: Synthetic
      oligonucleotide
<220> FEATURE:
<223> OTHER INFORMATION: Description of Combined DNA/RNA Molecule:
      Synthetic oligonucleotide

<400> SEQUENCE: 89
tttttttttu u                                                            11

<210> SEQ ID NO 90
<211> LENGTH: 14
<212> TYPE: DNA
<213> ORGANISM: Artificial Sequence
<220> FEATURE:
```

```
<223> OTHER INFORMATION: Description of Artificial Sequence: Synthetic
      oligonucleotide
<220> FEATURE:
<221> NAME/KEY: misc_feature
<222> LOCATION: (1)..(14)
<223> OTHER INFORMATION: This sequence may encompass 12-14 nucleotides

<400> SEQUENCE: 90
tttttttttt tttt                                                       14

<210> SEQ ID NO 91
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 91
tttttttttt tt                                                         12

<210> SEQ ID NO 92
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 92
tttttttttt ttttt                                                      15
```

METHODS AND COMPOSITIONS FOR SIZE-CONTROLLED HOMOPOLYMER TAILING OF SUBSTRATE POLYNUCLEOTIDES BY A NUCLEIC ACID POLYMERASE

CROSS REFERENCE TO RELATED APPLICATIONS

This application is a continuation of U.S. application Ser. No. 16/906,165, filed Jun. 19, 2020, now issued as U.S. Pat. No. 11,118,207, the entire contents of which is hereby incorporated herein by reference. U.S. application Ser. No. 16/906,165 is a continuation of U.S. Non-Provisional application Ser. No. 15/898,460, filed Feb. 17, 2018, now issued as U.S. Pat. No. 10,731,194, which is a divisional of U.S. Non-Provisional application Ser. No. 14/384,113, filed Sep. 9, 2014, now issued as U.S. Pat. No. 9,896,709, which is a U.S. National Phase of International Application No. PCT/US2013/031104, filed Mar. 13, 2013, which claims the priority benefit under 35 U.S.C. § 119(e) of U.S. Provisional Application No. 61/610,296, filed Mar. 13, 2012, and U.S. Provisional Application No. 61/613,784, filed Mar. 21, 2012, the disclosures of each of which are incorporated herein by reference in their entirety.

The instant application contains a Sequence Listing which has been submitted electronically in ASCII format and is hereby incorporated by reference in its entirety. Said ASCII copy, created on Jul. 6, 2017, is named 17-21004-US_SL.txt and is 27,358 bytes in size.

FIELD OF THE INVENTION

The present invention is directed to methods and compositions for adding tails of specific lengths to a substrate polynucleotide. The invention also contemplates methods and compositions for immobilization of tailed substrates to a solid support.

BACKGROUND OF THE INVENTION

Many current next-generation sequencing (NGS) platforms require special DNA and RNA preparations prior to sequencing. Most commonly used preparations involve addition of adaptor sequences to the ends of double-stranded DNA fragments through a ligation reaction. The reaction typically involves blunt-ended DNA or DNA with a single deoxyadenosine (dA) nucleotide at the 3' end and a high concentration of DNA ligase, and the reaction results in formation of a significant number of chimeric templates. Template-independent polymerases such as DNA-specific terminal deoxynucleotidyl transferase (TdT), and RNA-specific poly(A) and poly(U) polymerases potentially represent an attractive alternative approach for preparation of DNA and RNA for NGS analysis with the challenging caveat that the length of polymeric tails produced by these enzymes varies in a wide range (from 20 to 500 nucleotides), depends on many factors, and is not easy to control, thus reducing their utility for NGS.

SUMMARY OF THE INVENTION

Accordingly, the present disclosure provides a composition comprising a nucleic acid polymerase and an attenuator molecule. The disclosure contemplates that the attenuator molecule is any biomolecule that associates with a tail sequence added to a substrate polynucleotide and controls the addition of a tail sequence to the 3' end of the substrate polynucleotide. The sequence that is added to the substrate polynucleotide is referred to herein as a tail sequence, or simply a tail, and the process of adding a nucleotide to a substrate polynucleotide is referred to herein as tailing. An attenuator molecule, as used herein, is a polynucleotide, a polypeptide, a polysaccharide, and combinations thereof. In aspects where the attenuator molecule is a polynucleotide, it is further contemplated that the polynucleotide is a circular molecule, or that the polynucleotide comprises a peptide nucleic acid, a Schizophyllan polysaccharide, a locked nucleic acid and combinations thereof.

As described above, the attenuator molecule associates with a tail sequence added to the substrate polynucleotide and controls the addition of nucleotides thereto. In some embodiments, the attenuator molecule is a polynucleotide that hybridizes to a sequence added to a substrate polynucleotide, wherein the number of nucleotides added to the substrate polynucleotide is essentially equal to the number of nucleotides in the portion of the attenuator molecule that associates with the tail sequence. In some aspects, the number of nucleotides added to the substrate polynucleotide is essentially equal to a multiple of the number of nucleotides in the attenuator molecule that associates with the tail sequence. As used herein, the terms "essentially" and "essentially equal" are understood to mean approximately or approximately equal.

In some embodiments, the nucleic acid polymerase is a template-independent polymerase. In one aspect, the nucleic acid polymerase is a DNA polymerase, and in a further aspect the DNA polymerase is terminal deoxynucleotidyl transferase (TdT). In related embodiments, the nucleic acid polymerase is a RNA polymerase, which in various aspects is selected from the group consisting of poly(A) polymerase, RNA-specific nucleotidyl transferase and poly(U) polymerase.

It is contemplated by the disclosure that, in some embodiments, the attenuator molecule comprises a nucleotide selected from the group consisting of 2'-deoxythymidine 5'-monophosphate (dTMP), 2'-deoxyguanosine 5'-monophosphate (dGMP), 2'-deoxyadenosine 5'-monophosphate (dAMP), 2'-deoxycytidine 5'-monophosphate (dCMP), 2'-deoxyuridine 5'-monophosphate (dUMP), thymidine monophosphate (TMP), guanosine monophosphate (GMP), adenosine monophosphate (AMP), cytidine monophosphate (CMP), uridine monophosphate (UMP), a base analog, and combinations thereof. Thus, in certain embodiments the attenuator molecule comprises an attenuator sequence that is a heteropolymeric sequence or a homopolymeric sequence, wherein the sequence is either a dinucleotide sequence or a homopolymer sequence.

In various aspects, the attenuator molecule comprises 1 nucleotide, 2 nucleotides, 3 nucleotides, 4 nucleotides, 5 nucleotides, 10 nucleotides, 20 nucleotides, 30 nucleotides, 50 nucleotides, 100 nucleotides or more.

The attenuator molecule, in some embodiments, comprises a blocking group and in one aspect, the blocking group is on the 3' end of the molecule. The blocking group prevents extension of the attenuator molecule by the nucleic acid polymerase. Thus, in various aspects the blocking group is selected from the group consisting of at least one ribonucleotide, at least one deoxynucleotide, a C3 spacer, a phosphate, a dideoxynucleotide, an amino group, and an inverted deoxythymidine.

In some embodiments of the disclosure, the attenuator molecule further comprises an adaptor sequence, an identifier tag sequence, or both, located 5' to the attenuator sequence homopolymer sequence or dinucleotide sequence. hi one embodiment, the attenuator molecule is immobilized. In further embodiments, a ligase is present in the composition. In another embodiment, the composition further comprises a ligase enzyme.

In another embodiment, the attenuator molecule is an attenuator-adaptor molecule which comprises an attenuator sequence and further comprises a sequence W positioned adjacent the attenuator sequence and is complementary to a sequence X on a separate polynucleotide; the composition further comprising an adaptor molecule comprising a sequence Y complementary to a sequence V, wherein sequence V is the same length as Y or is less than the same length as sequence Y, the adaptor molecule being a separate molecule from the attenuator-adaptor molecule.

In some embodiments of the disclosure, the attenuator molecule further comprises a next generation sequencing (NGS) adaptor sequence. An NGS adaptor sequence differs from an adaptor sequence in that the NGS adaptor sequence is useful in a sequencing platform. In some embodiments of the disclosure, the attenuator molecule further comprises a next generation sequencing (NGS) adaptor sequence comprises sequence X and sequence Y (for further description of the various sequences (e.g., sequence X, sequence Y, etc.) discussed herein, see Figures and discussion, below), an identifier tag sequence, or a combination thereof, located 5' to a homopolymer sequence or dinucleotide sequence. In embodiments wherein the attenuator molecule further comprises an adaptor sequence, it is referred to herein as an attenuator-adaptor molecule. In one embodiment, the attenuator molecule and/or attenuator-adaptor molecule is immobilized. In related embodiments, sequence X and sequence Y are NGS adaptor sequences that are compatible with Illumina, Ion Torrent, Roche 454 or SOLiD sequencing platforms.

In further embodiments, sequence X and sequence Y are on separate attenuator-adaptor molecules, while in other embodiments sequence X and sequence Y are adjacent to each other on the same attenuator-adaptor molecule.

The disclosure also provides, in some embodiments, compositions wherein an adaptor sequence further comprises a cleavable sequence (Z) that is located between sequence X and sequence Y. In some aspects, the cleavage site in sequence Z is at least one dU base or RNA base, or a restriction endonuclease site.

Also provided by the disclosure are compositions wherein the attenuator molecule is single stranded or is at least partially double stranded. By "partially double stranded" is meant that the attenuator molecule comprises a single stranded portion and a double stranded portion. In some aspects wherein the attenuator molecule is at least partially double stranded, the partially double stranded attenuator molecule is produced by annealing a portion of the attenuator molecule to an adaptor molecule (which comprises an adaptor sequence that, in some embodiments, is an NGS adaptor sequence) to which it is complementary. In some aspects, annealing is (a) between an attenuator molecule and a separate adaptor molecule, or (b) annealing occurs in a single attenuator molecule that forms a hairpin structure, thus the attenuator molecule comprises both a homopolymeric sequence or dinucleotide sequence and an adaptor sequence.

In still further embodiments, the attenuator molecule comprises a sequence W that is fully complementary to adaptor sequence X. In some aspects, sequence W is also all or partially complementary to adaptor sequence Y.

In various aspects, the attenuator molecule comprises a homopolymeric sequence selected from the group consisting of poly (dA), poly (dT), poly (dC), poly (dG), poly (dU), poly (rA), poly (U), poly (rC), poly (rG) and a heteropolymeric, or a dinucleotide, sequence comprising combinations of: (i) dA and rA bases, (ii) dT, dU and U bases, (iii) dC and rC bases, or (iv) dG and rG bases.

In further aspects, the attenuator molecule comprises deoxyribonucleotides and is degradable with a DNA-specific nuclease. In some of these aspects, the DNA-specific nuclease is DNase I. In further embodiments, a composition provided by the disclosure comprises a single strand circularization ligase, including but not limited to CircLigase and/or CircLigase II.

The disclosure also provides, in some aspects, a composition that comprises a DNA polymerase which lacks proofreading activity, and Kapa HiFi Polymerase, which possesses proofreading activity. In additional embodiments, a composition of the disclosure comprises a ligase enzyme.

Further embodiments of the disclosure provide a composition that comprises a restriction endonuclease capable of cleaving sequence Z, which is located between sequence X and sequence Y and comprises a restriction endonuclease site, when hybridized to a complementary X'Z'Y' polynucleotide.

In some embodiments, a composition is provided wherein a partially double stranded adaptor sequence comprised of sequence V and sequence Y wherein V is a truncated complement of Y and comprises a blocked 3' end, such that the partially double stranded adaptor can be blunt ligated to a double stranded substrate molecule. In another embodiment, sequence V is fully complementary to sequence Y.

The disclosure further contemplates compositions wherein the attenuator molecule is degradable. In some aspects, the attenuator molecule comprises dU bases and is degradable by incubation with a dU-glycosylase (which creates abasic sites) followed by incubation at a temperature that is above 80° C. (introduces breaks within abasic sites), or a mixture of dU-glycosylase and an apurinic/apyrimidinic endonuclease. Thus, the disclosure provides compositions, in various aspects, wherein the attenuator molecule comprises dU bases and incubation with a dU-glycosylase destabilizes the attenuator molecule, or incubation with a dU¬glycosylase and subsequent incubation at a temperature that is above 80° C. degrades the attenuator molecule, or the attenuator molecule is incubated with a mixture of dU-glycosylase and an apurinic/apyrimidinic endonuclease. In further aspects, the attenuator molecule comprises a ribonucleotide and is degradable with a ribonuclease under conditions sufficient for ribonuclease activity. In related aspects, the ribonuclease is selected from the group consisting of RNase H, RNase HII, RNase A, and RNase T1.

In further aspects, the attenuator molecule comprises deoxyribonucleotides and is degradable with a DNA-specific nuclease. In some of these aspects, the DNA-specific nuclease is DNase I.

The disclosure also provides a method of extending a substrate polynucleotide comprising incubating the substrate polynucleotide with a composition as described herein under conditions sufficient to allow addition of a tail sequence to the 3' end of the substrate polynucleotide, and wherein the addition of the tail sequence allows association between the tail sequence and the attenuator molecule to form a complex. In another aspect, the method further comprises degrading the attenuator molecule following extension of the substrate polynucleotide. In a further aspect, the method further comprises isolating the extended substrate polynucleotide.

Other aspects of the methods further comprise mixing a composition as described herein with the substrate polynucleotide and a nucleotide that is complementary to the homopolymeric portion of the attenuator molecule.

According to various aspects of the disclosure, the substrate polynucleotide is a single stranded polynucleotide or is a double stranded polynucleotide. The double stranded polynucleotide, in some aspects, has a blunt end, a 3' overhanging end, a 3' recessed end, or a free 3' hydroxyl group. The present disclosure provides methods wherein the substrate polynucleotide is double stranded, and in certain aspects, the double stranded substrate polynucleotide is produced by annealing a first substrate polynucleotide to a second substrate polynucleotide under conditions sufficient to allow the first substrate polynucleotide to associate with the second substrate polynucleotide. According to further aspects of the disclosure, the substrate polynucleotide comprises a free 3' hydroxyl group. The single stranded polynucleotide, in various embodiments, is prepared by denaturation of fragmented double stranded DNA or from reverse transcription of RNA. The double stranded polynucleotide, in some aspects, has a blunt end or a 3' overhanging end with a free 3' hydroxyl group.

In various aspects of the methods of the disclosure, a multiplicity of nucleotides are added to the substrate polynucleotide. The number of nucleotides added to the substrate polynucleotide comprises, in various aspects, at least about 1 nucleotide and up to about 10, 20, 50 or 100 nucleotides, at least about 3 nucleotides and up to about 10, 20, 50 or 100 nucleotides, at least about 10 nucleotides and up to about 20, 30, 50 or 100 nucleotides, at least about 5 nucleotides and up to about 10, 20, 50 or 100 nucleotides, at least about 10 nucleotides and up to about 20, 30, 50 or 100 nucleotides, at least about 1 nucleotide and up to about 5, 10, or 20 nucleotides, at least about 3 nucleotides and up to about 5, 10, or 20 nucleotides, at least about 5 nucleotides and up to about 20, 40 or 50 nucleotides, at least 1 nucleotide, at least 2 nucleotides, at least 3 nucleotides, at least 4 nucleotides, at least 5 nucleotides, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, at least 30, at least 31, at least 32, at least 33, at least 34, at least 35, at least 36, at least 37, at least 38, at least 39, at least 40, at least 41, at least 42, at least 43, at least 44, at least 45, at least 46, at least 47, at least 48, at least 49, at least 50, at least 51, at least 52, at least 53, at least 54, at least 55, at least 56, at least 57, at least 58, at least 59, at least 60, at least 61, at least 62, at least 63, at least 64, at least 65, at least 66, at least 67, at least 68, at least 69, at least 70, at least 71, at least 72, at least 73, at least 74, at least 75, at least 76, at least 77, at least 78, at least 79, at least 80, at least 81, at least 82, at least 83, at least 84, at least 85, at least 86, at least 87, at least 88, at least 89, at least 90, at least 91, at least 92, at least 93, at least 94, at least 95, at least 96, at least 97, at least 98, at least 99, at least 100 nucleotides or more.

Further embodiments provided by the disclosure include those wherein the attenuator molecule associates with the tail sequence over all or a portion of the attenuator molecule length. In some embodiments, the attenuator molecule associates with the tail sequence during the process of adding the tail sequence. Association of the attenuator molecule to the tail sequence, in further aspects, regulates addition of nucleotides to the substrate polynucleotide. The attenuator molecule additionally comprises an adaptor sequence, in some aspects, and the adaptor sequence is ligated by a ligase enzyme to the substrate polynucleotide during addition of the tail sequence to the substrate polynucleotide, and in various embodiments the ligase is a DNA ligase or a RNA ligase.

It is also contemplated by the disclosure that the conditions of the method, in some aspects, regulate addition of the tail sequence to the substrate polynucleotide. With respect to the conditions that are contemplated to regulate addition of the tail sequence to the substrate polynucleotide, it is contemplated that, in some aspects, the addition of the tail sequence to the substrate polynucleotide is temperature sensitive. Conditions wherein the temperature is between about 4° C. and about 50° C. are contemplated. In aspects wherein a thermostable polymerase is used, the temperature can be above 50° C. Accordingly, in further aspects the temperature is between about 50° C. and about 90° C.

In another embodiment, the addition of the tail sequence to the substrate polynucleotide is time sensitive, and in various aspects the incubation step is allowed to progress for a length of time in the range of about 0.5 minutes to about 120 minutes. In further embodiments, the addition of the tail sequence to the substrate polynucleotide is pH sensitive. In some of these embodiments, the addition of the tail sequence to the substrate polynucleotide is performed under conditions wherein pH is in the range of about pH 5.0 to about pH 9.0.

In various embodiments, the substrate polynucleotide is DNA or RNA.

Methods provided herein also include those wherein the attenuator-adaptor molecule is immobilized. In some aspects, the immobilized attenuator-adaptor molecule is ligated by a DNA or RNA ligase to a substrate polynucleotide during addition of a tail sequence to the substrate polynucleotide resulting in immobilization of the substrate polynucleotide. In further aspects, the amount of ligase enzyme added to a reaction is from about 0.1 to about 1000 units (U).

In certain aspects, the methods described herein further comprise magnesium in an amount of about 1 mM to about 100 mM. In further aspects, the methods further comprise potassium or sodium in an amount of about 1 mM to about 1 M.

In a specific aspect of the disclosure, a method of extending a DNA substrate polynucleotide is provided comprising mixing the DNA substrate polynucleotide with TdT enzyme, a degradable attenuator polynucleotide comprising a 3' phosphate and nucleotides that are complementary to the homopolymeric portion of the attenuator polynucleotide, incubating the mixture at 37° C. for about 30 minutes, followed by an additional incubation at 70° C. for about 10 minutes, degrading the attenuator molecule by adding a DNA glycosylase and incubating the mixture at 37° C. for about 5 minutes, and optionally isolating the extended DNA substrate polynucleotide.

In another aspect, the disclosure provides a method of extending a DNA substrate polynucleotide comprising mixing a substrate polynucleotide with TdT enzyme, an attenuator polynucleotide comprising two ribonucleotides at the 3' end, and nucleotides that are complementary to the homopolymeric portion of the attenuator polynucleotide, incubating the mixture at 30° C. for 30 minutes, followed by an additional incubation at 70° C. for about 10 minutes to inactivate the TdT enzyme, and optionally isolating the extended DNA substrate polynucleotide.

The disclosure further provides, in one aspect, a method of extending a substrate RNA polynucleotide comprising mixing the substrate RNA polynucleotide with an RNA polymerase, a degradable attenuator polynucleotide and ribonucleotides that are complementary to the homopolymeric portion of the attenuator polynucleotide, incubating the mixture at 30° C. for about 30 minutes, followed by an additional incubation at 95° C. for about 10 minutes, degrading the attenuator molecule by adding a DNA glycosylase and incubating the mixture at 37° C. for about 10 minutes, and optionally isolating the extended substrate polynucleotide.

In another aspect, the disclosure provides a method of extending a DNA substrate polynucleotide comprising annealing attenuator and adaptor molecules that are partially complementary to each other by heating a mixture of the attenuator and the adaptor molecules in a suitable buffer to about 100° C. and then cooling to about 25° C., wherein the annealing results in a partially double stranded attenuator-adaptor molecule, mixing the DNA substrate polynucleotide with TdT enzyme, a ligase enzyme, the partially double stranded attenuator-adaptor molecule and nucleotides that are complementary to the homopolymeric portion of the attenuator-adaptor molecule, incubating at about 37° C. for about 15 to about 30 minutes, and optionally isolating the extended DNA substrate polynucleotide ligated to the attenuator-adaptor molecule.

The disclosure further provides, in one aspect, a method of extending a DNA substrate polynucleotide comprising annealing one attenuator-adaptor molecule to a second, biotinylated adaptor molecule that are at least partially complementary to each other by heating a mixture of the two molecules in a suitable buffer to about 100° C. and then cooling to about 25° C., wherein the annealing results in a double stranded biotinylated attenuator-adaptor molecule, immobilizing the double stranded biotinylated attenuator-adaptor molecule by mixing the double stranded biotinylated attenuator-adaptor molecule with a solution comprising a streptavidin-coated magnetic bead at about 25° C. for about 30 to about 60 minutes, resulting in immobilization of the double stranded biotinylated attenuator-adaptor molecule to the streptavidin-coated magnetic bead, incubating the immobilized double stranded biotinylated attenuator-adaptor molecule attached to the streptavidin-coated magnetic bead with the DNA substrate polynucleotide, TdT enzyme, a ligase enzyme and nucleotides that are complementary to the homopolymeric portion of the double stranded attenuator molecule at about 37° C. for 15 to about 30 minutes, washing the solution with NaOH to remove non-biotinylated single stranded DNA from the beads, and optionally isolating the extended DNA substrate polynucleotide ligated to the double stranded biotinylated attenuator-adaptor molecule.

In another aspect, a method of extending a RNA substrate polynucleotide is provided comprising annealing an attenuator molecule and an adaptor molecule that are at least partially complementary to each other by heating a mixture of the two molecules in a suitable buffer to about 100° C. and then cooling to about 25° C., wherein the annealing results in a partially double stranded attenuator-adaptor molecule; mixing an RNA substrate polynucleotide with poly (A) or poly(U) enzyme, a ligase enzyme, the partially double stranded attenuator-adaptor molecule and ribonucleotides that are complementary to the single-stranded homopolymeric portion of the partially double stranded attenuator molecule; incubating at about 30° C. to about 37° C. for about 15-30 minutes; and optionally isolating the extended RNA substrate polynucleotide ligated to the attenuator-adaptor molecule.

In a further aspect, the disclosure provides a method of extending and immobilizing an RNA substrate polynucleotide comprising annealing an attenuator-adaptor molecule to a biotinylated adaptor molecule that are at least partially complementary to each other by heating a mixture of the two molecules in a suitable buffer to about 100° C. and then cooling to about 25° C., wherein the annealing results in a partially double stranded biotinylated attenuator-adaptor molecule; immobilizing the partially double stranded biotinylated attenuator-adaptor molecule by mixing the partially double stranded biotinylated attenuator-adaptor molecule with a solution comprising a streptavidin-coated magnetic bead at about 25° C. for about two hours, resulting in immobilization of the partially double stranded biotinylated attenuator-adaptor molecule to the streptavidin-coated magnetic bead; incubating the immobilized partially double stranded biotinylated attenuator-adaptor molecule attached to the streptavidin-coated magnetic bead with the RNA substrate polynucleotide, poly(A) or poly(U) polymerase, a ligase enzyme and ribonucleotides that are complementary to the single stranded homopolymeric portion of the partially double stranded attenuator-adaptor molecule at about 30° C. to about 37° C. for about 15-30 minutes; washing the solution with NaOH to remove non-biotinylated single stranded polynucleotide from the beads; and optionally isolating the extended and immobilized RNA substrate polynucleotide ligated to the double stranded biotinylated attenuator-adaptor molecule.

The disclosure also provides, in various embodiments, methods wherein a DNA polymerase and dNTPs are mixed to perform a polymerase extension of a substrate polynucleotide, said polymerase extension occurring subsequent to controlled homopolymer tailing and leading to incorporation of NGS adaptor sequence(s) sequence X, sequence Y or sequences X and Y 3' to the substrate homopolymer that are complementary to the additional sequence X' and sequence Y' that are 5' to the homopolymer of the attenuator molecule.

In further embodiments, NGS adaptor sequence X, sequence Y or sequences X and Y are optionally ligated by a ligase enzyme to the substrate polynucleotide during addition of nucleotides to the substrate polynucleotide. In other embodiments, NGS adaptor sequence X, sequence Y or sequences X and Y are optionally ligated by a ligase enzyme to the substrate polynucleotide after addition of nucleotides to the substrate polynucleotide. In related embodiments, the ligase is a DNA ligase or a RNA ligase.

In still further embodiments, an attenuator molecule sequence W is optionally truncated with respect to sequences X' and Y' to allow a full-length X'Y' polynucleotide primer to displace the truncated attenuator and enable polymerase extension to create a double stranded adapted substrate molecule. As used herein, an "adapted molecule" is a substrate molecule that has undergone a tailing and ligation reaction.

The disclosure further provides embodiments wherein the substrate molecule, following homopolymer addition and polymerase extension, is optionally incubated with a single stranded DNA circularization ligase that results in circularization of the adapted single stranded DNA molecule. In one embodiment, circularization of the attenuator molecule comprising sequence X and sequence Y is prevented by degradation.

In another embodiment, the substrate molecule, following homopolymer addition and ligation, is optionally incubated with a single stranded DNA circularization ligase which results in circularization of the adapted single stranded DNA molecule.

In a further embodiment of the disclosure, circularization of the XZY adaptor molecule is prevented by formation of a double-stranded or partially double-stranded attenuator-adaptor molecule.

Embodiments of the disclosure contemplate cleavage of the circular DNA molecule at sequence Z, said cleavage resulting from incubation with, for example and without limitation, dU glycosylase and an apurinic/apyrimidinic endonuclease in embodiments wherein Z comprises dU bases.

Further embodiments of the disclosure include cleavage of the circular DNA molecule at sequence Z, said cleavage resulting from incubation with RNase H, RNase H II (in embodiments wherein Z comprises RNA bases) or by a restriction enzyme, following hybridization of an oligonucleotide complementary to the XZY junction.

In further aspects, the disclosure provides a method of extending a DNA substrate polynucleotide comprising: mixing the DNA substrate polynucleotide with a polymerase enzyme and a ligase enzyme, an adaptor polynucleotide comprising NGS adaptor sequences X and Y and cleavable sequence Z, wherein the adaptor optionally comprises a 3' ribonucleotide and a 5' phosphate, and is annealed to an attenuator with a truncated NGS adaptor sequence W and 3' block, and deoxynucleotides that are complementary to the homopolymeric portion of the attenuator polynucleotide; performing the tailing and ligation simultaneous reaction, heat inactivating the polymerase and ligase enzymes, followed by incubation with a single strand specific circularization ligase enzyme; optionally including a cleavage reaction at the Z sequence or an amplification reaction with reverse X and Y primers, either of which is performed to resolve the circular molecule into a completed linear NGS library molecule.

In another aspect, the disclosure provides a method of extending a DNA substrate polynucleotide comprising mixing a DNA substrate polynucleotide with a polymerase enzyme, an attenuator with NGS adaptor sequences X' and Y' and comprising a 3' extension block and a cleavage site as described herein, and deoxynucleotides that are complementary to the homopolymeric portion of the attenuator polynucleotide; performing the tailing reaction, heat inactivating the polymerase enzyme, followed by addition of a DNA polymerase and dNTP mix to perform a polymerase extension to the tailed substrate polynucleotide to incorporate NGS adaptor sequences X and Y 3' of the homopolymer addition on the substrate; the attenuator¬template polynucleotide is then degraded with RNase or dU-glycosylase, followed by incubation with a single strand specific circularization ligase enzyme; optionally including a cleavage reaction at a Z sequence or an amplification reaction with reverse X and Y primers, either of which is performed to resolve the circular molecule into a completed linear NGS library molecule.

In another aspect, the disclosure provides a method of extending a DNA substrate polynucleotide comprising mixing the DNA substrate polynucleotide with a polymerase enzyme and a ligase enzyme, an adaptor polynucleotide comprising the NGS adaptor sequence X, wherein the adaptor optionally comprises a 3' extension block and a 5' phosphate, and is annealed to an attenuator with a truncated NGS adaptor sequence W and 3' block, and deoxynucleotides that are complementary to the homopolymeric portion of the attenuator polynucleotide; performing the tailing and ligation simultaneous reaction, heat inactivating the polymerase and ligase enzymes, followed by incubation with a primer complementary to full-length NGS adaptor sequence X' that is capable of displacing the attenuator molecule, a DNA polymerase and dNTPs optionally including dUTP to perform an extension reaction to generate second strand and a double stranded substrate molecule with a blunt end; performing a ligation with T4 DNA ligase and a blunt-end adaptor which is formed by annealing two polynucleotides comprising NGS adaptor sequence Y and a truncated complement (sequence V) and a 3' phosphate, wherein the Y polynucleotide is ligated to the 5' phosphate of the substrate molecule to complete a linear NGS library molecule; optionally the synthesized strand is degraded using dU glycosylase and heat to 95° C.

A further aspect of the disclosure provides a method of extending a DNA substrate polynucleotide comprising: mixing the DNA substrate polynucleotide with a polymerase enzyme, an attenuator with NGS adaptor sequences X' and comprising a 3' extension block and a cleavage site, and deoxynucleotides that are complementary to a homopolymeric portion of the attenuator polynucleotide; performing a tailing reaction, heat inactivating the polymerase enzyme, followed by addition of a proofreading DNA polymerase and dNTP mix to perform a polymerase extension to incorporate NGS adaptor sequence X 3' of the homopolymer addition on the substrate and to remove non-complementary bases from the attenuator 3' end to enable polymerase extension to generate a blunt end double stranded substrate; performing a ligation with T4 DNA ligase and a blunt-end adaptor molecule which is formed by annealing two polynucleotides comprising NGS adaptor sequence Y and a truncated complement (sequence V) and a 3' phosphate, where the Y polynucleotide is ligated to the 5' phosphate of the substrate molecule to complete a linear NGS library molecule; optionally the synthesized strand is degraded using dU glycosylase and heat to between about 90° C. and 100° C. In various embodiments, the mixture is heated to between about 90° C. and 95° C., or between about 95° C. and 100° C., or is about 90° C., or about 91° C., or about 92° C., or about 93° C., or about 94° C., or about 95° C., or about 96° C., or about 97° C., or about 98° C., or about 99° C., or about 100° C.

In still another aspect, a method of extending an RNA substrate polynucleotide is provided comprising: mixing the RNA substrate polynucleotide with a Poly(A) or Poly(U) enzyme and T4 DNA ligase, a DNA adaptor polynucleotide comprising the NGS adaptor sequence X, wherein the adaptor optionally comprises a 3' extension block and a 5' phosphate, and is annealed to an RNA attenuator with a truncated NGS adaptor sequence W and 3' block, and ribonucleotides that are complementary to the homopolymeric portion of the attenuator polynucleotide; performing a tailing and ligation simultaneous reaction, heat inactivating the Poly(A) or Poly(U) enzyme, followed by incubation with a primer complementary to full-length NGS adaptor sequence X' that is capable of displacing the attenuator molecule truncated for sequence X', a reverse transcriptase and dNTPs to perform an extension reaction to generate a second strand and a double stranded substrate molecule; performing a magnetic bead DNA purification step followed by strand denaturation at 95° C.; a second simultaneous tailing and ligation is then performed using a polymerase enzyme and a ligase enzyme and a DNA attenuator-adaptor molecule that will add a homopolymer and Y NGS adaptor sequence to the free 3' end of the substrate molecule, thus completing a linear NGS library molecule where an optional DNA purification step is required.

The disclosure also provides a method of NGS library synthesis using controlled homopolymer tailing and ligation followed by circularization of the substrate polynucleotide (FIG. 25), where fragmented single stranded DNA is prepared by denaturation of fragmented double stranded DNA or by reverse transcription of RNA, wherein controlled tailing and ligation is performed in the presence of the polymerase enzyme, a ligase enzyme, nucleotide D (where D=dATP, dTTP or dGTP) and an attenuator-adaptor molecule, wherein the attenuator-adaptor molecule is formed by annealing two polynucleotides: polynucleotide XZY and polynucleotide W(H)n.

Polynucleotide XZY comprises a 5' phosphate, and a ribonucleotide base or other blocking group at the 3' end which prevents addition of a homopolymer tail. Sequences X and Y represent adaptor sequences of an NGS library and optional ID tag. Optional sequence Z is used for cleavage and is comprised of a dU base, an RNA base or a restriction endonuclease site. Polynucleotide W(H)n comprises two sequences: a 5' sequence W that is complementary to the 5' portion of the polynucleotide XZY and a homopolymeric attenuator sequence (H), where H is A, T or C base, and n=10-30. Polynucleotide W(H), comprises a 3' blocking group including but not limited to a 3' phosphate, dideoxynucleotide, C3-spacer, inverted thymidine or one or more ribonucleotides that specifically inhibit addition of bases by the polymerase enzyme. In the reaction, the polymerase enzyme will add a limited number of bases to the 3' end of DNA substrates followed by ligation of the XZY adaptor molecule by a ligase enzyme. In certain embodiments, the number of bases added by the polymerase to the 3' end of a DNA substrate is between about 1-50 dA or dT bases or between about 1-50 dG bases. In further embodiments, the number of bases added by the polymerase to the 3' end of a DNA substrate is from about 1 nucleotide and up to about 5, 10, 20, 30, 40 or 50 dA, dT or dG nucleotides, or from about 5 and up to about 10, 15, 20, 30, 40 or 50 dA, dT or dG nucleotides, or from about 10 and up to about 15, 20, 30, 40 or 50 dA, dT or dG nucleotides, or from about 9 to about 12 dA, dT or dG nucleotides, or from about 6 to about 8 dA, dT or dG nucleotides. In additional embodiments, the number of bases added by the polymerase to the 3' end of a DNA substrate is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49 or at least about 50 dA, dT or dG nucleotides. In further embodiments, the number of bases added by the polymerase to the 3' end of a DNA substrate is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more dA, dT or dG nucleotides.

Following optional heat inactivation of the polymerase enzyme and the ligase enzyme, incubation with single stranded circularization ligase (Epicentre/Illumina) results in circularization of the adapted single stranded DNA molecule. Circularization of the XZY polynucleotide is prevented by formation of a double-stranded attenuator-adaptor complex between the XZY and W(H), polynucleotides. Circularized NGS libraries can be directly used for cluster formation (emulsion PCR in the case of Ion Torrent, 454 and Solid platforms, and bridge amplification in the case of Illumina platforms) or directly for sequencing (PacBio). Optionally, cleavage of the circular DNA molecule is achieved by dU glycosylase and an apurinic/apyrimidinic endonuclease (in the case when Z sequence comprises a dU base), by RNase H or RNase H II (in the case when Z sequence comprises an RNA base) or by a restriction endonuclease. In the latter two cases, hybridization of a polynucleotide complementary to the XZY junction is necessary to provide a template for RNase H or restriction endonuclease. Alternatively, an amplification reaction is performed to resolve the circular to linear form.

The disclosure also provides an alternative method for NGS library synthesis using controlled homopolymer tailing followed by polymerase extension and circularization (FIG. 26), wherein tailing of single stranded substrate polynucleotides is performed in the presence of a polymerase enzyme, nucleotide D (where D=dATP, dTTP or dGTP) and an attenuator-template polynucleotide, where the attenuator-template polynucleotide comprises three sequences: a 5' sequence Y' that is complementary to adaptor sequence Y, sequence X' that is complementary to adaptor sequence X and a homopolymeric attenuator sequence (H), where H is A, T or C base, and n=10-30. The attenuator-template polynucleotide additionally comprises a phosphate group, ribonucleotide or other blocking group at the 3' end. Sequences X and Y represent adaptor sequences for an NGS library, and optional ID tag. Both the attenuator sequence and X',Y' sequences have degradable bases such as ribonucleotides or dU. In the presence of the attenuator molecule, a polymerase enzyme adds a limited number of bases to the 3' end of DNA. In certain embodiments, the number of bases added by the polymerase to the 3' end of a DNA substrate is between about 1-50 dA or dT bases or between about 1-50 dG bases. In further embodiments, the number of bases added by the polymerase to the 3' end of a DNA substrate is from about 1 nucleotide and up to about 5, 10, 20, 30, 40 or 50 dA, dT or dG nucleotides, or from about 5 and up to about 10, 15, 20, 30, 40 or 50 dA, dT or dG nucleotides, or from about 10 and up to about 12, 15, 20, 30, 40 or 50 dA, dT or dG nucleotides, or from about 10 to about 13 dA, dT or dG nucleotides. In additional embodiments, the number of bases added by the polymerase to the 3' end of a DNA substrate is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49 or at least about 50 dA, dT or dG nucleotides. In further embodiments, the number of bases added by the polymerase to the 3' end of a DNA substrate is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more dA, dT or dG nucleotides.

After optional heat inactivation of the polymerase enzyme and the ligase enzyme, a DNA polymerase and dNTP mix are added to perform polymerase extension which results in addition of X and Y sequences to the 3' end of the homopolymeric sequence (D). Following attenuator-template degradation by addition of dU-glycosylase or RNase, incubation with single strand circularization ligase (Epicentre/Illumina) results in circularization of the adapted single stranded DNA molecule. If necessary, an optional amplification is performed to resolve the circular to linear form. Alternatively an optional sequence Z between X and Y is used to create linear form following hybridization of a complementary polynucleotide to the XZY domain and a cleavage reaction (as described herein above). In certain embodiments, the optional amplification that is performed to resolve the circular to linear form is a technique including, without limitation, inverse PCR.

Also contemplated is a method of NGS library synthesis comprising controlled homopolymer tailing and ligation followed by reverse strand synthesis and blunt adaptor ligation (FIG. 27), wherein tailing and ligation are performed in the presence of TdT enzyme, E. coli DNA ligase, nucleotide D (where D=dATP, dTTP or dGTP) and an attenuator-adaptor molecule that is formed by annealing two polynucleotides: polynucleotide X and polynucleotide W(H)n. Polynucleotide X comprises a 5' phosphate and a 3' blocking group, where sequence X comprises an NGS library adaptor sequence and optional ID tag. Polynucleotide W(H)n consists of two sequences: a 5' sequence W that is complementary to the 5' portion of polynucleotide X and a homopolymeric attenuator sequence (H), where H is A, T or C base, and n=10-30, and additionally comprises a 3' blocking group. In the reaction, the polymerase enzyme adds a limited number of bases to the 3' end of DNA substrates followed by ligation of the attenuator-adaptor molecule by a ligase enzyme. In certain embodiments, the number of bases added by the polymerase to the 3' end of a DNA substrate is between about 1-50 dA or dT bases or between about 1-50 dG bases. In further embodiments, the number of bases added by the polymerase to the 3' end of a DNA substrate is from about 1 nucleotide and up to about 5, 10, 20, 30, 40 or 50 dA, dT or dG nucleotides, or from about 5 and up to about 10, 15, 20, 30, 40 or 50 dA, dT or dG nucleotides, or from about 10 and up to about 15, 20, 30, 40 or 50 dA, dT or dG nucleotides, or from about 9 to about 12 dA, dT or dG nucleotides, or from about 6 to about 8 dA, dT or dG nucleotides. In additional embodiments, the number of bases added by the polymerase to the 3' end of a DNA substrate is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49 or at least about 50 dA, dT or dG nucleotides. In further embodiments, the number of bases added by the polymerase to the 3' end of a DNA substrate is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more dA, dT or dG nucleotides.

Following optional heat inactivation of the polymerase enzyme and the ligase enzyme, addition of a DNA polymerase and primer containing 5' sequence X', 1-10 H bases (or, in further embodiments, from about 1 to about 5, 7, or 10 H bases, or from about 5 to about 6, 8 or 10 H bases, or from about 6 to about 8 H bases) at the 3' end and optional dU bases leads to reverse strand replication, thus forming either a double-stranded blunt end (in the presence of proofreading DNA polymerase) or double-stranded end with 3' dA base (in the case when DNA polymerase lacks the proofreading activity), and wherein the polymerization mix optionally comprises dUTP. Ligation of a blunt-end or dT-adaptor is achieved by a ligase enzyme, wherein the adaptor to be ligated is formed by two polynucleotides: polynucleotide Y, where Y is a second NGS adaptor and polynucleotide V that is complementary to the 3' portion of polynucleotide Y. The 3' end of polynucleotide V has a phosphate blocking group. Ligation results in covalent attachment of the 3' end of polynucleotide Y to the 5' phosphate of the original DNA fragment, whereas no ligation is formed between the 5' end of polynucleotide V and the 3' end of the primer-extension product. Optionally the replicated DNA strand and primer X' is degraded by incubation with dU glycosylase and 95° C. incubation. In some embodiments, the incubation takes place between about 90° C. and 100° C. In further embodiments, the mixture is heated to between about 90° C. and 95° C., or between about 95° C. and 100° C., or is about 90° C., or about 91° C., or about 92° C., or about 93° C., or about 94° C., or about 95° C., or about 96° C., or about 97° C., or about 98° C., or about 99° C., or about 100° C.

The disclosure also provides an alternative method for NGS library construction comprising controlled tailing and polymerization followed by reverse strand synthesis and blunt ligation (FIG. 28), wherein tailing is performed in the presence of the polymerase enzyme, nucleotide D (where D=dATP, dTTP or dGTP) and attenuator-template polynucleotide comprising two sequences: a 5' sequence X' that is complementary to NGS adaptor X, and a homopolymeric attenuator sequence (H), where H is A, T or C base, and n=10-30, and additionally comprises a 3' ribonucleotide and internal degradable bases such as ribonucleotide or dU. In the presence of the attenuator molecule, the polymerase enzyme adds a limited number of bases to the 3' end of DNA substrates and following optional heat inactivation, the inclusion of a DNA polymerase with proofreading activity and dNTP mix extends the DNA substrate to include sequence X and also removes excessive non-complementary bases from the attenuator polynucleotide 3' terminus and then leads to reverse strand replication which results in a double-stranded blunt end. The polymerization mix can optionally comprise dUTP. Ligation of a blunt-end adaptor is achieved by T4 DNA ligase, where the blunt-end adaptor is formed by two polynucleotides: polynucleotide Y, where Y is a sequence of second NGS adaptor and polynucleotide V that is complementary to the 3' portion of the polynucleotide Y, and where the 3' end of polynucleotide V comprises a phosphate or other blocking group. Blunt ligation results in covalent attachment of the 3' end of polynucleotide Y to the 5' phosphate of the original DNA fragment, whereas no ligation occurs between the 5' end of the polynucleotide V and the 3' end of the primer-extension product. Optionally, the replicated DNA strand and primer X' is degraded by incubation with dU glycosylase and 95° C. incubation. In some embodiments, the incubation takes place between about 90° C. and 100° C. In further embodiments, the mixture is heated to between about 90° C. and 95° C., or between about 95° C. and 100° C., or is about 90° C., or about 91° C., or about 92° C., or about 93° C., or about 94° C., or about 95° C., or about 96° C., or about 97° C., or about 98° C., or about 99° C., or about 100° C.

Another method of the disclosure for NGS library preparation comprises two sequential tailing and ligation reactions (FIG. 29), wherein the first tailing and ligation reaction is performed in the presence of a polymerase enzyme, a ligase enzyme, nucleotide D (where D=dATP, dTTP or dGTP) and attenuator-adaptor molecule, which is formed by annealing two polynucleotides: polynucleotide X and polynucleotide W(H)n, where polynucleotide X comprises a 5' phosphate, 3' blocking group and NGS adaptor sequence and optional ID tag; and polynucleotide W(H)n which comprises two sequences: 5' sequence W that is complementary to the 5' portion of polynucleotide X and a homopolymeric attenuator sequence (H), where H is A, T or C base, and n=10-30, and additionally comprises a 3' blocking group.

In the reaction, a polymerase enzyme adds a limited number of bases to the 3' end of DNA substrates (1-50 dA or dT bases and 1-50 dG bases), followed by ligation of the first attenuator-adaptor molecule by a ligase enzyme. Following optional heat inactivation of the polymerase and the ligase, addition of a primer containing a 5' sequence X' complementary to sequence X and 1-10 H bases at the 3' end results in primer annealing to the adaptor sequence X and displacement of the attenuator polynucleotide. Additionally, primer X' can comprise an rH blocking base at the 3' end to prevent polymerase-mediated primer tailing with the second tailing and ligation reaction. Addition of a DNA polymerase will extend the primer and replicate the reverse strand of the substrate, where the reaction is optionally stopped by EDTA and purified by magnetic bead-based DNA purification before a second addition of polymerase enzyme adds a limited number of bases to the 3' end of DNA extension product (1-50 dA or dT bases and 1-50 dG bases) in the presence of the second attenuator that is annealed to a second NGS adaptor Y, followed by ligation of the second attenuator-adaptor molecule comprising the second NGS adaptor Y by a ligase enzyme. Optionally, the polymerase and the ligase are heat inactivated, followed by magnetic bead based DNA purification. As above, and in further embodiments, the number of bases added by the polymerase to the 3' end of a DNA substrate is from about 1 nucleotide and up to about 5, 10, 20, 30, 40 or 50 dA, dT or dG nucleotides, or from about 5 and up to about 10, 15, 20, 30, 40 or 50 dA, dT or dG nucleotides, or from about 10 and up to about 15, 20, 30, 40 or 50 dA, dT or dG nucleotides, or from about 9 to about 12 dA, dT or dG nucleotides, or from about 6 to about 8 dA, dT or dG nucleotides. In additional embodiments, the number of bases added by the polymerase to the 3' end of a DNA substrate is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49 or at least about 50 dA, dT or dG nucleotides. In further embodiments, the number of bases added by the polymerase to the 3' end of a DNA substrate is 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more dA, dT or dG nucleotides.

The disclosure also provides methods for NGS library synthesis using a combination of 5' tailed random primer extension on a substrate polynucleotide followed by controlled tailing and ligation (FIG. 30), where intact or fragmented single stranded nucleic acid is contacted under conditions that allow hybridization to a random primer comprising two domains, a 5' domain X where sequence X comprises in various embodiments an NGS adaptor sequence and optional identification tag and a 3' domain comprising a random sequence n, thereby enabling primer hybridization to any region within a nucleic acid sample, and in the presence of a polymerase and nucleotides under appropriate reaction conditions, primer extension and incorporation of adaptor X at the 5' terminus of the extension products is achieved. The primer is various aspects comprise a 5' label, including but not limited to biotin. Following an optional purification or nucleotide degradation step, tailing and ligation reactions are performed on the extension product in the presence of a polymerase, a ligase enzyme, nucleotide D (where D=A, T or G) and an attenuator-adaptor molecule that is formed by annealing two polynucleotides: polynucleotide Y and polynucleotide V(H). Polynucleotide Y comprises a 5' phosphate and a 3' blocking group, where sequence Y comprises a second NGS library adaptor sequence and optional identification tag. Polynucleotide V(H), consists of two sequences: a 5' sequence V that is complementary to the 5' portion of polynucleotide Y and a homopolymeric attenuator sequence (H)11 where H is A, T or C base, and n=10-30, and additionally comprises a 3' blocking group. In the reaction, the polymerase enzyme adds a limited number of bases (i.e., from about 1 to about 50 nucleotides) to the 3' end of primer extension products followed by ligation of the Y/V(H)n attenuator-adaptor molecule by a ligase enzyme, thus completing the addition of both the first and second NGS adaptors.

The disclosure also contemplates a method of targeted NGS library synthesis using a combination of 5' tailed target-specific primer extension on a substrate polynucleotide followed by controlled tailing and ligation (FIG. 31), where intact or fragmented single stranded nucleic acid is subject to hybridization by an plurality of target-specific primers comprising two domains, a 5' domain X common to all primers of the plurality where sequence X comprises an NGS adaptor sequence and optional identification tag, and a 3' domain unique to each primer of the plurality, each comprising a target-specific sequence, thereby enabling primer hybridization to any desired plurality of targets within a nucleic acid sample, and in the presence of a polymerase and nucleotides under appropriate reaction conditions, primer extension and incorporation of adaptor X at the 5' terminus of the extension products is achieved. The primer plurality can additionally comprise a 5' label including but not limited to biotin. Following an optional purification or nucleotide degradation step, tailing and ligation reactions are performed in the presence of a polymerase enzyme, a ligase enzyme, nucleotide D (where D=A, T or G) and an attenuator-adaptor molecule that is formed by annealing two polynucleotides: polynucleotide Y and polynucleotide V(H)$_n$. Polynucleotide Y comprises a 5' phosphate and a 3' blocking group, where sequence Y comprises a second NGS library adaptor sequence and optional identification tag. Polynucleotide $V(H)_n$ consists of two sequences: a 5' sequence V that is complementary to the 5' portion of polynucleotide Y and a homopolymeric attenuator sequence $(H)_n$ where H is A, T or C base, and n=10-30, and additionally comprises a 3' blocking group. In the reaction, the polymerase enzyme adds a limited number of bases (i.e., from about 1 to about 50 nucleotides) to the 3' end of primer extension products followed by ligation of the $Y/V(H)_n$ attenuator-adaptor molecule by a ligase enzyme, thus completing the addition of both NGS adaptors on each target in the plurality.

Also contemplated is a method of targeted NGS library synthesis comprising controlled homopolymer tailing and ligation followed by target-specific primer extension and target-specific blunt adaptor ligation (FIG. 32), wherein tailing and ligation are performed in the presence of a polymerase, a ligase, nucleotide D (where D=A, T or G) and an attenuator-adaptor molecule that is formed by annealing two polynucleotides: polynucleotide X and polynucleotide $W(H)_n$. Polynucleotide X comprises a 5' phosphate and a 3' blocking group, where sequence X comprises an NGS library adaptor sequence and optional identification tag. Polynucleotide $W(H)_n$ comprises two sequences: a 5' sequence W that is complementary to the 5' portion of polynucleotide X and a homopolymeric attenuator sequence $(H)_n$ where H is A, T or C base, and n=10-30, and additionally comprises a 3' blocking group. In the reaction, the polymerase adds a limited number of bases (i.e., from about 1 to about 50 nucleotides) to the 3' end of nucleic acid substrates followed by ligation of the attenuator-adaptor molecule by a ligase. Following optional heat inactivation of the polymerase and ligase, addition of a polymerase, nucleotides and plurality of target-specific primers under appropriate reaction conditions leads to formation of either a double-stranded blunt end (in the presence of proofreading DNA polymerase) or double-stranded end with 3' dA base (in the case when DNA polymerase lacks the proofreading activity) for fragments comprising a complementary sequence to the plurality of target-specific primers. The primer plurality can additionally comprise a 5' label including but not limited to biotin. Ligation of a blunt-end or dT-adaptor to the plurality of target specific products is achieved by a ligase enzyme, wherein the adaptor to be ligated is formed by two polynucleotides: polynucleotide Y, where Y is a second NGS adaptor and polynucleotide V that is complementary to the 3' portion of polynucleotide Y. The 3' end of polynucleotide V has a phosphate blocking group. Ligation results in covalent attachment of the 3' end of polynucleotide Y to the 5' phosphate of the plurality of target-specific fragments, whereas no ligation is formed between the 5' end of polynucleotide V and the 3' end of the target specific primer-extension products. Optionally the completed plurality of target-specific library products are amplified by PCR using NGS adaptor-specific primers.

In FIG. 33, a summary of target-specific NGS library preparation methods involving a controlled tailing and ligation step are depicted. Method 1 summarizes the method described in FIG. 32 with optional targeted library bead capture in Method 2. Method 3 summarizes a method in which a whole genome NGS library is constructed and then followed by target-specific primer extension and targeted library bead capture and amplification. Methods 4 and 5 depict alternate workflows to the method presented in FIG. 31. In Method 4, a plurality of biotinylated target-specific primers extend select regions from a fragmented nucleic acid sample, followed by blunt or TA ligation of the first NGS adaptor, bead capture, then controlled tailing and ligation to add the second NGS adaptor. Method 5 is similar to 4 except that in the first step target-specific primers comprise 5' tails with an NGS adaptor sequence. In Method 6, following controlled tailing and ligation to introduce a first NGS adaptor and adaptor-specific primer extension, denaturation followed by second NGS adaptor 5' tailed target-specific primer extension completes the NGS library that can be further amplified. In any of the methods for target-specific NGS library preparation, it is contemplated that use of the attenuator molecules described herein enables one to multiplex. In additional embodiments, use of the attenuator molecules described herein enables one to immobilize the library products to a surface.

For any of the various embodiments of whole genome or targeted library construction using the disclosed method of controlled tailing and ligation to introduce an NGS adaptor sequence, a second adaptor sequence is introduced by either a second controlled tailing and ligation or is introduced by blunt or TA ligation to a double-stranded substrate following a primer extension reaction. As shown in FIG. 37, various methods are contemplated for blunt and TA adaptor ligation that either ligate one strand selectively or ligates both strands. Thus, the adaptor sequence comprises, in various embodiments, a blunt end or a T-overhanging end (thus allowing TA ligation to occur). In additional embodiments, the adaptor sequence can be blunt-ended, have a T-base 3'-overhang, 5'-phosphate, or 3'-group blocking ligation (for example and without limitation, a dideoxynucleotide) or a combination thereof.

The disclosure further provides a method of extending a substrate polynucleotide comprising: (1) incubating a mixture comprising the substrate polynucleotide with (i) a polymerase enzyme; (ii) a composition comprising an attenuator molecule comprising an attenuator sequence and further comprises a sequence W positioned adjacent the attenuator sequence and is complementary to an adaptor sequence X on a separate polynucleotide; the composition further comprising an adaptor molecule comprising a sequence Y complementary to a sequence V, wherein sequence V is the same length as Y or is less than the same length as sequence Y, the adaptor molecule being a separate molecule from the attenuator-adaptor molecule; and (iii) deoxynucleotides that are complementary to the attenuator sequence of the attenuator molecule, under conditions that allow extension of the substrate polynucleotide to tail the substrate; (2) ligating the adaptor sequence X to the substrate polynucleotide and dissociating the attenuator molecule from the separate polynucleotide; (3) adding a primer complementary to a sequence in the substrate polynucleotide under conditions wherein the primer hybridizes to the substrate polynucleotide; (4) adding a polymerase and deoxynucleotides to perform polymerase extension from the primer to produce a second strand polynucleotide complementary to the substrate polynucleotide and create a double stranded substrate molecule; (5) ligating the adaptor molecule to the double stranded substrate molecule; (6) optionally degrading the second strand polynucleotide. In some embodiments, the primer is sufficiently complementary to a sequence in the substrate polynucleotide to hybridize under appropriate conditions to sequence X. In further embodiments, the primer is a target-specific primer sufficiently complementary to hybridize under appropriate conditions to a sequence in the substrate molecule other than sequence X. In additional embodiments, the substrate polynucleotide is a single strand DNA polynucleotide, and in still further embodiments the substrate polynucleotide is a ribonucleic acid (RNA).

A kit comprising any of the compositions disclosed herein is also provided.

BRIEF DESCRIPTION OF THE FIGURES

FIG. 1 discloses SEQ ID NOs 62, 62, 63 and 62, respectively, in order of appearance.

FIG. 2 discloses SEQ ID NOs 64, 65, 64, 66, 64, 67, 64, 68, 64 and 64, respectively, in order of appearance.

FIG. 4 depicts a method wherein attenuated polymerase-mediated poly(dA) tailing is performed with degradable attenuator polynucleotide containing dU bases. The Figure exemplifies, without limitation, using TdT enzyme for the tailing reaction. FIG. 4 discloses SEQ ID NOs 69, 66, 70 and 66, respectively, in order of appearance.

FIG. 5 discloses SEQ ID NOs 68, 64, 68, 22, 22, 71 and 71, respectively, in order of appearance.

FIG. 6 discloses SEQ ID NOs 25, 64, 25 and 64, respectively, in order of appearance.

FIG. 7 discloses SEQ ID NOs 62, 62, 73 and 62, respectively, in order of appearance.

FIG. 8 depicts attenuated poly (U)-polymerase-mediated poly (rU) tailing of RNA substrates using complementary DNA poly (dA)$_{30}$ polynucleotide. polynucleotide (SEQ ID NO: 68). FIG. 8 discloses SEQ ID NOs 68, 68, 72 and 68, respectively, in order of appearance.

FIG. 15 discloses SEQ ID NOs 86 and 74-76, respectively, in order of appearance.

FIG. 16A shows the effect of attenuator length and reaction temperature. FIG. 16B shows the effect of long incubation time with short attenuator. FIGS. 16A-B disclose SEQ ID NOs 74-76, 86, 77, 78, 68 and 75, respectively, in order of appearance.

FIG. 17 discloses SEQ ID NOs 86 and 79, respectively, in order of appearance.

FIG. 18 discloses SEQ ID NO: 86.

FIG. 21A shows a time course in the presence of short DNA attenuator. FIG. 21B shows the effect of long DNA and RNA attenuators. FIG. 21C shows the effect of long RNA oligonucleotide attenuator.

FIG. 24A shows the process of simultaneous controlled tailing, ligation and immobilization of a single-stranded DNA with attenuator-adaptor complex in solution (DNA). FIG. 24A discloses SEQ ID NOs 2, 27, 26, 80, 27, 26, 81, 82 and 26, respectively, in order of appearance. FIG. 24B shows the process of simultaneous controlled tailing, ligation and immobilization of a single-stranded DNA with attenuator-adaptor complex immobilized to magnetic beads (DNA). FIG. 24B discloses SEQ ID NOs 2, 27, 26, 80, 27, 26, 82, 26, 27 and 26, respectively, in order of appearance. FIG. 24C shows the process of simultaneous controlled tailing, ligation and immobilization of a single-stranded RNA with attenuator-adaptor complex in solution (RNA). FIG. 24C discloses SEQ ID NOs 13, 28, 29, 83, 28, 29, 87, 84 and 29, respectively, in order of appearance. FIGS. 24A-B exemplify, without limitation, using TdT enzyme for the tailing reaction.

DETAILED DESCRIPTION OF THE INVENTION

Figure 1:
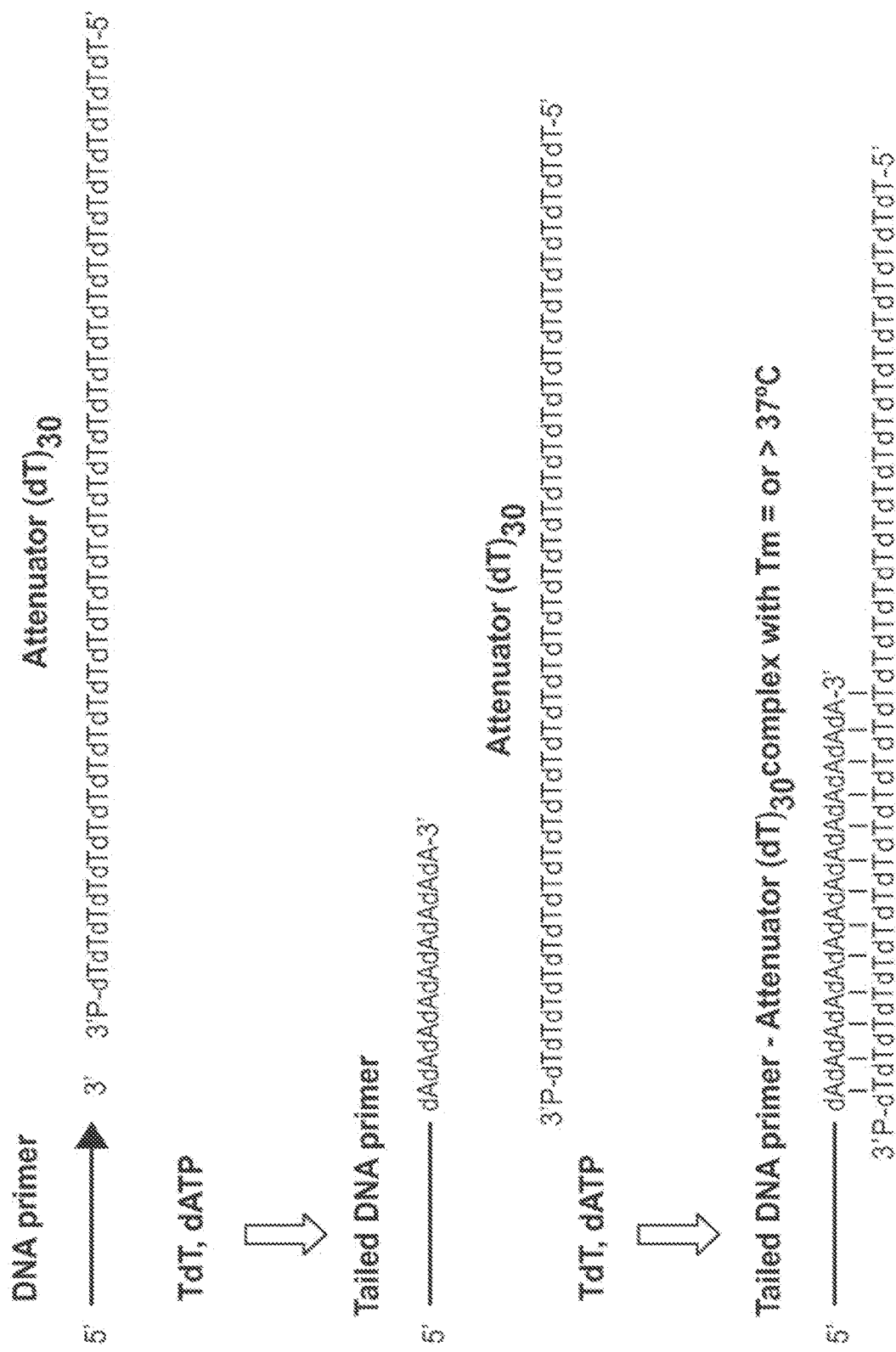
FIG. 1 depicts attenuated, polymerase-mediated poly(dA) DNA tailing in the presence of long (>20b) complementary poly(dT) polynucleotide. The Figure exemplifies, without limitation, using TdT enzyme for the tailing reaction.

Provided herein is a composition comprising a nucleic acid polymerase and an attenuator molecule. The composition is used in a method for adding one or more nucleotides to a substrate polynucleotide in a controlled manner, thereby adding a desired number of nucleotides to the substrate polynucleotide. By way of example and without limitation, elongation of a strand of a polynucleotide using a nucleic acid polymerase is regulated by addition to the elongation reaction mixture of an attenuator molecule that binds to a newly added tail sequence created by the polymerase, thereby forming a duplex structure and thus reducing the rate of the polymerization process. As a result, the reaction rate is controlled and tail sequences of a desired, limited size are added to substrate polynucleotides in the reaction mixture and the tails added to the substrate polynucleotides in the reaction mixture have a very narrow size-distribution.

The disclosure provides methods and reagents that allow the attenuation and control of addition of a tail sequence to the end of a substrate polynucleotide by nucleic acid polymerases. The disclosure also provides compositions for the reactions which are used as a basis for methods, and kits designed to carry out the methods, for size-controlled tailing of a substrate polynucleotide with addition of a tail sequence as described herein using a nucleic acid polymerase. The compositions, and methods, and kits for carrying out the methods, provide for efficient and controlled attachment of a tail sequence to the substrate polynucleotide.

The term "tailing" as used herein is interchangeable with the terms "controlled tailing" and "limited tailing."

It is noted here that, as used in this specification and the appended claims, the singular forms "a," "an," and "the" include plural reference unless the context clearly dictates otherwise.

It is also noted that the term "about" as used herein is understood to mean approximately. "Destabilize," when referring to a molecule of the disclosure (for example and without limitation, an attenuator molecule), means to be rendered susceptible to breakage. Breakage occurs via, for example and without limitation, incubating the molecule at high temperature (about 80° C. or higher), incubating the molecule with an apurinic/apyrimidinic endonuclease or combinations thereof.

Nucleic Acid Polymerases

The disclosure contemplates a composition comprising an attenuator molecule and a nucleic acid polymerase. Methods of the disclosure also include those that utilize additional nucleic acid polymerases. Any polymerase that can add a specific homopolymeric sequence to the 3' end of a nucleic acid is contemplated for use in the methods described herein.

In some aspects, the nucleic acid polymerase is a DNA polymerase, and in one specific aspect the DNA polymerase is terminal deoxynucleotidyl transferase (TdT). It is also contemplated that the nucleic acid polymerase is a RNA polymerase, and in these aspects the RNA polymerase is selected from the group consisting of poly(A) polymerase and poly(U) polymerase. In one specific aspect the RNA polymerase is RNA-specific ribonucleotidyl transferase. These polymerases all represent a family a template-independent polymerases.

To the extent that an enzyme can add a specific homopolymeric sequence to the 3' end of a nucleic acid, non-limiting examples of enzymes that may be used to practice the present invention include but are not limited to terminal deoxynucleotidyl transferase (TdT), E. coli Poly(A) Polymerase, S. pombe poly(U) Polymerase and yeast poly(A) Polymerase. Addition of a repetitive sequence to the 3' end of a substrate can be performed by a DNA telomerase.

Other polymerases that may be used to practice the methods disclosed herein include but are not limited to Deep VentR™ DNA Polymerase, LongAmp™ Taq DNA Polymerase, Phusion™ High-Fidelity DNA Polymerase, Phusion™ Hot Start High-Fidelity DNA Polymerase, VentR® DNA Polymerase, DyNAzyme™ II Hot Start DNA Polymerase, Phire™ Hot Start DNA Polymerase, Crimson LongAmp™ Taq DNA Polymerase, DyNAzyme™ EXT DNA Polymerase, LongAmp™m Taq DNA Polymerase, Taq DNA Polymerase with Standard Taq (Mg-free) Buffer, Taq DNA Polymerase with Standard Taq Buffer, Taq DNA Polymerase with ThermoPol II (Mg-free) Buffer, Taq DNA Polymerase with ThermoPol Buffer, Crimson Taq™ DNA Polymerase, Crimson Taq™ DNA Polymerase with (Mg-free) Buffer, VentR® (exo-) DNA Polymerase, Hemo KlenTaq™, Deep VentR™ (exo-) DNA Polymerase, ProtoScript® AMV First Strand cDNA Synthesis Kit, ProtoScript® M-MuLV First Strand cDNA Synthesis Kit, Bst DNA Polymerase, Full Length, Bst DNA Polymerase, Large Fragment, Taq DNA Polymerase with ThermoPol Buffer, 9° Nm DNA Polymerase, Crimson Taq™ DNA Polymerase, Crimson Taq™ DNA Polymerase with (Mg-free) Buffer, Deep VentR™ (exo-) DNA Polymerase, Deep VentR™ DNA Polymerase, DyNAzyme™ EXT DNA Polymerase, DyNAzyme™ II Hot Start DNA Polymerase, Hemo KlenTaq™, Phusion™ High-Fidelity DNA Polymerase, Phusion™ Hot Start High-Fidelity DNA Polymerase, Sulfolobus DNA Polymerase IV, Therminator™y DNA Polymerase, Therminator™ DNA Polymerase, Therminator™ II DNA Polymerase, Therminator™ III DNA Polymerase, VentR® DNA Polymerase, VentR® (exo-) DNA Polymerase, Bst DNA Polymerase, Large Fragment, DNA Polymerase I (*E. coli*), DNA Polymerase I, Large (Klenow) Fragment, Klenow Fragment (3'→5-exo-), phi29 DNA Polymerase, T4 DNA Polymerase, T7 DNA Polymerase (unmodified), Reverse Transcriptases and RNA Polymerases, AMV Reverse Transcriptase, M-MuLV Reverse Transcriptase, phi6 RNA Polymerase (RdRP), SP6 RNA Polymerase, and T7 RNA Polymerase.

Ligases that may be used to practice the methods of the disclosure include but are not limited to T4 DNA ligase, T4 RNA ligase, *E. coli* DNA ligase and *E. coli* RNA ligase.

Attenuator Molecule

The present disclosure provides compositions and methods that comprise an attenuator molecule (used interchangeably herein with "attenuator polynucleotide"). The attenuator is, in various aspects, a polynucleotide, an immobilized molecule, a polypeptide, a polysaccharide, a linear molecule, a circular molecule, a single stranded molecule, a partially double stranded molecule, a peptide nucleic acid, a Schizophyllan polysaccharide, a locked nucleic acid and/or combinations thereof.

The number of nucleotides added to a substrate polynucleotide is dependent on the conditions under which the reaction is performed. In some aspects, an attenuator molecule is a polynucleotide that hybridizes to a sequence added to a substrate polynucleotide with polymerase activity in the composition, wherein the number of nucleotides added to the substrate polynucleotide is essentially equal to the number of nucleotides in the attenuator molecule with which the tail sequence can associate. In some aspects, the number of nucleotides added to the substrate polynucleotide is essentially equal to a multiple of the number of nucleotides in the attenuator molecule with which the tail sequence can associate. By way of example and without limitation, if the length of an attenuator molecule is 13 nucleotides, then the number of nucleotides that are added to the substrate polynucleotide is essentially 13 nucleotides. Depending on the conditions under which the reaction is performed, however, the number of nucleotides that are added to the substrate polynucleotide is a multiple of 13, or essentially 26 (two times the length of the attenuator molecule), or essentially 39 (three times the length of the attenuator molecule), or essentially 52 (four times the length of the attenuator molecule) or more multiples of the length of the attenuator molecule. In some aspects, therefore, the tail sequence of the substrate polynucleotide interacts with more than one attenuator molecule. In some aspects, the number of nucleotides added to a tail of the substrate polynucleotide is less than the length of the attenuator molecule.

In some aspects, the number of nucleotides added to the substrate polynucleotide is determined not by the length of attenuator but by the temperature and/or salt concentration at which the reaction is performed. In some aspects, a higher temperature and a lower salt concentration will result in more nucleotides being added to the tail of the substrate polynucleotide. It is contemplated that the number of nucleotides added to the tail of the substrate polynucleotide will increase until a certain number is reached, the number being determined by the conditions (i.e., temperature and/or salt concentration) at which a stable duplex is formed between the substrate polynucleotide and the attenuator molecule. Formation of a stable duplex with the attenuator molecule inhibits further addition of nucleotides to the tail of the substrate polynucleotide, and thus it is the $T_m$ of the stable duplex that dictates the number of nucleotides that are added to the tail of the substrate polynucleotide.

In further embodiments, an attenuator molecule further comprises an adaptor sequence as described herein below. In aspects wherein the attenuator molecule is a polynucleotide, it is contemplated that the homopolymeric portion of the polynucleotide is the "attenuator" portion. In aspects wherein the polynucleotide comprises nucleotides in addition to the homopolymeric sequence, the polynucleotide is referred to herein as an "attenuator-adaptor" molecule. The additional nucleotides can be part of the same polynucleotide, or can be present in two separate polynucleotides that are hybridized to each other. Thus, in still further embodiments, the attenuator molecule and the adaptor molecule (which comprises the adaptor sequence) are two separate polynucleotides that are at least partially hybridized together. In various embodiments, a single polynucleotide comprises an attenuator portion and an adaptor sequence. In various aspects, the polynucleotide forms a hairpin structure to create a partially double stranded polynucleotide. In this hairpin configuration, the attenuator portion is single-stranded, and the adaptor sequence is double-stranded.

In additional embodiments, the attenuator or attenuator-adaptor molecule comprises a dinucleotide polymer sequence instead of a homopolymer sequence. Thus, in various embodiments, the disclosure contemplates that the dinucleotide portion of the attenuator comprises a plurality of random sequences comprised of the following dinucleotide combinations: (i) dG or dC; (ii) dA or dT; (iii) dG or dT; (iv) dG or dA; (v) dA or dC; or (vi) dC or dT. The dinucleotide sequences, in various embodiments, comprise mixtures of ribonucleotides and deoxyribonucleotides. In these embodiments, it is further contemplated that the nucleotide mix used for the tailing reactions comprise the complementary nucleotides to those used in the homopolymeric portion of the attenuator. During the tailing process, a plurality of random tail sequences comprised of the dinucleotides complementary to the dinucleotide attenuator are generated. In the disclosure, various embodiments are described with reference to a homopolymer sequence or a homopolymer or dinucleotide sequence. The worker or skill in the art will appreciate, however, that in instances wherein only a homopolymer is described, the method can readily be carried out using a dinucleotide sequence with modifications as described herein.

In still further embodiments, the attenuator or attenuator-adaptor molecule further comprises an additional sequence on its 3' end, wherein the additional sequence is not a homopolymer or a dinucleotide sequence but comprises a random nucleotide sequence which in various aspects, comprises ribonucleotides, deoxyribonucleotides or a combination thereof. The additional random sequence is from about 1 to about 50 nucleotides or more in length, or from about 1 to about 5 nucleotides, or from about 1 to about 10, 20, 30, 40 or 50 nucleotides, or from about 5 to about 10 nucleotides, or from about 4 to about 7 nucleotides, or from about 5 to about 15 nucleotides, or from about 10 to about 15 nucleotides, or from about 10 to about 20, 30, 40 or 50 nucleotides in length, or from about 5 to about 10, 20, 30, 40 or 50 nucleotides, or from about 10 to about 20, 30, 40 or 50 nucleotides in length, or from about 20 to about 30, 40 or 50 nucleotides in length. In further embodiments, the additional sequence is about 1, about 2, about 3, about 4, about 5 about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50 or more nucleotides in length. In still further embodiments, the additional sequence is at least about 1, at least about 2, at least about 3, at least about 4, at least about 5, at least about 6, at least about 7, at least about 8, at least about 9, at least about 10, at least about 11, at least about 12, at least about 13, at least about 14, at least about 15, at least about 16, at least about 17, at least about 18, at least about 19, at least about 20, at least about 21, at least about 22, at least about 23, at least about 24, at least about 25, at least about 26, at least about 27, at least about 28, at least about 29, at least about 30, at least about 31, at least about 32, at least about 33, at least about 34, at least about 35, at least about 36, at least about 37, at least about 38, at least about 39, at least about 40, at least about 41, at least about 42, at least about 43, at least about 44, at least about 45, at least about 46, at least about 47, at least about 48, at least about 49, at least about 50 or more nucleotides in length. In further embodiments, the additional sequence is 1, 2, 3, 4, 5 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more nucleotides in length.

It will be understood that not all of the attenuator or attenuator-adaptor molecules used in a given reaction are uniform in size. Thus, in various embodiments, the homopolymer portion and the additional sequence portion of the attenuator molecule are each from about 1 to about 500 nucleotides in length. In further embodiments, the disclosure contemplates that an attenuator molecule that is a polynucleotide comprises a homopolymer portion and an additional sequence portion, each of which is at least 1 nucleotide and up to about 5, 10, 20, 30, 50, 100, 200, 300 or 500 nucleotides, at least 2 nucleotides and up to about 5, 10, 20, 30, 50, 100, 200, 300 or 500 nucleotides, at least 5 nucleotides and up to about 10, 20, 30, 50, 100, 200, 300 or 500 nucleotides, at least 5 nucleotides and up to about 10, 15, 20, 25, 30, 35, 40, 45 or 50 nucleotides, at least 10 and up to about 15, 20, 25, 30, 35, 40, 45 or 50 nucleotides, at least 10 and up to about 20, 30, 40, 50, 100, 200, 300 or 500 nucleotides, at least 20 and up to about 30, 40, 50, 100, 200, 300 or 500 nucleotides, at least 50 and up to about 70, 100, 200, 300 or 500 nucleotides or at least 50 and up to about 100, 300, 400 or 500 nucleotides.

It is contemplated that "hybridization" as used herein encompasses any association between the attenuator molecule and the tail sequence of the substrate polynucleotide. For example and without limitation, the association can be the result of Watson-Crick base-pairing, or other types of base-pairing between the attenuator molecule and the substrate polynucleotide such as DNA, RNA and peptide nucleic acids (PNA).

In some embodiments, the attenuator molecule is a polynucleotide and it hybridizes to the tail portion of the substrate polynucleotide under stringent conditions. "Stringent conditions" as used herein can be determined empirically by the worker of ordinary skill in the art and will vary based on, for example and without limitation, the length of the attenuator molecule and the tail sequence of the substrate polynucleotide, concentrations of the attenuator molecule and the substrate polynucleotide, the salt concentration (i.e., ionic strength) in the hybridization buffer, the temperature at which the hybridization is carried out, length of time that hybridization is carried out, and presence of factors that affect surface charge of the attenuator molecule and the tail sequence of the substrate polynucleotide. In general, stringent conditions are those in which the tail sequence of the substrate polynucleotide is able to bind to its complementary sequence preferentially and with higher affinity relative to any other region on the attenuator molecule. Exemplary stringent conditions for hybridization to its complement of a tail sequence of a substrate polynucleotide sequence having 20 bases include without limitation about 50 mM salt (Na±), and an annealing temperature of about 60° C. For a longer sequence, specific hybridization is achieved at higher temperature. In general, stringent conditions are such that annealing is carried out about 5° C. below the melting temperature of the substrate polynucleotide. The "melting temperature" is the temperature at which 50% of attenuator molecules that are complementary to a substrate polynucleotide in equilibrium at definite ion strength, pH and concentration, dissociate from the substrate polynucleotide. As described further herein below, the temperature at which the hybridization and extension is performed is, in various aspects, related to the addition of nucleotides to the substrate polynucleotide.

In certain embodiments where the attenuator molecule is a polynucleotide, the attenuator polynucleotide is single stranded or at least partially double stranded inasmuch as the double stranded polynucleotide is able to associate with the tail sequence added to the substrate polynucleotide. In further embodiments, the attenuator molecule is a circular molecule comprising a homopolymeric nucleotide sequence that is able to associate with the tail sequence added to the substrate polynucleotide.

In further embodiments, the attenuator molecule that is a polynucleotide comprises a nucleotide selected from the group consisting of T-deoxythymidine 5'-monophosphate (dTMP), 2'-deoxyguanosine 5'-monophosphate (dGMP), 2'-deoxyadenosine 5'-monophosphate (dAMP), 2'-deoxycytidine 5'-monophosphate (dCMP), 2'-deoxyuridine 5'-monophosphate (dUMP), thymidine monophosphate (TMP), guanosine monophosphate (GMP), adenosine monophosphate (AMP), cytidine monophosphate (CMP), uridine monophosphate (UMP), a base analog, and combinations thereof. It is also contemplated that the attenuator molecule polynucleotide comprises a modified nucleotide as defined herein.

In related aspects, the attenuator molecule comprises a homopolymeric molecule such as poly 2'-deoxyadenosine 5'-monophosphate (dAMP) (poly dA), poly T-deoxythymidine 5'-monophosphate (dTMP) (poly dT), poly 2'-deoxycytidine 5'-monophosphate (poly dC), poly 2'-deoxyguanosine 5'-monophosphate (poly dG), poly 2'-deoxyuridine 5'-monophosphate (poly dU), poly adenosine monophosphate (poly rA), poly uridine monophosphate (poly U), poly cytidine monophosphate (poly rC), poly guanosine monophosphate (poly rG) or a heteropolymeric molecule comprising combinations of dA and rA bases, or dT, dU and U bases, or dC and rC bases, or dG and rG bases.

In various aspects, the attenuator molecule comprises 1, 5, 10, 20, 30, 50, 100 or more nucleotides. Indeed, the disclosure contemplates that an attenuator molecule that is a polynucleotide comprises 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, 100, 110, 120, 130, 140, 150, 160, 170, 180, 190, 200, 210, 220, 230, 240, 250, 260, 270, 280, 290, 300, 310, 320, 330, 340, 350, 360, 370, 380, 390, 400, 410, 420, 430, 440, 450, 460, 470, 480, 490, 500, 510, 520, 530, 540, 550, 560, 570, 580, 590, 600, 610, 620, 630, 640, 650, 660, 670, 680, 690, 700, 710, 720, 730, 740, 750, 760, 770, 780, 790, 800, 810, 820, 830, 840, 850, 860, 870, 880, 890, 900, 910, 920, 930, 940, 950, 960, 970, 980, 990, 1000 or more nucleotides. In further embodiments, the disclosure contemplates that an attenuator molecule that is a polynucleotide comprises at least 1 nucleotide and up to about 5, 10, 20, 50, 100, 200, 500 or 1000 nucleotides, at least 2 nucleotides and up to about 5, 10, 20, 50, 100, 200, 500 or 1000 nucleotides, at least 5 nucleotides and up to about 10, 20, 50, 100, 200, 500 or 1000 nucleotides, at least 5 nucleotides and up to about 10, 15, 20, 25, 30, 35, 40, 45 or 50 nucleotides, at least 10 and up to about 15, 20, 25, 30, 35, 40, 45 or 50 nucleotides, at least 10 and up to about 20, 30, 40, 50, 100, 200, 500 or 1000 nucleotides, at least 20 and up to about 30, 40, 50, 100, 200, 500 or 1000 nucleotides, at least 50 and up to about 70, 100, 200, 500, 700 or 1000 nucleotides or at least 50 and up to about 100, 500, 750, 800 or 1000 nucleotides.

In various aspects the attenuator molecule comprises a blocking group. A blocking group as used herein is a moiety that prevents extension by an enzyme that is capable of synthesizing a polynucleotide by addition of nucleotides. Blocking groups include but are not limited to a phosphate group, a dideoxynucleotide, a ribonucleotide (in aspects wherein a TdT enzyme is used), deoxynucleotides (in aspects wherein a poly(A) and/or a poly(U) polymerase is used), an amino group, a three or six carbon glycol spacer (and in one aspect the six carbon glycol spacer is hexanediol) and an inverted deoxythymidine (dT).

In another aspect of the disclosure, the attenuator molecule is degradable. The degradable attenuator molecule comprises, in various aspects, dU bases and degradation is caused by contact with a dU-glycosylase followed by incubation at a temperature that is above 80° C., or by contact with a mixture of a dU-glycosylase and an apurinic/apyrimidinic endonuclease.

It is also contemplated that the attenuator molecule comprises, in some embodiments, ribonucleotides and has a sequence that is degradable with a ribonuclease. In various aspects, the ribonuclease is selected from the group consisting of RNase H, RNase HII, RNase A, and RNase T1 under conditions sufficient for ribonuclease activity. In a related aspect, the attenuator molecule comprises deoxyribonucleotides and has a sequence that is degradable with a DNA-specific nuclease. The DNA-specific nuclease is, in some aspects, DNase I.

The attenuator molecule, in further embodiments, further comprises an adaptor sequence, an identifier tag sequence, or both. An "adaptor sequence" provides a priming sequence for both amplification and sequencing of nucleic acid fragments and is used, in some aspects, for next generation sequencing applications. In further aspects, an "adaptor sequence" is used as a promoter sequence for generation of RNA molecules, wherein the promoter sequence is, for example and without limitation, a T7 promoter sequence or an SP6 promoter sequence. Any RNA promoter that is known in the art is contemplated as an adaptor sequence.

In some embodiments, the "identifier tag sequence" is a sequence that uniquely identifies a particular substrate or attenuator molecule. In one aspect, the identifier tag sequence is a barcode.

In some aspects the attenuator molecular is a polypeptide. As used herein, the term "polypeptide" refers to peptides, proteins, polymers of amino acids and antibodies that are naturally derived, synthetically produced, or recombinantly produced. Polypeptides also include lipoproteins and post-translationally modified proteins, such as, for example, glycosylated proteins, as well as proteins or protein substances that have D-amino acids, modified, derivatized, or non-naturally occurring amino acids in the D- or L-configuration and/or peptomimetic units as part of their structure.

With regard to proteins, attenuator molecules contemplated include full length protein and fragments thereof which retain the desired property of the full length proteins. Fusion proteins, including fusion proteins wherein one fusion component is a fragment or a mimetic, are also contemplated.

Antibody attenuator molecules include fragments and derivatives of full length antibodies. Specifically contemplated fragments and derivatives include, but are not limited to, Fab' fragments, F(ab)$_2$ fragments, Fv fragments, Fc fragments, one or more complementarity determining regions (CDR) fragments, individual heavy chains, individual light chain, dimeric heavy and light chains (as opposed to heterotetrameric heavy and light chains found in an intact antibody, single chain antibodies (scAb), humanized antibodies (as well as antibodies modified in the manner of humanized antibodies but with the resulting antibody more closely resembling an antibody in a non-human species), chelating recombinant antibodies (CRABs), bispecific antibodies and multispecific antibodies, and other antibody derivative or fragments known in the art.

DNA and RNA binding proteins are contemplated for use in the methods and compositions of the disclosure. DNA-binding proteins are proteins that are comprised of DNA-binding domains and thus have a specific or general affinity for single stranded DNA [Travers, DNA-protein Interactions. Springer, 1993; Pabo et al., Protein-DNA recognition. Annu Rev Biochem. 53: 293-321 (1984)]. Polypeptides that bind to homopolymeric sequences are known in the art [Lobanenkov et al., Eur J Biochem. 159(1): 181-8 (1986); Travers, Annu Rev Biochem, 58: 427-452 (1989); Ostrowski et al., Proc. Natl. Acad. Sci. (USA) 98(16): 9044-9049 (2001)], and contemplated for use herein.

RNA-binding proteins are typically cytoplasmic and nuclear proteins that associate with double strand or single strand RNAs through an RNA recognition motif (RRM). RNA-binding proteins may regulate the translation of RNA, and post-transcriptional events such as, without limitation, RNA splicing and editing. Some examples of RNA binding proteins include, without limitation, translation initiation factors that bind RNA, polyA-binding proteins, snRNPs, and double stranded RNA-specific adenosine deaminase (ADAR).

Another type of attenuator molecule contemplated by the disclosure is polysaccharide Schizophyllan that can form non-Watson-Crick type macromolecular complexes with poly(C), poly(A), poly(dA) and poly(dT) homo-polymers. Schizophyllan (SPG) is a natural 1₃-(1,3)-D-glucan existing as a triple helix in water and as a single chain in dimethylsulfoxide (DMSO), respectively [Matsumoto et al., Biochim Biophys Acta. 1670(2): 91-104 (2004)]. Schizophyllan has glucose side chain through a β-1,6-glycosil bond. It has been shown that Schizophyllan can form a complex with single stranded polynucleotides. In the presence of polynucleotides, single chain SPG in an aqueous solution forms a triple stranded complex that consist of two SPG chains and a polynucleotide chain. Schizophyllan can form a triple stranded complex with a single stranded polynucleotide through hydrogen bonding and hydrophobic interaction. It was shown that the polynucleotide was protected from nuclease attack in forming the complex with Schizophyllan, and Schizophyllan enhanced antisense efficiency [Sakurai et al., Nucleic Acids Research Supplement No. 1: 223-224 (2001)].

Regardless of the type of attenuator molecule, it is contemplated that in some aspects the attenuator molecule is immobilized on a support as described herein below.

Substrate Polynucleotide

A substrate polynucleotide is a polynucleotide, modified polynucleotide or combination thereof as described herein below. The substrate polynucleotide is, in various embodiments, DNA, RNA, or a combination thereof. The substrate polynucleotide to which the tail is added is either single stranded or double stranded. In further aspects, the substrate polynucleotide can be a triple helix, a G-quartet, or other multi-strand structure. In another embodiment, the substrate polynucleotide is chemically treated nucleic acid, including but not limited to embodiments wherein the substrate polynucleotide is bisulfite-treated DNA to detect methylation status by NGS.

It is contemplated that substrate polynucleotides are obtained from naturally occurring sources or they can be synthetic. The naturally occurring sources are RNA and/or genomic DNA from a prokaryote or a eukaryote. For example and without limitation, the source can be a human, mouse, virus, plant or bacteria. In various aspects, the substrate polynucleotide is tailed for use in assays involving microarrays and creating libraries for next generation nucleic acid sequencing. Tailed substrate polynucleotides can also be used for efficient cloning of DNA and RNA.

If the source of the substrate polynucleotide is genomic DNA, it is contemplated that in some embodiments the genomic DNA is fragmented prior to its being tailed. Fragmenting of genomic DNA is a general procedure known to those of skill in the art and is performed, for example and without limitation in vitro by shearing (nebulizing) the DNA, cleaving the DNA with an endonuclease, sonicating the DNA, by heating the DNA, by irradiation of DNA using alpha, beta, gamma or other radioactive sources, by light, by chemical cleavage of DNA in the presence of metal ions, by radical cleavage and combinations thereof. Fragmenting of genomic DNA can also occur in vivo, for example and without limitation due to apoptosis, radiation and/or exposure to asbestos. According to the methods provided herein, a population of substrate polynucleotides are not required to be of a uniform size. Thus, the methods of the disclosure are effective for use with a population of differently-sized substrate polynucleotide fragments.

The substrate polynucleotide, as disclosed herein, is either single stranded or double stranded and comprises a 3' overhang. In some aspects the substrate polynucleotide is double stranded and comprises a blunt end. In other aspects, the double stranded substrate polynucleotide comprises a 3' recessed end. In all aspects, the substrate polynucleotide comprises a free 3' hydroxyl group. The length of an overhang or recessed end of a substrate polynucleotide can be varied. In various aspects, the length of an overhang or recessed end of a substrate polynucleotide is 1, 2, 3, 4, 5, 6, 7, 8, 9, 10 or more nucleotides in length. In specific aspects, a 3' overhang that is 3 nucleotides in length is a more efficient substrate polynucleotide than a 3' overhang that is either 2 nucleotides in length or 1 nucleotide in length. A population of substrate polynucleotides in various aspects, includes those wherein more than one of the above-mentioned types of substrate polynucleotides are present in a single reaction.

In some embodiments, it is contemplated that the substrate polynucleotide is immobilized on a solid surface as described herein below. Immobilization of the substrate polynucleotide results, in one aspect, from its ligation to an attenuator-adaptor molecule as described below.

The length of a substrate polynucleotide is contemplated to be between about 3 and about $1\times10^6$ nucleotides. In some aspects, the length of the substrate polynucleotide is between about 10 and about 3000 nucleotides, or between about 40 and about 2000 nucleotides, or between about 50 and about 1000 nucleotides, or between about 100 and about 500 nucleotides, or between about 1000 and about 5000 nucleotides, or between about 10,000 and 50,000 nucleotides, or between about 100,000 and $1\times10^6$ nucleotides. In further aspects, the length of the substrate polynucleotide is at least 3 and up to about 50, 100 or 1000 nucleotides; or at least 10 and up to about 50, 100 or 1000 nucleotides; or at least 100 and up to about 1000, 5000 or 10000 nucleotides; or at least 1000 and up to about 10000, 20000 and 50000; or at least 10000 and up to about 20000, 50000 and 100,000 nucleotides; or at least 20000 and up to about 100,000, 200,000 or 500,000 nucleotides; or at least 200,000 and up to about 500,000, 700,000 or 1,000,000 nucleotides. In various aspects, the length of the substrate polynucleotide is about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990, about 1000, about 1100, about 1200, about 1300, about 1400, about 1500, about 1600, about 1700, about 1800, about 1900, about 2000, about 2100, about 2200, about 2300, about 2400, about 2500, about 2600, about 2700, about 2800, about 2900, about 3000, about 3100, about 3200, about 3300, about 3400, about 3500, about 3600, about 3700, about 3800, about 3900, about 4000, about 4100, about 4200, about 4300, about 4400, about 4500, about 4600, about 4700, about 4800, about 4900, about 5000, 10,000, 15,000, 20,000, 50,000, 100,000, 150,000, 200,000, 250,000, 300,000, 350,000, 400,000, 450,000, 500,000, 550,000, 600,000, 650,000, 700,000, 750,000, 800,000, 850,000, 900,000, 950,000, 1,000,000 or more nucleotides.

Polynucleotides

The terms "polynucleotide" and "nucleotide" or plural forms as used herein are interchangeable with modified forms as discussed herein and otherwise known in the art. Polynucleotides as described herein refer to either an attenuator polynucleotide or a substrate polynucleotide and comprise, in various embodiments, a deoxyribonucleotide, a ribonucleotide or a combination thereof. In further embodiments, an attenuator polynucleotide that comprises a ribonucleotide, a deoxyribonucleotide, or a combination thereof, is used in combination with a substrate polynucleotide that is either DNA or RNA.

In certain instances, the art uses the term "nucleobase" which embraces naturally-occurring nucleotides as well as modifications of nucleotides that can be polymerized. Thus, nucleotide or nucleobase means the naturally occurring nucleobases adenine (A), guanine (G), cytosine (C), thymine (T) and uracil (U) as well as non-naturally occurring nucleobases such as xanthine, diaminopurine, 8-oxo-N6-methyladenine, 7-deazaxanthine, 7-deazaguanine, N4,N4-ethanocytosin, N',N'-ethano-2,6-diaminopurine, 5-methylcytosine (mC), 5-(C3-C6)-alkynyl¬cytosine, 5-fluorouracil, 5-bromouracil, pseudoisocytosine, 2-hydroxy-5-methyl-4-tr¬iazolopyridin, isocytosine, isoguanine, inosine and the "non-naturally occurring" nucleobases described in Benner et al., U.S. Pat. No. 5,432,272 and Susan M. Freier and Karl-Heinz Altmann, 1997, Nucleic Acids Research, vol. 25: pp 4429-4443. The term "nucleobase" also includes not only the known purine and pyrimidine heterocycles, but also heterocyclic analogues and tautomers thereof. Further naturally and non-naturally occurring nucleobases include those disclosed in U.S. Pat. No. 3,687,808 (Merigan, et al.), in Chapter 15 by Sanghvi, in Antisense Research and Application, Ed. S. T. Crooke and B. Lebleu, CRC Press, 1993, in Englisch et al., 1991, Angewandte Chemie, International Edition, 30: 613-722 (see especially pages 622 and 623, and in the Concise Encyclopedia of Polymer Science and Engineering, J. I. Kroschwitz Ed., John Wiley & Sons, 1990, pages 858-859, Cook, Anti-Cancer Drug Design 1991, 6, 585-607, each of which are hereby incorporated by reference in their entirety). In various aspects, polynucleotides also include one or more "nucleosidic bases" or "base units" which include compounds such as heterocyclic compounds that can serve like nucleobases, including certain "universal bases" that are not nucleosidic bases in the most classical sense but serve as nucleosidic bases. Universal bases include 3-nitropyrrole, optionally substituted indoles (e.g., 5-nitroindole), and optionally substituted hypoxanthine. Other desirable universal bases include, pyrrole, diazole or triazole derivatives, including those universal bases known in the art.

Polynucleotides may also include modified nucleobases. A "modified base" is understood in the art to be one that can pair with a natural base (e.g., adenine, guanine, cytosine, uracil, and/or thymine) and/or can pair with a non-naturally occurring base. Exemplary modified bases are described in EP 1 072 679 and WO 97/12896, the disclosures of which are incorporated herein by reference. Modified nucleobases include without limitation, 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine. Further modified bases include tricyclic pyrimidines such as phenoxazine cytidine (1H-pyrimido[5,4-b][1,4]benzoxazin-2(3H)-one), phenothiazine cytidine (1H-pyrimido[5,4-b][1,4]benzothiazin-2(3H)-one), G-clamps such as a substituted phenoxazine cytidine (e.g. 9-(2-aminoethoxy)-H-pyrimido[5,4-b][1,4]benzoxazin-2(3H)-one), carbazole cytidine (2H-pyrimido[4,5-b]indol-2-one), pyridoindole cytidine (H-pyrido[3',2':4,5]pyrrolo[2,3-d]pyrimidin-2-one). Modified bases may also include those in which the purine or pyrimidine base is replaced with other heterocycles, for example 7-deazaadenine, 7-deazaguanosine, 2-aminopyridine and 2-pyridone. Additional nucleobases include those disclosed in U.S. Pat. No. 3,687,808, those disclosed in The Concise Encyclopedia Of Polymer Science And Engineering, pages 858-859, Kroschwitz, J. I., ed. John Wiley & Sons, 1990, those disclosed by Englisch et al., 1991, Angewandte Chemie, International Edition, 30: 613, and those disclosed by Sanghvi, Y. S., Chapter 15, Antisense Research and Applications, pages 289¬302, Crooke, S. T. and Lebleu, B., ed., CRC Press, 1993. Certain of these bases are useful for increasing the binding affinity and include 5-substituted pyrimidines, 6-azapyrimidines and N-2, N-6 and 0-6 substituted purines, including 2-aminopropyladenine, 5-propynyluracil and 5-propynylcytosine. 5-methylcytosine substitutions have been shown to increase nucleic acid duplex stability by 0.6-1.2° C. and are, in certain aspects combined with 2'-O-methoxyethyl sugar modifications. See, U.S. Pat. Nos. 3,687,808, 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; 5,645,985; 5,830,653; 5,763,588; 6,005,096; 5,750,692 and 5,681,941, the disclosures of which are incorporated herein by reference.

Methods of making polynucleotides of a predetermined sequence are well-known. See, e.g., Sambrook et al., Molecular Cloning: A Laboratory Manual (2nd ed. 1989) and F. Eckstein (ed.) Oligonucleotides and Analogues, 1st Ed. (Oxford University Press, New York, 1991). Solid-phase synthesis methods are preferred for both polyribonucleotides and polydeoxyribonucleotides (the well-known methods of synthesizing DNA are also useful for synthesizing RNA). Polyribonucleotides can also be prepared enzymatically. Non-naturally occurring nucleobases can be incorporated into the polynucleotide, as well. See, e.g., U.S. Pat. No. 7,223,833; Katz, J. Am. Chem. Soc., 74:2238 (1951); Yamane, et al., J. Am. Chem. Soc., 83:2599 (1961); Kosturko, et al., Biochemistry, 13:3949 (1974); Thomas, J. Am. Chem. Soc., 76:6032 (1954); Zhang, et al., J. Am. Chem. Soc., 127:74-75 (2005); and Zimmermann, et al., J. Am. Chem. Soc., 124:13684-13685 (2002).

Modified Polynucleotides

Modified polynucleotides are contemplated for use in an attenuator molecule or in a substrate polynucleotide wherein both one or more sugar and/or one or more internucleotide linkage of the nucleotide units in the polynucleotide is replaced with "non-naturally occurring" groups. In one aspect, this embodiment contemplates a peptide nucleic acid (PNA). In PNA compounds, the sugar-backbone of a polynucleotide is replaced with an amide containing backbone. See, for example U.S. Pat. Nos. 5,539,082; 5,714,331; and 5,719,262, and Nielsen et al., Science, 1991, 254, 1497-1500, the disclosures of which are herein incorporated by reference.

Other linkages between nucleotides and unnatural nucleotides contemplated for the disclosed polynucleotides include those described in U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920; U.S. Patent Publication No. 20040219565; International Patent Publication Nos. WO 98/39352 and WO 99/14226; Mesmaeker et. al., Current Opinion in Structural Biology 5:343-355 (1995) and Susan M. Freier and Karl-Heinz Altmann, Nucleic Acids Research, 25:4429-4443 (1997), the disclosures of which are incorporated herein by reference.

Specific examples of polynucleotides include those containing modified backbones or non-natural internucleoside linkages. Polynucleotides having modified backbones include those that retain a phosphorus atom in the backbone and those that do not have a phosphorus atom in the backbone. Modified polynucleotides that do not have a phosphorus atom in their internucleoside backbone are considered to be within the meaning of "polynucleotide."

Modified polynucleotide backbones containing a phosphorus atom include, for example, phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage. Also contemplated are polynucleotides having inverted polarity comprising a single 3' to 3' linkage at the 3'-most internucleotide linkage, i.e. a single inverted nucleoside residue which may be abasic (the nucleotide is missing or has a hydroxyl group in place thereof). Salts, mixed salts and free acid forms are also contemplated.

Representative United States patents that teach the preparation of the above phosphorus-containing linkages include, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; 5,194,599; 5,565,555; 5,527,899; 5,721,218; 5,672,697 and 5,625,050, the disclosures of which are incorporated by reference herein.

Modified polynucleotide backbones that do not include a phosphorus atom have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; and others having mixed N, O, S and $CH_2$ component parts. In still other embodiments, polynucleotides are provided with phosphorothioate backbones and oligonucleosides with heteroatom backbones, and including —$CH_2$—NH—O—$CH_2$—, —$CH_2$—N($CH_3$)—O—$CH_2$— CH2-O—N($CH_3$)—$CH_2$—, —$CH_2$—N($CH_3$)—N($CH_3$)— $CH_2$— and —O—N($CH_3$)—$CH_2$—$CH_2$— described in U.S. Pat. Nos. 5,489,677, and 5,602,240. See, for example, U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; 5,792,608; 5,646,269 and 5,677,439, the disclosures of which are incorporated herein by reference in their entireties.

In various forms, the linkage between two successive monomers in the polynucleotide consists of 2 to 4, desirably 3, groups/atoms selected from —$CH_2$—, —O—, —S—, —NRH—, >C=O, >C=NRH, >C=S, —Si(R")$_2$—, —SO—, —S(O)$_2$—, —P(O)$_2$—, —PO($BH_3$)—, —P(O,S)—, —P(S)$_2$—, —PO(R")—, —PO($OCH_3$)—, and —PO(NHRH)—, where RH is selected from hydrogen and C1-4-alkyl, and R" is selected from C1-6-alkyl and phenyl. Illustrative examples of such linkages are —$CH_2$—$CH_2$—$CH_2$—, —CO—$CH_2$—CHOH—$CH_2$—, —O—$CH_2$—O—, —O—$CH_2$—$CH_2$—CH= (including R5 when used as a linkage to a succeeding monomer), —$CH_2$—$CH_2$—O—, —NRH—$CH_2$—$CH_2$—, —$CH_2$—$CH_2$—NRH—, —$CH_2$—NRH—$CH_2$—O—$CH_2$—$CH_2$—NRH—, —NRH—CO—O—, —NRH—CO—NRH—, —NRH—CS—NRH—, —NRH—C(=NRH)—NRH—, —NRH—CO—$CH_2$—NRH—O—CO—O—, —O—CO—CH2-O—, —O—$CH_2$—CO—O—, —$CH_2$—CO—NRH—, —O—CO—NRH—, —NRH—CO—$CH_2$—, —O—$CH_2$—CO—NRH—, —O—$CH_2$—$CH_2$—NRH—, —CH=N—O—, —CH2-NRH—O—, —$CH_2$—O—N= (including R5 when used as a linkage to a succeeding monomer), —$CH_2$—O—NRH—, —CO—NRH—$CH_2$—, —$CH_2$—NRH—O—, —$CH_2$—NRH—CO—, —O—NRH—$CH_2$—, —C—NRH, —O—$CH_2$—S—, —S—$CH_2$—O—, —$CH_2$—$CH_2$—S—, —O—$CH_2CH_2$—S—, —S—$CH_2$—CH= (including R5 when used as a linkage to a succeeding monomer), —S—$CH_2$—$CH_2$—, —S—$CH_2$—$CH_2$—O—, —S—$CH_2$—$CH_2$—S—, —$CH_2$—S—$CH_2$—, $CH_2$—SO—$CH_2$—, —$CH_2$—$SO_2$—$CH_2$—, —O—SO—O—, —O—S(O)$_2$—O—, —OS(O)2-$CH_2$—, —O—S(O)$_2$—NRH—, —NRH—S(O)$_2$—$CH_2$—; —O—S(O)$_2$—$CH_2$—, O—P(O)$_2$—O—, —O—P(O,S)—O—, —S—P(O,S)—O—, —S—P(S)$_2$—O—, —O—P(O)$_2$—S—, —O—P(O,S)—S—, —S—P(O)$_2$—S—, —S—P(O,S)—S—, —S—P(S)$_2$—S—, —O—PO(R")—O—, —O—PO($OCH_2$)—O—, —O—PO($OCH_2CH_3$)—O—, —O—PO($OCH_2CH_2$S—R)—O—, —O—PO($BH_3$)—O—, —O—PO(NHRN)—O—, —O—P(O)$_2$—NRHH—, —NRH—P(O)$_2$—O—, —O—P(O,NRH)—O—, —$CH_2$—P(O)$_2$—O—, —O—P(O)$_2$—$CH_2$—, and —O—Si(R")$_2$—O—; among which CH$_2$—CO—NRH—, —CH$_2$—NRH—O—, —S—CH2-O—, —O—P(O)$_2$—O—O—P(—O,S)—O—, —NRHP(O)$_2$ —O—, —O—P(O,NRH)—O—, —O—PO(R")—O—, —O—PO(CH$_3$)—O—, and —O—PO(NHRN)—O—, where RH is selected form hydrogen and C1-4-alkyl, and R" is selected from C1-6-alkyl and phenyl, are contemplated. Further illustrative examples are given in Mesmaeker et. al., 1995, Current Opinion in Structural Biology, 5: 343-355 and Susan M. Freier and Karl-Heinz Altmann, 1997, Nucleic Acids Research, vol 25: pp 4429-4443.

Still other modified forms of polynucleotides are described in detail in U.S. Patent Application No. 20040219565, the disclosure of which is incorporated by reference herein in its entirety.

Modified polynucleotides may also contain one or more substituted sugar moieties. In certain aspects, polynucleotides comprise one of the following at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C$_1$ to C$_{10}$ alkyl or C$_2$ to C$_{10}$ alkenyl and alkynyl. Other embodiments include [(OCH$_2$)$_n$O]$_m$, CH$_3$, O(CH$_2$)$_n$, OCH$_3$, O(CH$_2$)$_n$, NH$_2$, O(CH$_2$)$_n$·CH$_3$, O(CH$_2$)nONH$_2$, and O(CH$_2$)nON[(CH$_2$)nCH$_3$]$_2$, where n and m are from 1 to about 10. Other polynucleotides comprise one of the following at the 2' position: C1 to C10 lower alkyl, substituted lower alkyl, alkenyl, alkynyl, alkaryl, aralkyl, O-alkaryl or O-aralkyl, SH, SCH$_3$, OCN, Cl, Br, CN, CF$_3$, OCF$_3$, SOCH$_3$, SO$_2$CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of a polynucleotide, or a group for improving the pharmacodynamic properties of a polynucleotide, and other substituents having similar properties. In one aspect, a modification includes 2'-methoxyethoxy (2'-O—CH$_2$CH$_2$OCH$_3$, also known as 2'-O-(2-methoxyethyl) or 2'-MOE) (Martin et al., 1995, Helv. Chim. Acta, 78: 486-504) i.e., an alkoxyalkoxy group. Other modifications include 2'-dimethylaminooxyethoxy, i.e., a O(CH2)20N(CH3)2 group, also known as 2'-DMAOE, and 2'-dimethylaminoethoxyethoxy (also known in the art as 2'-O-dimethyl-amino-ethoxy-ethyl or 2'-DMAEOE), i.e., 2'-0-C11)-0-CH2-N(CH3)2.

Still other modifications include 2'-methoxy (2'-0-CH3), 2'-aminopropoxy (2'-OCH2CH2CH2NH2), 2'-allyl (2'-CH2-CH=CH2), 2'-O-allyl (2'-0-CH2-CH=CH2) and 2'-fluoro (2'-F). The 2'-modification may be in the arabino (up) position or ribo (down) position. In one aspect, a 2'-arabino modification is 2'-F. Similar modifications may also be made at other positions on the polynucleotide, for example, at the 3' position of the sugar on the 3' terminal nucleotide or in 2'-5' linked polynucleotides and the 5' position of 5' terminal nucleotide. Polynucleotides may also have sugar mimetics such as cyclobutyl moieties in place of the pentofuranosyl sugar. See, for example, U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; 5,792,747; and 5,700,920, the disclosures of which are incorporated by reference in their entireties herein.

Further modifications include those that extend the genetic code such as, without limitation, Iso-dC and Iso-dG. Iso-dC and Iso-dG are chemical variants of cytosine and guanine, respectively. Iso-dC will hydrogen bond with Iso-dG but not with dG. Similarly, Iso-dG will base pair with Iso-dC but not with dC [Switzer et al., Biochemistry 32:10489-96 (1993)]. In these aspects, controlled tailing by addition of Iso-dC bases is achieved by using a poly (iso-dG) attenuator molecule and vice versa.

In one aspect, a modification of the sugar includes Locked Nucleic Acids (LNAs) in which the 2'-hydroxyl group is linked to the 3' or 4' carbon atom of the sugar ring, thereby forming a bicyclic sugar moiety. The linkage is in certain aspects a methylene (—CH2-)n group bridging the 2' oxygen atom and the 4' carbon atom wherein n is 1 or 2. LNAs and preparation thereof are described in WO 98/39352 and WO 99/14226, the disclosures of which are incorporated herein by reference.

Labels

In some aspects of the disclosure, any polynucleotide used in the methods or compositions described herein comprises a label. In some of these aspects the label is fluorescent. Methods of labeling polynucleotides with fluorescent molecules and measuring fluorescence are well known in the art. Fluorescent labels useful in the practice of the invention include but are not limited to 1,8-ANS (1-Anilinonaphthalene-8-sulfonic acid), 1-Anilinonaphthalene-8-sulfonic acid (1,8-ANS), 5-(and-6)-Carboxy-2', 7'-dichlorofluorescein pH 9.0, 5-FAM pH 9.0, 5-ROX (5-Carboxy-X-rhodamine, triethylammonium salt), 5-ROX pH 7.0, 5-TAMRA, 5-TAMRA pH 7.0, 5-TAMRA-MeOH, 6 JOE, 6,8-Difluoro-7-hydroxy-4-methylcoumarin pH 9.0, 6-Carboxyrhodamine 6G pH 7.0, 6-Carboxyrhodamine 6G, hydrochloride, 6-HEX, SE pH 9.0, 6-TET, SE pH 9.0, 7-Amino-4-methylcoumarin pH 7.0, 7-Hydroxy-4-methylcoumarin, 7-Hydroxy-4-methylcoumarin pH 9.0, Alexa 350, Alexa 405, Alexa 430, Alexa 488, Alexa 532, Alexa 546, Alexa 555, Alexa 568, Alexa 594, Alexa 647, Alexa 660, Alexa 680, Alexa 700, Alexa Fluor 430 antibody conjugate pH 7.2, Alexa Fluor 488 antibody conjugate pH 8.0, Alexa Fluor 488 hydrazide-water, Alexa Fluor 532 antibody conjugate pH 7.2, Alexa Fluor 555 antibody conjugate pH 7.2, Alexa Fluor 568 antibody conjugate pH 7.2, Alexa Fluor 610 R-phycoerythrin streptavidin pH 7.2, Alexa Fluor 647 antibody conjugate pH 7.2, Alexa Fluor 647 R-phycoerythrin streptavidin pH 7.2, Alexa Fluor 660 antibody conjugate pH 7.2, Alexa Fluor 680 antibody conjugate pH 7.2, Alexa Fluor 700 antibody conjugate pH 7.2, Allophycocyanin pH 7.5, AMCA conjugate, Amino Coumarin, APC (allophycocyanin), Atto 647, BCECF pH 5.5, BCECF pH 9.0, BFP (Blue Fluorescent Protein), BO-PRO-1-DNA, BO-PRO-3-DNA, BOBO-1-DNA, BOBO-3-DNA, BODIPY 650/665-X, MeOH, BODIPY FL conjugate, BODIPY FL, MeOH, Bodipy R6G SE, BODIPY R6G, MeOH, BODIPY TMR-X antibody conjugate pH 7.2, Bodipy TMR-X conjugate, BODIPY TMR-X, MeOH, BODIPY TMR-X, SE, BODIPY TR-X phallacidin pH 7.0, BODIPY TR-X, MeOH, BODIPY TR-X, SE, BOPRO-1, BOPRO-3, Calcein, Calcein pH 9.0, Calcium Crimson, Calcium Crimson Ca2+, Calcium Green, Calcium Green-1 Ca2+, Calcium Orange, Calcium Orange Ca2+, Carboxynaphthofluorescein pH 10.0, Cascade Blue, Cascade Blue BSA pH 7.0, Cascade Yellow, Cascade Yellow antibody conjugate pH 8.0, CFDA, CFP (Cyan Fluorescent Protein), CI-NERF pH 2.5, CI-NERF pH 6.0, Citrine, Coumarin, Cy 2, Cy 3, Cy 3.5, Cy 5, Cy 5.5, CyQUANT GR-DNA, Dansyl Cadaverine, Dansyl Cadaverine, MeOH, DAPI, DAPI-DNA, Dapoxyl (2-aminoethyl) sulfonamide, DDAO pH 9.0, Di-8 ANEPPS, Di-8-ANEPPS-lipid, DiI, DiO, DM-NERF pH 4.0, DM-NERF pH 7.0, DsRed, DTAF, dTomato, eCFP (Enhanced Cyan Fluorescent Protein), eGFP (Enhanced Green Fluorescent Protein), Eosin, Eosin antibody conjugate pH 8.0, Erythrosin-5-isothiocyanate pH 9.0, Ethidium Bromide, Ethidium homodimer, Ethidium homodimer-1-DNA, eYFP (Enhanced Yellow Fluorescent Protein), FDA, FITC, FITC antibody conjugate pH 8.0, FlAsH, Fluo-3, Fluo-3 Ca2+, Fluo-4, Fluor-Ruby, Fluorescein, Fluorescein 0.1 M NaOH, Fluorescein antibody conjugate pH 8.0, Fluorescein dextran pH 8.0, Fluorescein pH 9.0, Fluoro-Emerald, FM 1-43, FM 1-43 lipid, FM 4-64, FM 4-64, 2% CHAPS, Fura Red Ca2+, Fura Red, high Ca, Fura Red, low Ca, Fura-2 Ca2+, Fura-2, high Ca, Fura-2, no Ca, GFP (S65T), HcRed, Hoechst 33258, Hoechst 33258-DNA, Hoechst 33342, Indo-1 Ca2+, Indo-1, Ca free, Indo-1, Ca saturated, JC-1, JC-1 pH 8.2, Lissamine rhodamine, LOLO-1-DNA, Lucifer Yellow, CH, LysoSensor Blue, LysoSensor Blue pH 5.0, LysoSensor Green, LysoSensor Green pH 5.0, LysoSensor Yellow pH 3.0, LysoSensor Yellow pH 9.0, LysoTracker Blue, LysoTracker Green, LysoTracker Red, Magnesium Green, Magnesium Green Mg2+, Magnesium Orange, Marina Blue, mBanana, mCherry, mHoneydew, MitoTracker Green, MitoTracker Green FM, MeOH, MitoTracker Orange, MitoTracker Orange, MeOH, MitoTracker Red, MitoTracker Red, MeOH, mOrange, mPlum, mRFP, mStrawberry, mTangerine, NBD-X, NBD-X, MeOH, NeuroTrace 500/525, green fluorescent Nissl stain-RNA, Nile Blue, EtOH, Nile Red, Nile Red-lipid, Nissl, Oregon Green 488, Oregon Green 488 antibody conjugate pH 8.0, Oregon Green 514, Oregon Green 514 antibody conjugate pH 8.0, Pacific Blue, Pacific Blue antibody conjugate pH 8.0, Phycoerythrin, PO-PRO-1, PO-PRO-1-DNA, PO-PRO-3, PO-PRO-3-DNA, POPO-1, POPO-1-DNA, POPO-3, Propidium Iodide, Propidium Iodide-DNA, R-Phycoerythrin pH 7.5, ReAsH, Resorufin, Resorufin pH 9.0, Rhod-2, Rhod-2 Ca2+, Rhodamine, Rhodamine 110, Rhodamine 110 pH 7.0, Rhodamine 123, MeOH, Rhodamine Green, Rhodamine phalloidin pH 7.0, Rhodamine Red-X antibody conjugate pH 8.0, Rhodaminen Green pH 7.0, Rhodol Green antibody conjugate pH 8.0, Sapphire, SBFI-Na+, Sodium Green Na+, Sulforhodamine 101, SYBR Green I, SYPRO Ruby, SYTO 13-DNA, SYTO 45-DNA, SYTOX Blue-DNA, Tetramethylrhodamine antibody conjugate pH 8.0, Tetramethylrhodamine dextran pH 7.0, Texas Red-X antibody conjugate pH 7.2, TO-PRO-1-DNA, TO-PRO-3-DNA, TOTO-1-DNA, TOTO-3-DNA, TRITC, X-Rhod-1 Ca2+, YO-PRO-1-DNA, YO-PRO-3-DNA, YOYO-1-DNA, and YOYO-3-DNA.

Other labels besides fluorescent molecules can be used, such as chemiluminescent molecules, which will give a detectable signal or a change in detectable signal upon hybridization, and radioactive molecules. In addition, affinity labels including but not limited to biotin, dual biotin and digoxigenin may be used.

Methods

The disclosure provides methods for using the composition comprising a nucleic acid polymerase and an attenuator molecule. In one embodiment, a method of extending a substrate polynucleotide is provided comprising incubating the substrate polynucleotide with a composition as described herein under conditions sufficient to allow addition of a tail sequence to the 3' end of the substrate polynucleotide, wherein the addition of the tail sequence allows association between the tail sequence and the attenuator molecule to form a complex. In some aspects, the method further comprises degrading the attenuator molecule following extension of the substrate polynucleotide. In another aspect, practice of the methods of the disclosure further comprises isolating the extended substrate polynucleotide. In some aspects, the methods described herein further comprise mixing a composition as described herein with the substrate polynucleotide and a nucleotide that is complementary to the homopolymeric portion of the attenuator molecule. Various aspects of the disclosure contemplate a substrate polynucleotide and/or attenuator molecule that is partially double stranded. In addition, some aspects of the methods further comprise an annealing step, wherein a double stranded polynucleotide is produced by annealing a first polynucleotide to a second polynucleotide under conditions sufficient to allow the first polynucleotide to associate with the second polynucleotide. In some aspects of the disclosure the substrate polynucleotide is single stranded RNA or DNA. In various aspects wherein the substrate polynucleotide is double stranded, each of the two free 3' ends are extended. In other aspects, only one of the free 3' ends of the double stranded substrate polynucleotide is extended. In aspects wherein only one of the free 3' ends of the double stranded polynucleotide is extended, it is contemplated that the other free 3' end is prevented from being extended. Yet another aspect of the disclosure contemplates a method comprising an immobilization step, wherein an attenuator/attenuator-adaptor molecule or a substrate polynucleotide or both are immobilized to a surface. Further aspects of the disclosure contemplate a ligating step, and still further aspects contemplate a step comprising inactivation of an enzyme. In any of the methods disclosed herein, it is contemplated that more than one reaction takes place in the same reaction vessel. By way of example, the disclosure contemplates methods wherein a tailing reaction and a ligation occurs in the same reaction vessel.

Accordingly, the methods provided by the disclosure comprise, in various aspects, an incubation step, a degrading step, a mixing step, an isolation step, an annealing step, an inactivating step, a ligating step and an immobilization step. In some aspects, the method comprises an incubation step and a mixing step. In another aspect, the method comprises an incubation step and an isolation step. In some aspects, the method comprises an incubation step and an inactivating step. A further aspect of the disclosure provides a method comprising an incubation step, a mixing step and a ligating step. Another aspect of the disclosure provides a method comprising an incubation step, an inactivating step and a degrading step. In a further aspect, the method comprises an incubation step, a mixing step, and an annealing step. Another aspect of the disclosure provides a method comprising an incubation step, a mixing step, an annealing step, a ligating step and an immobilization step. In yet another aspect, the method comprises an incubation step, a mixing step, an annealing step and an isolation step. A further aspect of the disclosure contemplates a method comprising an incubation step, a mixing step, an annealing step, a degradation step and an isolation step. Yet another aspect of disclosure provides a method comprising an incubation step, a mixing step, an annealing step, a degradation step, an immobilization step and an isolation step. A further aspect of the disclosure provides a method comprising an incubation step, a mixing step, an annealing step, an inactivating step, a degradation step, an immobilization step and an isolation step. It will be understood by one of skill in the art that the various steps can be used in any combination and order, with only the mixing and incubation steps being the common feature to all methods.

Also contemplated is a method whereby NGS library preparation as described herein using controlled tailing and ligation is coupled with an enrichment step for targeted NGS sequencing. In one embodiment, the input substrate polynucleotide for controlled tailing and ligation mediated NGS library preparation is an enriched fraction of a genome obtained by any method, including but not limited to hybridization capture and target-specific PCR. In another embodiment, the product of a controlled tailing and ligation mediated NGS library as described in this disclosure is subsequently subject to targeted enrichment by any method, including but not limited to hybridization capture. In an alternative embodiment, the input substrate polynucleotide is first subject to a controlled tailing and ligation reaction to introduce a first NGS adaptor, wherein a second step comprising a targeted enrichment by hybridization capture is performed, and in a third step, a second NGS adaptor is introduced on the enriched DNA fraction by either a second controlled tailing and ligation reaction or a blunt ligation or a TA ligation.

Methods of the disclosure involving controlled tailing and ligation are, in various embodiments, applied to primer-extension products or amplification products including but not limited to those amplification products derived from polymerase chain reaction, isothermal amplification and RNA transcription. The methods of the disclosure can also be applied to synthetic nucleic acids. Specifically, the methods are applicable for sequence analysis of synthetic oligonucleotides, synthetic genes, genomic segments and genomes.

Also contemplated in this disclosure is a method that combines simultaneous end repair with the controlled tailing and ligation reaction. End repair includes but is not limited to the following enzymes: polynucleotide kinase, T4 DNA polymerase, uracil DNA glycosylase, APE1 endonuclease, endonuclease III (Nth), endonuclease IV, endonuclease V, endonuclease VIII, Fpg, hAAG, hOGG1, and hsMUG1. End repair is a separate reaction incorporated into existing NGS library preparation methods to repair damage induced by physical shearing of DNA as a means of DNA fragmentation within this disclosure. In this aspect, the controlled tailing and ligation reaction conditions are compatible with end repair reaction conditions and can be performed simultaneously as a single step.

Without wishing to be bound by theory, it is contemplated by the disclosure that, in some aspects, reactions that take place in solution are more efficient than those that involve an immobilization step. By "more efficient" is meant that the reaction in solution is completed in less time than the same reaction following an immobilization step.

Each of the method steps described above are discussed in further detail below.

Incubation Step

The methods of the disclosure involve incubating a substrate polynucleotide with a composition as described herein under conditions sufficient to allow addition of a tail sequence to the 3' end of the substrate polynucleotide. In some aspects, an agent selected from the group consisting of polyethylene glycol (PEG), a polyamine, hexamine cobalt and CoC12 is used to facilitate the association of an attenuator/attenuator-adaptor molecule and a substrate polynucleotide, or to control the addition of nucleotides to the substrate polynucleotide.

Methods provided by the disclosure also include those wherein a multiplicity of nucleotides are added to the substrate polynucleotide to form the tail sequence. In some aspects, the attenuator molecule associates with the tail sequence over all or part of the attenuator molecule length. In further embodiments, the attenuator molecule associates with the tail sequence during the process of adding the tail sequence.

In general, methods described herein also include those wherein association of the attenuator molecule with the tail sequence regulates addition of nucleotides to the polynucleotide.

With respect to the addition of nucleotides to the substrate polynucleotide, the disclosure provides methods wherein the conditions regulate the addition of a tail sequence to the substrate polynucleotide. For example and without limitation, in one aspect the addition of a tail sequence to the substrate polynucleotide is temperature sensitive. In one embodiment, the temperature at which the tail sequence is added to the substrate polynucleotide is at least about 4° C. In further embodiments, the temperature conditions at which the tail sequence is added is at least about 4° C. to about 50° C., about 4° C. to about 40° C., about 4° C. to about 37° C., about 4° C. to about 30° C., about 4° C. to about 25° C., about 4° C. to about 20° C., about 10° C. to about 50° C., about 10° C. to about 40° C., about 10° C. to about 37° C., about 10° C. to about 30° C., about 10° C. to about 25° C., about 10° C. to about 20° C., about 20° C. to about 50° C., about 20° C. to about 40° C., about 20° C. to about 37° C., about 25° C. to about 37° C., about 25° C. to about 40° C., about 30° C. to about 40° C., at least about 5° C., at least about 6° C., at least about 7° C., at least about 8° C., at least about 9° C., at least about 10° C., at least about 11° C., at least about 12° C., at least about 13° C., at least about 14° C., at least about 15° C., at least about 16° C., at least about 17° C., at least about 18° C., at least about 19° C., at least about 20° C., at least about 21° C., at least about 22° C., at least about 23° C., at least about 24° C., at least about 25° C., at least about 26° C., at least about 27° C., at least about 28° C., at least about 29° C., at least about 30° C., at least about 31° C., at least about 32° C., at least about 33° C., at least about 34° C., at least about 35° C., at least about 36° C., at least about 37° C., at least about 38° C., at least about 39° C., at least about 40° C., at least about 41° C., at least about 42° C., at least about 43° C., at least about 44° C., at least about 45° C., at least about 46° C., at least about 47° C., at least about 48° C., at least about 49° C., at least about 50° C. or higher.

Accordingly, in certain aspects the temperature at which the incubation step is performed is determinative of the number of nucleotides that are added to the substrate polynucleotide. By way of example, methods are provided wherein the length of a tail added to a substrate polynucleotide is about 10 nucleotides at 25° C., about 11 nucleotides at 30° C., about 13 nucleotides at 37° C. and about 16 nucleotides at 45° C.

In addition to the temperature at which the incubation step is performed, another condition that regulates the addition of a tail sequence to the substrate polynucleotide is the length of time that the incubation step is allowed to progress. In general, the length of time that the incubation step is allowed to progress is about 0.5 minutes to about 120 minutes. In some aspects, the length of time that the incubation step is allowed to progress is at least about 0.5 minutes and up to about 1, 2 or 3 minutes; or at least about 1 minute and up to about 2, 5 or 10 minutes; or at least about 2 minutes and up to about 5, 8 or 10 minutes; or at least about 5 minutes and up to about 10, 15 or 20 minutes; or at least about 10 minutes and up to about 15, 20 or 30 minutes; or at least about 20 minutes and up to about 30, 40 or 60 minutes; or at least about 30 minutes and up to about 40, 60 or 80 minutes; or at least about 60 minutes and up to about 80, 90 or 100 minutes; or at least about 90 minutes and up to about 100, 110 or 120 minutes. In various embodiments, the length of time that the incubation step is allowed to progress is about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 31, about 32, about 33, about 34, about 35, about 36, about 37, about 38, about 39, about 40, about 41, about 42, about 43, about 44, about 45, about 46, about 47, about 48, about 49, about 50, about 51, about 52, about 53, about 54, about 55, about 56, about 57, about 58, about 59, about 60, about 61, about 62, about 63, about 64, about 65, about 66, about 67, about 68, about 69, about 70, about 71, about 72, about 73, about 74, about 75, about 76, about 77, about 78, about 79, about 80, about 81, about 82, about 83, about 84, about 85, about 86, about 87, about 88, about 89, about 90, about 91, about 92, about 93, about 94, about 95, about 96, about 97, about 98, about 99, about 100, about 101, about 102, about 103, about 104, about 105, about 106, about 107, about 108, about 109, about 110, about 111, about 112, about 113, about 114, about 115, about 116, about 117, about 118, about 119, about 120 minutes or more.

The pH at which the incubation is performed is from about 5.0 to about 9.0. In one aspect, the pH is about 7.9. In some aspects, the pH at which the incubation is performed is at least about pH 5.0 and up to about pH 5.1, 5.5 or 5.8; or at least about pH 5.5 and up to about pH 5.8, 6.0 or 6.2; or at least about pH 6.0 and up to about pH 6.2, 6.5 or 6.8; or at least about pH 6.5 and up to about pH 7.0, 7.2 or 7.5; or at least about pH 7.5 and up to about pH 7.8, 8.0 or 8.2; or at least about pH 8.0 and up to about pH 8.2, 8.5 or 9.0. In various aspects, the pH at which the incubation is performed is about pH 5.1, about pH 5.2, about pH 5.3, about pH 5.4, about pH 5.5, about pH 5.6, about pH about 5.7, about pH 5.8, about pH 5.9, about pH 6.0, about pH 6.1, about pH 6.2, about pH 6.3, about pH 6.4, about pH 6.5, about pH 6.6, about pH 6.7, about pH 6.8, about pH 6.9, about pH 7.0, about pH 7.1, about pH 7.2, about pH 7.3, about pH 7.4, about pH 7.5, about pH 7.6, about pH 7.7, about pH 7.8, about pH 7.9, about pH 8.0, about pH 8.1, about pH 8.2, about pH 8.3, about pH 8.4, about pH 8.5, about pH 8.6, about pH 8.7, about pH 8.8, about pH 8.9, pH 9.0 or higher.

Degrading Step

In aspects of the method wherein an attenuator molecule is degradable, a degrading step optionally follows the incubation step. In one aspect, an amount of an enzyme that possesses a nucleolytic activity is added to the reaction vessel and the mixture is incubated for an additional period of time at the optimal temperature of the enzyme. In various aspects wherein the attenuator molecule is a polynucleotide, the enzyme possessing a nucleolytic activity is selected from the group consisting of a DNA glycosylase, an apurinic/apyrimidinic endonuclease and a ribonuclease. In further aspects, the ribonuclease is selected from the group consisting of RNase H, RNase HII, RNase A, and RNase T1. Accordingly, and by way of example, the attenuator molecule that is degradable comprises, in various aspects, a uracil nucleotide and degradation occurs as a result of the activity of uracil DNA glycosylase. In another aspect, the attenuator molecule that is degradable comprises ribonucleotides and degradation occurs as a result of the activity of a ribonuclease. It will be understood that the nucleolytic enzyme is chosen such that the substrate polynucleotide is not degraded with the attenuator molecule. Thus, in one aspect, an attenuator molecule that comprises ribonucleotides will be used in a method wherein the substrate molecule comprises deoxyribonucleotides, and the nucleolytic enzyme that is used is a ribonuclease that will not degrade the substrate polynucleotide.

The additional period of time that a reaction vessel is incubated at a desired temperature to degrade an attenuator molecule is at least about 5 minutes, but is contemplated to be from about 0.5 minutes to about 60 minutes or more.

Mixing Step

Methods provided herein generally comprise mixing a nucleic acid polymerase, a substrate polynucleotide and an attenuator molecule in a suitable reaction vessel. Additional components of the mixture comprise a suitable buffer in which the nucleic acid polymerase is optimally active, nucleotides for addition to the substrate polynucleotide and a ligase enzyme. Optionally, and according to various methods described below, further components comprise potassium, CoCb, sodium, lithium, calcium manganese, tris and its derivatives, and magnesium.

Suitable reaction vessels are known to those of skill in the art and include, without limitation, a microcentrifuge tube or a microtiter plate.

In some aspects, more than one type of substrate polynucleotide is added to a single reaction vessel. Accordingly, in various aspects, more than one type of attenuator molecule, capable of associating with the more than one type of substrate polynucleotide, may be added to a single reaction vessel. In further aspects, at least 2, at least 3, at least 4, at least 5, at least 6, at least 7, at least 8, at least 9, at least 10 or more types of substrate polynucleotides and attenuator molecules capable of associating with the more than one type of substrate polynucleotide are added to a single reaction vessel. It is further contemplated that a reaction comprises more than one attenuator polynucleotide and/or more than one attenuator-adaptor molecule and/or mixtures of an attenuator polynucleotide and an attenuator-adaptor molecule. The use of more than one attenuator polynucleotide and/or more than one attenuator-adaptor molecule enables multiplexing as well as controlled DNA and RNA tailing-ligation reactions by template independent polymerases such as deoxynucleotidyl transferase (TdT), poly (A) polymerase or poly(U) polymerase.

For nucleic acid polymerases, the amount to be added is about 1 unit ("U") to about 1000 U per reaction. In some aspects, the amount of nucleic acid polymerase to be added is at least about 1 U and up to about 2, 3 or 4 U; or at least about 2 U and up to about 3, 4 or 5 U; or at least about 5 U and up to about 20, 50 or 100 U; or at least about 5 U and up to about 6, 7 or 8 U; or at least about 6 U and up to about 7, 8 or 9 U; or at least about 7 U and up to about 8, 9 or 10 U; or at least about 10 U and up to about 50, 100 or 500 U; or at least about 10 U and up to about 12, 15 or 18 U; or at least about 15 U and up to about 18, 20 or 25 U; or at least about 20 U and up to about 50, 100 or 1000 U; or at least about 20 U and up to about 25, 30 or 35 U; or at least about 30 U and up to about 35, 40 or 50 U; or at least about 40 U and up to about 50, 60 or 70 U; or at least about 50 U and up to about 100, 500 or 1000 U; or at least about 60 U and up to about 80, 90 or 100 U; or at least about 100 U and up to about 120, 150 or 200 U; or at least about 200 U and up to about 250, 275 or 300 U; or at least about 300 U and up to about 325, 350 or 400 U; or at least about 400 U and up to about 450, 500 or 550 U; or at least about 600 U and up to about 700, 800 or 900 U; or at least about 700 U and up to about 800, 900 or 1000 U. In various aspects, the amount of nucleic acid polymerase to be added is about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990 or about 1000 units or more per reaction.

The nucleotides that are added to the reaction vessel will depend on the given application. By way of example, if the attenuator molecule is a homopolymeric polynucleotide, then the nucleotides that are added to the reaction vessel are the nucleotides which are complementary to the nucleotide making up the homopolymeric portion of the attenuator molecule. It is also contemplated that in various embodiments, mixtures of nucleotides are added to the reaction vessel. Thus, in some embodiments, a mixture of deoxyribonucleotides and ribonucleotides are added to the reaction vessel (e.g., dA/rA, dT/dU/rU, dC/rC or dG/rG). In some embodiments, the inclusion of ribonucleotides in the reaction vessel reduces additional tailing in the presence of a polymerase such as TdT, while the inclusion of deoxynucleotides in the reaction vessel reduces additional tailing in the presence of a polymerase such as poly(A) polymerase or poly(U) polymerase. The nucleotide concentration within the reaction vessel is generally about 0.1 mM, but in various aspects is between about 0.01 to about 5 mM.

As described above, some embodiments of the methods include a ligase enzyme. For the ligase enzyme, the amount to be added is between about 0.1 to about 1000 U per reaction.

For magnesium, it is contemplated that the amount to be added is from about 1 mM to about 100 mM per reaction. In various aspects, the amount of potassium to be added is about 1 mM to about 10 mM, or about 2 mM to about 20 mM, or about 10 mM to about 100 mM.

Isolating Step

In some embodiments, the substrate polynucleotide is isolated. Isolation of the substrate polynucleotide is performed by any method known and understood by one of skill in the art. In one aspect, isolation of the substrate polynucleotide is performed by immobilization of the substrate polynucleotide as described herein. In another aspect, ligand-coupled beads or microspheres are used to specifically associate with the substrate polynucleotide and facilitate its isolation. By way of example, a substrate polynucleotide that was tailed with a homopolymeric adenine sequence can be isolated using a poly-dT-coupled bead. In other aspects, isolation of the substrate polynucleotide is performed by precipitation, gel filtration or spin-column microcentrifugation of the substrate polynucleotide.

Immobilization Step

In some aspects, the attenuator molecule and/or the substrate polynucleotide is covalently or non-covalently coupled to a support. Coupling chemistries and selection of support materials well known in the art are contemplated. For example, supports include those made all or in part of glass, silica, metal, plastic, fiber, resin, and polymers. Exemplary polymers include for example and without limitation cellulose, nitrocellulose, polyacetate, polycarbonate, polystyrene, polyester, polyvinyldifluorobenzene, nylon, carbon fiber or any other suitable polymer material. In certain related embodiments one or a plurality of the attenuator molecules and/or substrate polynucleotides described herein may be provided as an array immobilized on a solid support, which includes any of a number of well known configurations for spatially arranging such molecules in an identifiable (for example and without limitation, addressable) fashion. Immobilization, in various aspects, involves biotinylated attenuator-adaptor molecules and streptavidin (avidin) coated surfaces (for example and without limitation, tubes, beads or magnetic beads). The skilled artisan will be familiar with various compositions and methods for making and using arrays of such solid-phase immobilized attenuator molecule and/or substrate polynucleotide arrays.

Inactivating Step

In some aspects, following incubation of the reaction vessel comprising the components of the reaction, the reaction vessel is further incubated at a higher temperature to inactivate the nucleic acid polymerase. In some aspects, the further incubation is performed for at least about 1 minute and up to about 2, 5 or 10 minutes; or at least about 5 and up to about 10, 20 or 30 minutes; or at least about 10 and up to about 15, 20 or 30 minutes; or at least about 15 and up to about 20, 25 or 30 minutes. In some embodiments, the further incubation is performed for about 1 minute to about 30 minutes. In various aspects, the further incubation is performed for about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30 minutes or more.

The higher temperature at which the further incubation is performed is from about 60 C to about 100° C. In some aspects, the temperature at which the further incubation is performed is at least about 60° C. and up to about 62° C., 65° C. or 68° C.; or at least about 60° C. and up to about 65° C., 70° C. or 75° C.; or at least about 60° C. and up to about 70° C., 75° C. or 80° C.; or at least about 70° C. and up to about 75° C., 80° C. or 85° C.; or at least about 70° C. and up to 80° C., 90° C. or 100° C. In various aspects, the temperature at which the further incubation is performed is about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C. or higher.

Ligating Step

In some aspects of the methods that are provided, the reaction is such that tailing of the substrate polynucleotide occurs simultaneously with substrate polynucleotide ligation to the adaptor molecule. In these aspects, a mixture comprising the nucleic acid polymerase, substrate polynucleotide, attenuator-adaptor molecule, buffer, and ligase enzyme are all present in a single reaction vessel (see, for example and without limitation, Example 9). Incubation of the mixture to produce tailing of the substrate polynucleotide and its ligation to the attenuator-adaptor molecule is identical to the methods described above for tailing alone. In various aspects, the ligase enzyme is a DNA ligase or a RNA ligase. Attenuator molecules that are immobilized have been described herein. In some aspects of the methods, the immobilized attenuator molecule is ligated by a DNA or RNA ligase to a polynucleotide during addition of a tail sequence to the polynucleotide molecule.

For a ligase enzyme, the amount to be added is about 0.1 unit ("U") to about 1000 U per reaction. In some aspects, the amount of ligase enzyme to be added is at least about 0.1 U and up to about 0.5, 1, 2, 3 or 4 U; or at least about 1 U and up to about 3, 4 or 5 U; or at least about 5 U and up to about 20, 50 or 100 U; or at least about 5 U and up to about 6, 7 or 8 U; or at least about 6 U and up to about 7, 8 or 9 U; or at least about 7 U and up to about 8, 9 or 10 U; or at least about 10 U and up to about 50, 100 or 500 U; or at least about 10 U and up to about 12, 15 or 18 U; or at least about 15 U and up to about 18, 20 or 25 U; or at least about 20 U and up to about 50, 100 or 1000 U; or at least about 20 U and up to about 25, 30 or 35 U; or at least about 30 U and up to about 35, 40 or 50 U; or at least about 40 U and up to about 50, 60 or 70 U; or at least about 50 U and up to about 100, 500 or 1000 U; or at least about 60 U and up to about 80, 90 or 100 U; or at least about 100 U and up to about 120, 150 or 200 U; or at least about 200 U and up to about 250, 275 or 300 U; or at least about 300 U and up to about 325, 350 or 400 U; or at least about 400 U and up to about 450, 500 or 550 U; or at least about 600 U and up to about 700, 800 or 900 U; or at least about 700 U and up to about 800, 900 or 1000 U. In various aspects, the amount of ligase enzyme to be added is about 0.2, about 0.3, about 0.4, about 0.5, about 0.6, about 0.7, about 0.8, about 0.9, about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, about 30, about 40, about 50, about 60, about 70, about 80, about 90, about 100, about 110, about 120, about 130, about 140, about 150, about 160, about 170, about 180, about 190, about 200, about 210, about 220, about 230, about 240, about 250, about 260, about 270, about 280, about 290, about 300, about 310, about 320, about 330, about 340, about 350, about 360, about 370, about 380, about 390, about 400, about 410, about 420, about 430, about 440, about 450, about 460, about 470, about 480, about 490, about 500, about 510, about 520, about 530, about 540, about 550, about 560, about 570, about 580, about 590, about 600, about 610, about 620, about 630, about 640, about 650, about 660, about 670, about 680, about 690, about 700, about 710, about 720, about 730, about 740, about 750, about 760, about 770, about 780, about 790, about 800, about 810, about 820, about 830, about 840, about 850, about 860, about 870, about 880, about 890, about 900, about 910, about 920, about 930, about 940, about 950, about 960, about 970, about 980, about 990 or about 1000 units or more per reaction.

Therapeutic Applications

In addition, the disclosure also contemplates therapeutic applications of the attenuated substrate polynucleotide for the control of cellular and viral proliferation. Therapeutic application include but are not limited to antisense regulation of gene expression. Poly(A) polymerases in eukaryotes are responsible for the addition of poly(A) tails during messenger RNA processing. The poly(A) tails of the resulting mRNAs serve multiple functions. They are required for the transport from the nucleus to the cytoplasm, they stimulate the efficiency of protein synthesis and they stabilize mRNA. Polyadenylation of RNA in bacteria plays a significant role in RNA decay. Addition of poly(U) tails in eukaryotes is less understood but may control the degradation of certain RNAs. Synthetic attenuator molecules can potentially be used as antisense molecules to inhibit or limit poly(A) and poly(U) tailing within the cell and thus establish control of cellular and viral proliferation.

Kits

The disclosure provides kits for controlled and limited nucleic acid tailing by a nucleic acid polymerase.

A kit provided by the disclosure comprises an attenuator/optional attenuator-adaptor molecule as described herein (including optional solid phase immobilized attenuator-adaptor molecules), a nucleic acid polymerase, optionally a ligase, a glycosylase and ancillary reagents such as appropriate buffers, wash solutions, indicators and detection media, depending on the particular assay configuration to be practiced. In some aspects, attenuator molecules are premixed with the nucleic acid polymerase or provided in a separate tube.

Examples of such kits include but are not limited to the following.

TdT-Mediated DNA Tailing

This kit comprises the following components. For a poly (dA) tailing kit: TdT enzyme supplemented with 3'-blocked linear or circular poly (dT), poly(dU) or poly(U) attenuator molecule. For a poly (dT) tailing kit: TdT enzyme supplemented with 3'-blocked linear or circular poly (dA) or poly(A) attenuator molecule. For a poly (dG) tailing kit: TdT enzyme supplemented with 3'-blocked linear or circular poly (dC) or poly(C) attenuator molecule. For a poly (dC) tailing kit: TdT enzyme supplemented with 3'-linear linear or circular poly (dG) or poly(G) attenuator molecule.

Poly(A) and Poly(U)-Polymerase-Mediated RNA Tailing

A poly(A) tailing kit comprises: Poly(A) polymerase supplemented with poly (dT), poly(dU) or poly (U) attenuator molecule. A Poly (U) tailing kit comprises: Poly(U) polymerase supplemented with poly (dA), or poly (A) attenuator molecule.

Additional kits comprise reagents for single-reaction tailing and adaptor ligation both for DNA and RNA substrates, and reagents for single reaction tailing-ligation-immobilization both for DNA and RNA substrates. Other kits can introduce barcodes to DNA and RNA molecules. Still other kits can convert DNA and RNA substrates into libraries for next generation sequencing. In one embodiment, a NGS library preparation kit is provided comprising materials for performing (i) a controlled tailing reaction; (ii) end repair; (iii) primer extension; and (iv) blunt end or TA ligation or a second controlled tailing and ligation.

Provided below in the Examples section are specific applications using the compositions and methods described by the disclosure. It will be understood that these applications are provided by way of example only, and are not limiting in any way.

EXAMPLES

Example 1

Attenuated, TdT-Mediated Poly(dA) DNA Tailing in the Presence of Long (>20b) Complementary Poly(dT) Polynucleotide Phase 1: Non-attenuated and fast TdT-mediated poly(dA) tailing of a DNA primer occurs at 37° C. until the size of the tail reaches a critical size that is capable of forming a stable complex with the complementary attenuator molecule containing the long (dT)30 sequence (SEQ ID NO: 62). Tailing of the attenuator molecule is prevented by placing a blocking group at the 3' end of the attenuator molecule (for example and without limitation phosphate, dideoxynucleotide, amino group, inverted dT) or several ribonucleotides, or by using circular attenuator molecules.

Phase 2: Formation of a complex between the attenuator polynucleotide (dT)30 (SEQ ID NO: 62) and the poly(dA) tail results in a significant reduction of the poly(dA) synthesis. Each subsequent dA base added by the TdT enzyme increases the length and stability of the duplex, thus leading to almost complete inhibition of the poly(dA) synthesis by the TdT enzyme (FIG. 1).

Figure 38:
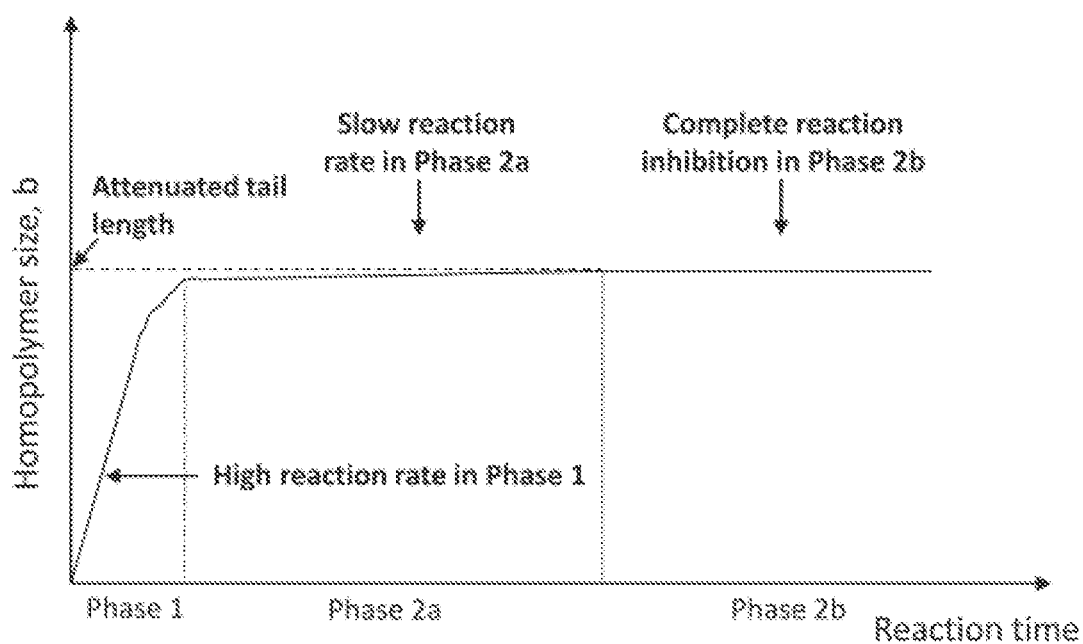
FIG. 38 is a graph demonstrating that kinetics of poly(dA) tailing in the presence of a long attenuator molecule (>20b).

Kinetics of Poly(dA) Tailing in the Presence of Long Poly (dT) Attenuator Molecule In some embodiments of the methods, TdT-mediated dA tailing at 37° C. in the presence of a long attenuator molecule produces relatively short tails (~13 b) with very narrow size distribution as depicted in FIG. 38.

Figure 2:
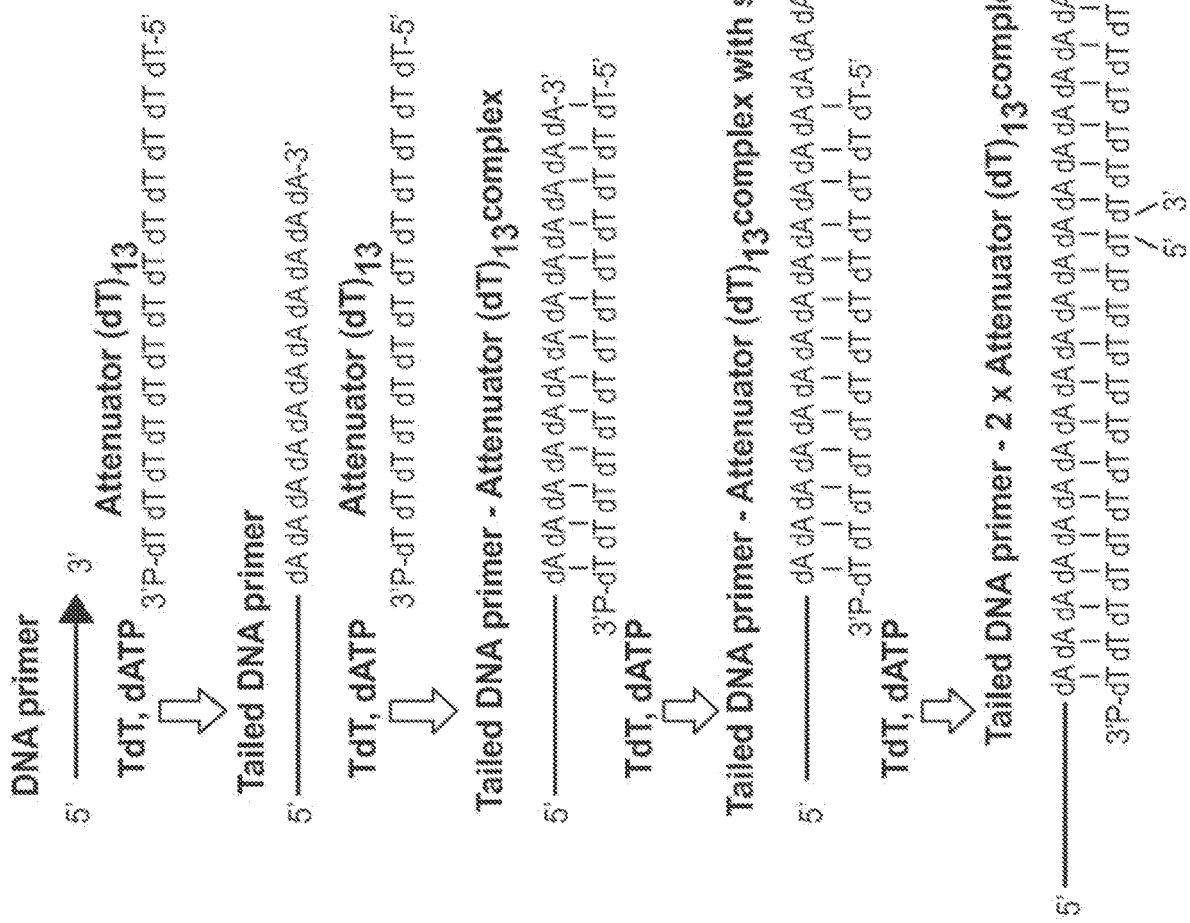
FIG. 2 depicts attenuated polymerase-mediated poly(dA) tailing with short (12-14b) complementary poly (dT) polynucleotides. The Figure exemplifies, without limitation, using TdT enzyme for the tailing reaction.

Attenuated TdT-Mediated Poly(dA) Tailing with Short (12-14b) Complementary Poly (dT) Polynucleotides In further embodiments, a method is provided wherein non-attenuated and fast TdT¬mediated poly(dA) tailing of a substrate DNA primer occurs in phase 1 (FIG. 2). Formation of a complex between the attenuator polynucleotide and poly(A) tail and reduction of the poly(dA) synthesis rate in phase 2a. At this phase every additionally added dA-base stabilizes the complex more until the tail length reaches the full length of the attenuator molecule and forms a blunt duplex end. The reaction never goes into Phase 2b as in alternative embodiments of the methods (see above) because of a limited size of the attenuator molecule.

In phase 3 (FIG. 3), slow poly(dA) tailing of a blunt-ended substrate then occurs until creation of a 3' single-stranded poly(dA) overhang containing 3-4 dA bases. Phases 1 through 3 are then repeated.

Figure 3:
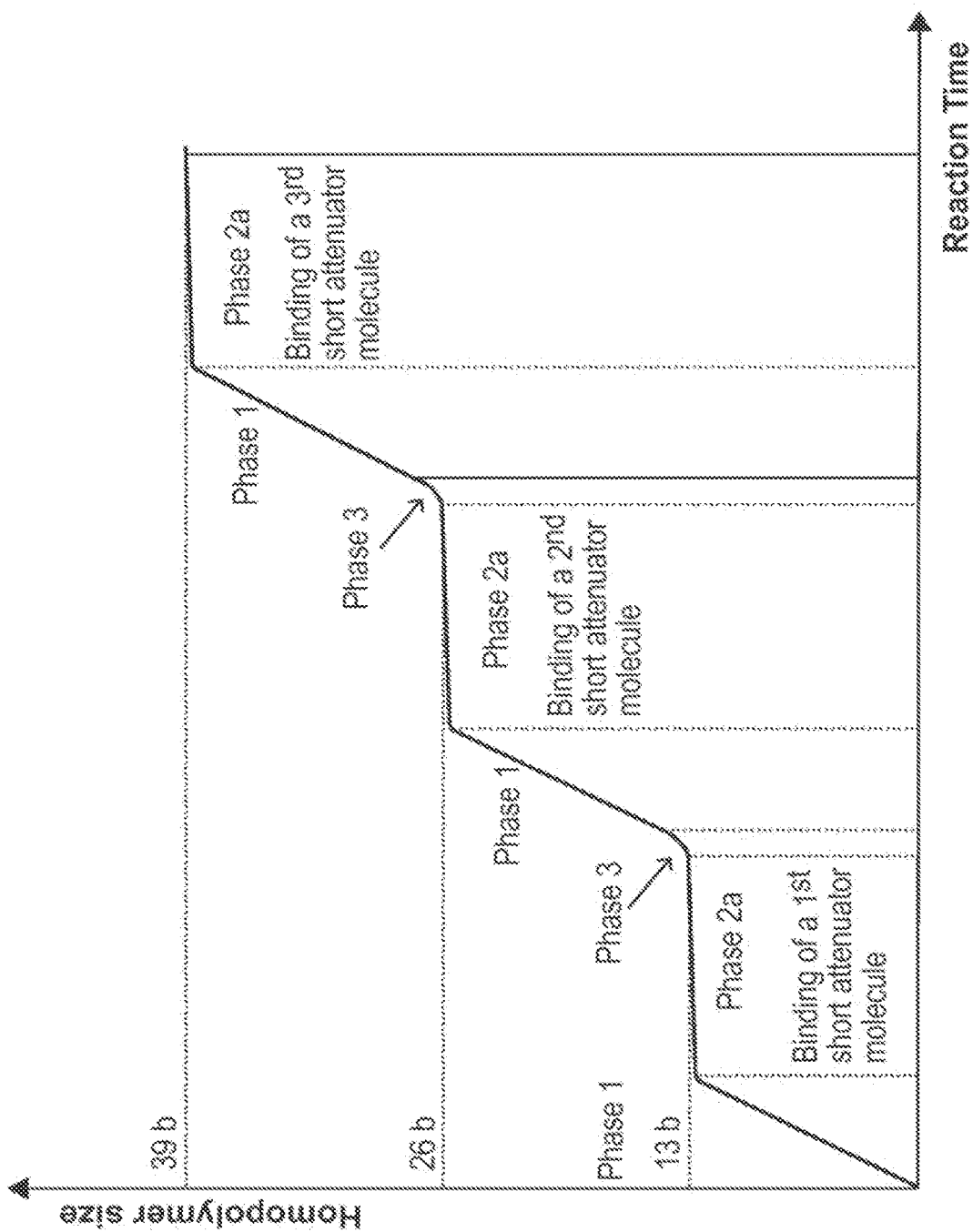
FIG. 3 depicts the expected kinetics of poly(dA) tailing in the presence of short poly(dT) attenuator molecule.

Kinetics of Poly(dA) Tailing in the Presence of Short Poly(dT) Attenuator Molecule In some aspects, TdT-mediated DNA dA tailing in the presence of a short attenuator molecule results in the synthesis of DNA molecules where the poly(dA) tails have a discrete, ladder-like size distribution with the length of tail having, for example and without limitation, multiples of 13 bases (13, 26, 39, etc.) (FIG. 3). In another embodiment, a method is contemplated wherein attenuated TdT-mediated poly(dA) tailing is performed with a degradable attenuator polynucleotide containing dU bases (FIG. 4).

Figure 5:
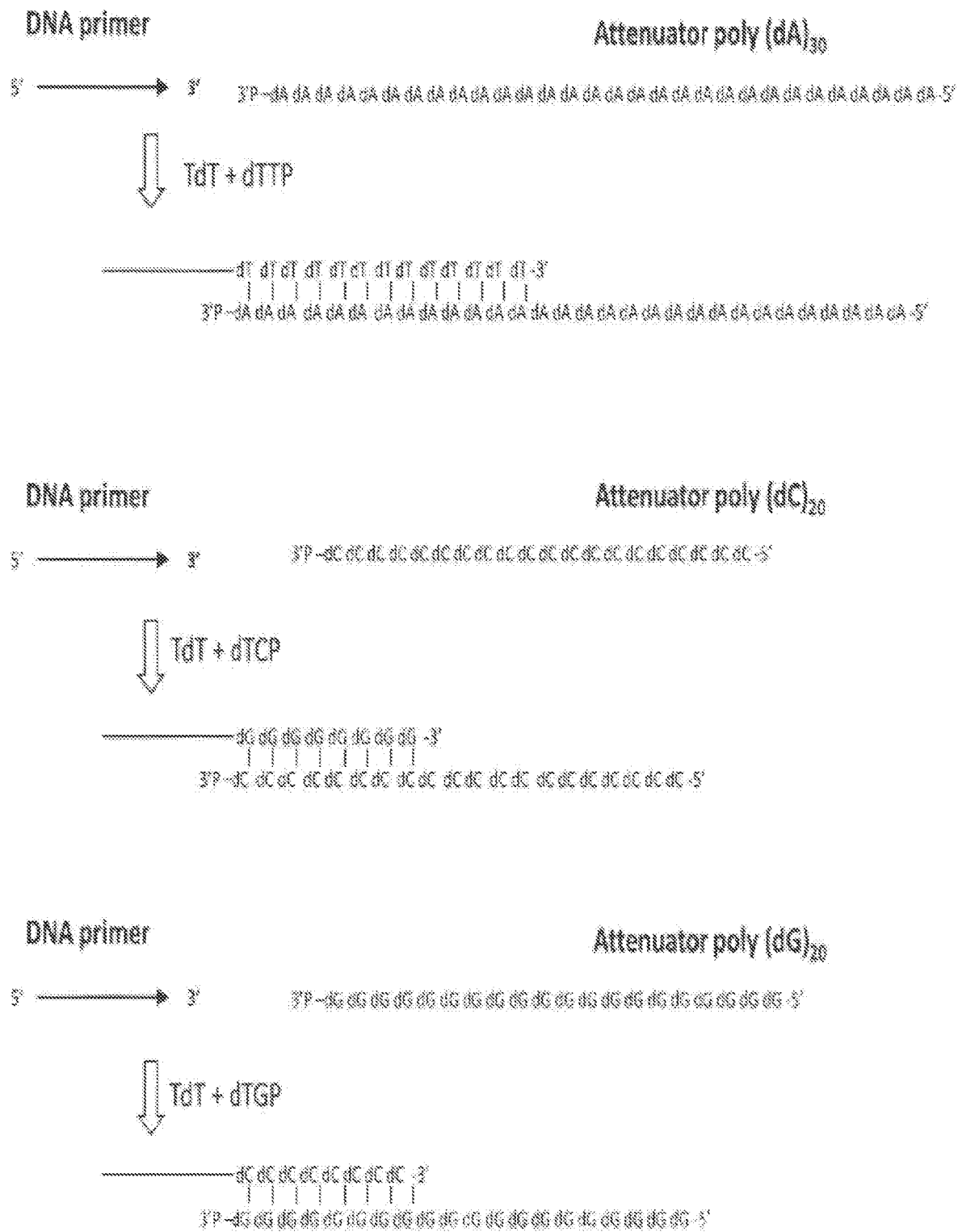
FIG. 5 depicts the attenuated polymerase-mediated poly (dT), poly(dG) and poly(dC) tailing with a long (>20b) complementary attenuator polynucleotide. The Figure exemplifies, without limitation, using TdT enzyme for the tailing reaction.
Figure 6:
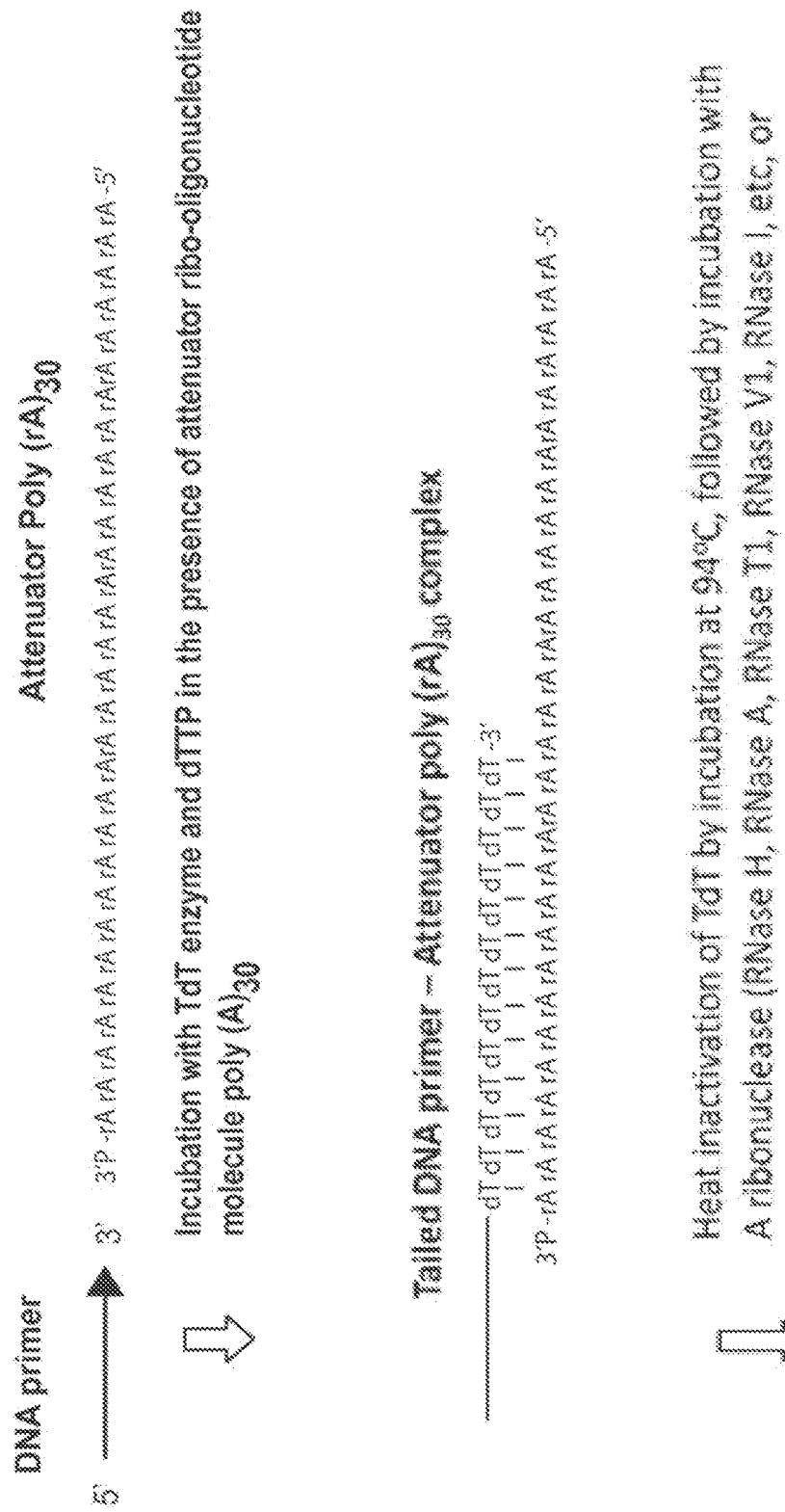
FIG. 6 depicts attenuated polymerase-mediated poly(dA), poly(dT), poly(dG) and poly(dC) tailing with degradable attenuator ribo-polynucleotides. The Figure exemplifies, without limitation, using TdT enzyme for the tailing reaction.

Methods provided by the disclosure also include the attenuated TdT-mediated poly(dT), poly(dG) and poly(dC) tailing with a long (about 20-30 bases) complementary attenuator polynucleotide (see FIG. 5). Also provided is a method of attenuated TdT-mediated poly(dA), poly(dT), poly(dG) and poly(dC) tailing with degradable attenuator ribo¬polynucleotides (FIG. 6).

Controlled RNA Tailing by Poly(A) and Poly(U) Polymerases

The methods described herein relating to the attenuation and the control of TdT-mediated homopolymeric DNA tailing are also contemplated to be applied to an enzymatic reaction catalyzed by poly (A) or poly (U) polymerase that add poly(A) and poly(U) sequences to RNA templates. Similar to methods relating to DNA, 3'-blocked linear poly(U) and poly(A), non-blocked poly (dU) and poly(dA) molecules, and poly(U), poly(A), poly (dU), poly(dA) poly (dU) and poly(dA) molecules, and poly(U), poly(A), poly (dU), poly(dA) circles can be used as attenuators of poly(A) and poly(U) polymerases.

Controlled tailing of RNA by poly(A) and poly(U) polymerases with C and G ribonucleotides, in various aspects, requires a corresponding DNA or RNA attenuator molecule.

Figure 7:
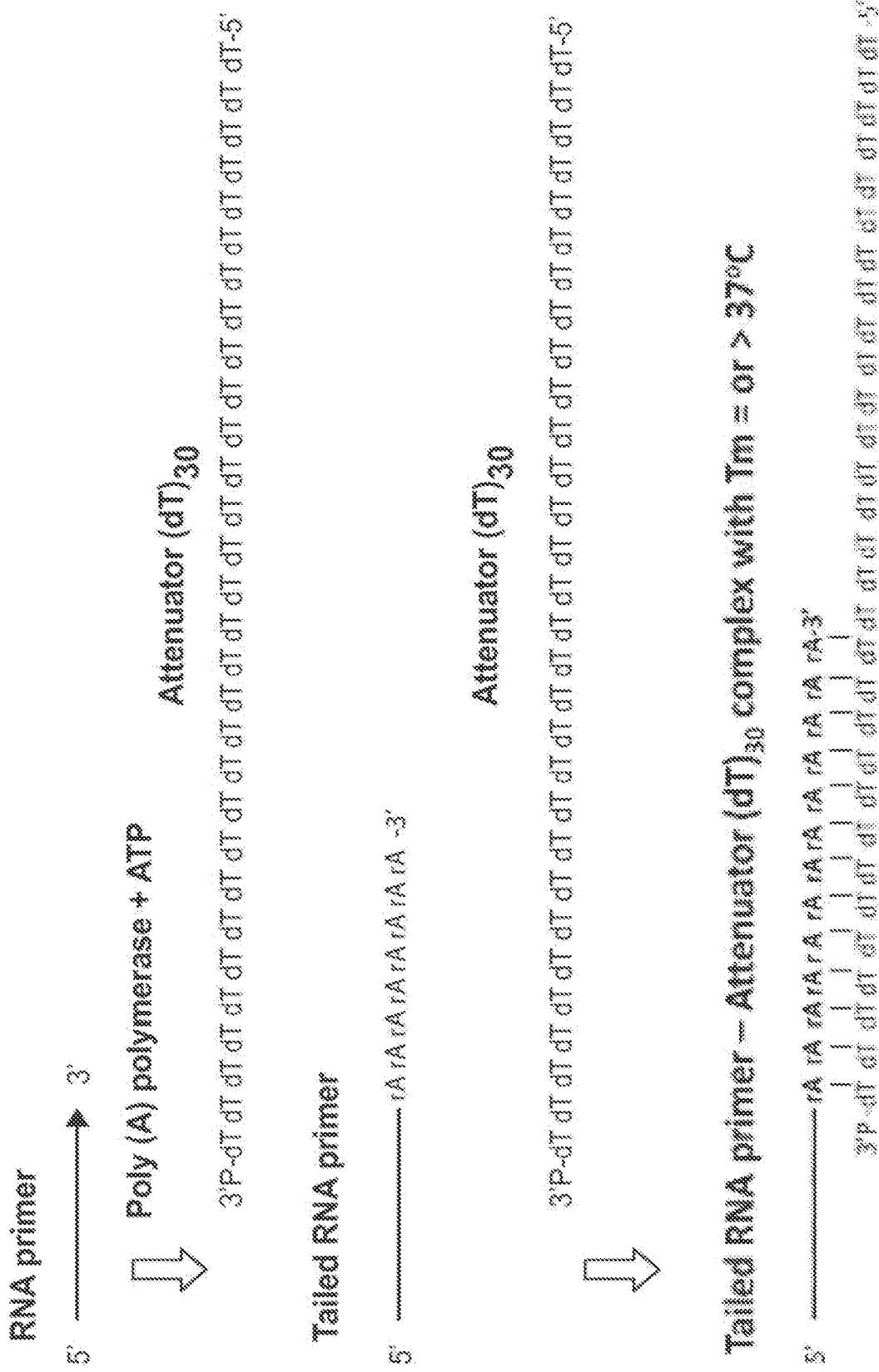
FIG. 7 depicts attenuated poly (A)-polymerase-mediated poly (rA) tailing of RNA substrates using a complementary DNA poly (dT)$_{30}$ polynucleotide (SEQ ID NO: 62).

FIG. 7 depicts attenuated poly (A)-polymerase-mediated poly (rA) tailing of RNA substrates using a complementary DNA poly (dT)30 polynucleotide (SEQ ID NO: 62). In phase 1 (top portion of FIG. 7), non-attenuated and fast poly(A)-polymerase-mediated poly (A) tailing of an RNA primer is shown. In phase 2 (following addition of a poly (rA) tail), formation of a stable complex between the attenuator polynucleotide poly(dT)30 (SEQ ID NO: 62) and the poly (A) tail results in a significant reduction or even complete inhibition of the poly (A) synthesis.

Another aspect of the methods provides attenuated poly (U)-polymerase-mediated poly (rU) tailing of RNA substrates using complementary DNA poly (dA)30 (SEQ ID NO: 68) polynucleotide (FIG. 8). The top portion of FIG. 8 depicts phase 1 of such methods, wherein non-attenuated poly(U)-polymerase-mediated poly (U) tailing of an RNA primer takes place. In phase 2 (following addition of a poly (rU) tail), formation of a stable complex occurs between the attenuator polynucleotide poly(dA)30 (SEQ ID NO: 68) and the poly (U) tail results in a significant reduction or even complete inhibition of the poly (U) synthesis.

Figure 9:
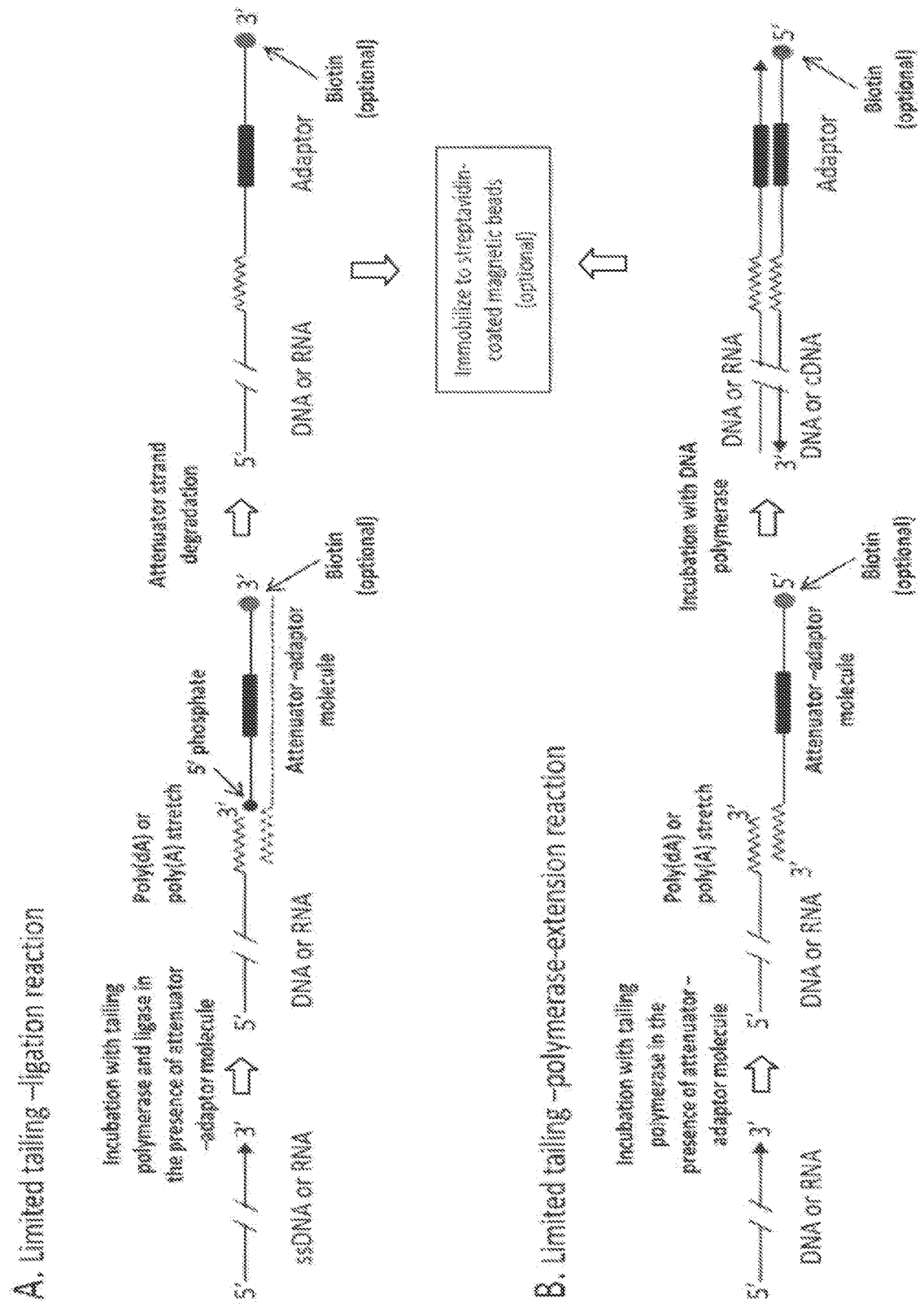
FIG. 9A depicts 3'-end adaptor attachment to single-stranded DNA or RNA molecules using a limited tailing-ligation reaction.
FIG. 9B depicts 3'-end adaptor attachment to single-stranded DNA and RNA molecules using a limited tailing-polymerase-extension reaction.

Use of Controlled, Size-Limited Tailing for Adaptor (Barcode) Attachment to One End of DNA or RNA Fragments and Immobilization to a Solid Support Previously described attenuator molecules are degradable or non-degradable homopolymeric molecules complementary to tails produced by, for example and without limitation, TdT, poly(A) or poly(U) polymerases. Below is introduced a class of attenuator molecules that in addition to their homopolymeric 3'-domain have a single-stranded or double-stranded domain at the 5' portion. These domains are used to introduce an adaptor sequence downstream of the tail region by polymerization or ligation reaction. An advantage of the ligation reaction is that it is coupled with the non-template homopolymeric tailing reaction in a single-tube, single-step reaction. Use of such tailing-ligation reactions provides a simple and efficient way for creation of DNA, RNA or cDNA libraries with one or two adaptors with application for sample preparation from genomic DNA and RNA next generation sequencing (NGS) applications. A schematic of 3'-end adaptor attachment to single-stranded DNA or RNA molecules using a limited tailing reaction is provided in FIG. 9. Part A of FIG. 9 depicts a limited tailing-ligation reaction. In such a reaction, single strand (ss) DNA or RNA is incubated with a template-independent polymerase and ligase in the presence of an attenuator-adaptor molecule that is partially double stranded, where the 3'-blocked single-stranded poly(T) or poly (dT) portion of the attenuator-adaptor serves as an attenuator and the 5'-phosphorylated, double-stranded portion of the attenuator-adaptor serves as an adaptor. A limited poly(dA) or poly(A) stretch is then added to the polynucleotide via a template-independent polymerase, and forms a duplex with the single-stranded portion of the attenuator-adaptor. The adaptor portion of the attenuator-adaptor is then ligated to the attenuated polynucleotide via the 5' phosphate present on the adaptor molecule. The controlled tailing and ligation reactions occur in a closed-tube format. The adaptor molecule optionally further comprises a tag (for example and without limitation, biotin). The ligated molecule is then optionally immobilized to streptavidin-coated magnetic beads to facilitate isolation.

Part B of FIG. 9 depicts a limited tailing-polymerase-extension reaction. In such a reaction, DNA or RNA is incubated with a template-independent polymerase in the presence of an attenuator-adaptor molecule that is single stranded. A poly(dA) or poly(A) stretch is then added to the polynucleotide via a template-independent polymerase, and the presence of a DNA polymerase will allow for extension across the DNA or RNA molecule, thereby creating a double stranded product. The controlled tailing and extension reactions can be done in a closed-tube format. In this case, the deoxynucleotide triphosphate (dNTP) mix must include heat-activatable dTTP, dCTP and dGTP (CleanAmp nucleotides, TriLink Bio Technologies, San Diego) and standard dATP, and the 3' end of a single stranded attenuator-adaptor must also contain a heat-activated base. As a result, controlled attenuated tailing would occur at 37° C. when only dATP is available and the other nucleotides and 3' end of the attenuator-adaptor remains blocked. After heating the mixture at 95° C., the remaining nucleotides become activated and the 3' end of the attenuator-adaptor becomes extendable. The adaptor molecule optionally further comprises a tag (for example and without limitation, biotin). The product molecule is then optionally immobilized to streptavidin-coated magnetic beads to facilitate isolation.

Figure 10:
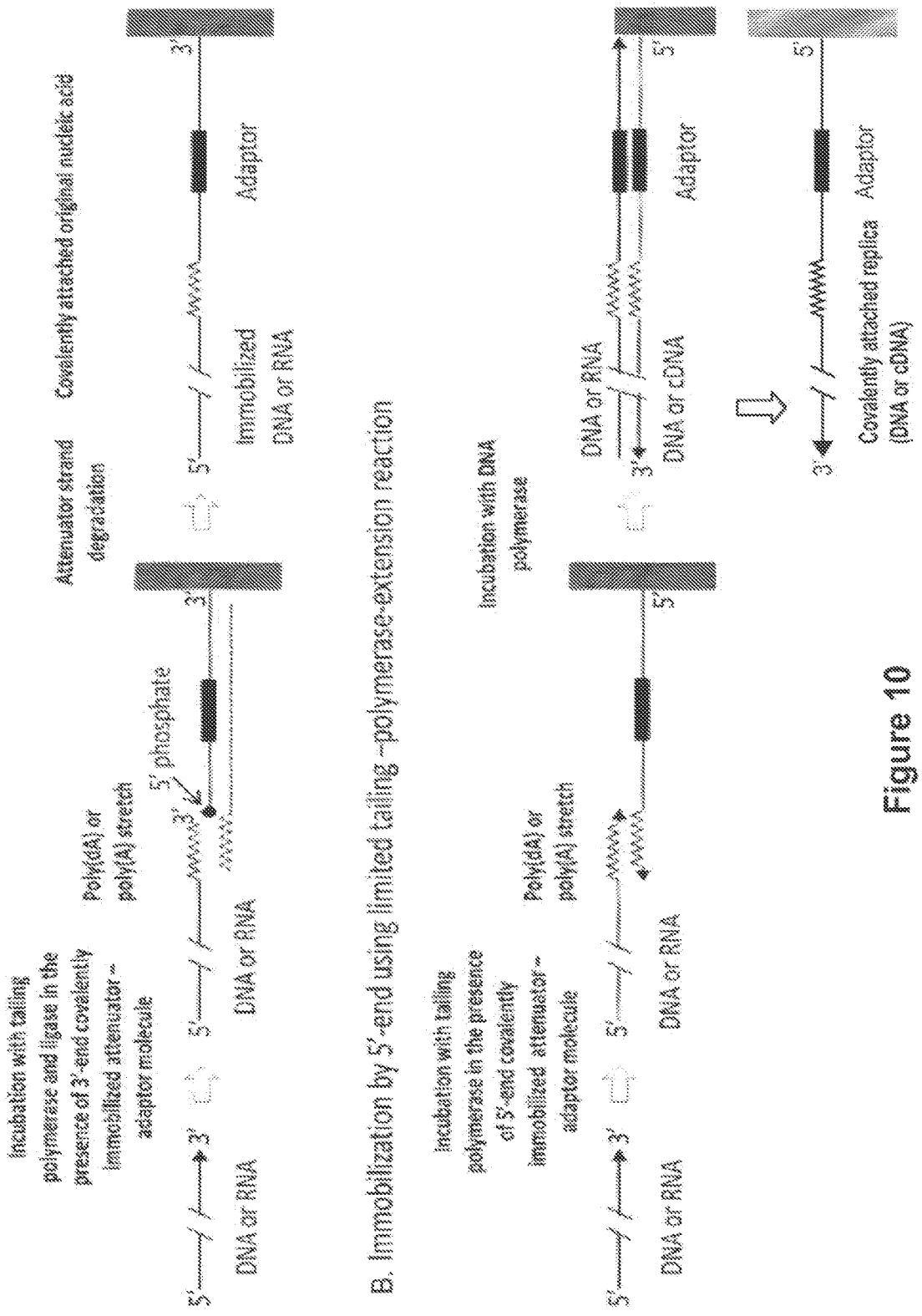
FIG. 10 depicts covalent immobilization of single-stranded DNA and RNA to a solid support using either (A) a coupled limited tailing-ligation reaction or (B) a limited tailing-polymerase extension reaction.

In a further aspect of the disclosure is provided a method for covalent immobilization of single-stranded DNA and RNA to a solid support using a limited tailing reaction (FIG. 10). Part A of FIG. 10 depicts immobilization by 3'-end using a limited tailing-ligation reaction. In such a reaction, a DNA or RNA molecule is incubated with a template-independent polymerase and a ligase in the presence of a 3'-end covalently immobilized attenuator-adaptor molecule that is partially double stranded, where the 3' end blocked single-stranded poly(T) or poly(dT) portion serves as an attenuator and the 5' phosphorylated double stranded portion serves as an adaptor. A limited poly(dA) or poly(A) stretch is then added to the substrate by a template-independent polymerase and the substrate forms a duplex with the single stranded portion of the attenuator-adaptor. The adaptor portion of the immobilized attenuator-adaptor is then ligated to the attenuated substrate polynucleotide via the 5' phosphate present on the adaptor molecule resulting in an immobilized DNA or RNA molecule. The controlled tailing, ligation and immobilization reactions occur in a closed-tube format.

Part B of FIG. 10 depicts immobilization by 5'-end using limited tailing-polymerase-extension reaction, which is a further aspect of the disclosure. In such a reaction, a DNA or RNA molecule is incubated with a template-independent polymerase in the presence of a 5'-end covalently immobilized attenuator-adaptor molecule. A poly(dA) or poly(A) stretch is then added by a template-independent polymerase, and the presence of a DNA polymerase allows for extension across the DNA or RNA molecule, thereby creating an immobilized double stranded product. The controlled tailing, extension and immobilization reactions can be done in a closed-tube format. In this case the dNTP mix must include heat-activatable dTTP, dCTP and dGTP (CleanAmp nucleotides, TriLink Bio Technologies, San Diego) and standard dATP, and the 3' end of an immobilized single stranded attenuator-adaptor must also contain a heat-activated base. As a result, controlled attenuated tailing would occur at 37° C. when only dATP is available and the other nucleotides and 3' end of the immobilized attenuator-adaptor remain blocked. After heating the mixture at 95° C., the remaining nucleotides become activated and the 3' end of the immobilized attenuator-adaptor becomes extendable.

In some aspects, in the case of DNA substrates, simultaneous tailing-ligation reactions (FIG. 9, part A, and FIG. 10, part A) will involve a TdT enzyme and E. coli DNA ligase (without being bound by theory, it is contemplated that in some embodiments, the ATP required for T4 DNA ligase would block a TdT-tailing process). In the case of RNA substrates, simultaneous tailing-ligation reactions (FIG. 9, part A, and FIG. 10, part A) involves poly(A) and T4 DNA ligase or poly (U) polymerase. In some aspects, however, the presence of ATP results in mixed poly(U/A) tailing.

In the case of DNA substrates, tailing-extension reactions (FIG. 9, part B and FIG. 10, part B) are executed by a TdT enzyme and a mesophilic or thermophilic DNA polymerase. In the case of RNA substrates, tailing-extension reactions (FIG. 9, part B and FIG. 10, part B) are executed by poly(A) or poly(U) polymerase and a DNA polymerase with reverse transcriptase activity. Polymerases contemplated for use in the methods and compositions of the disclosure have been described herein above.

Figure 11:
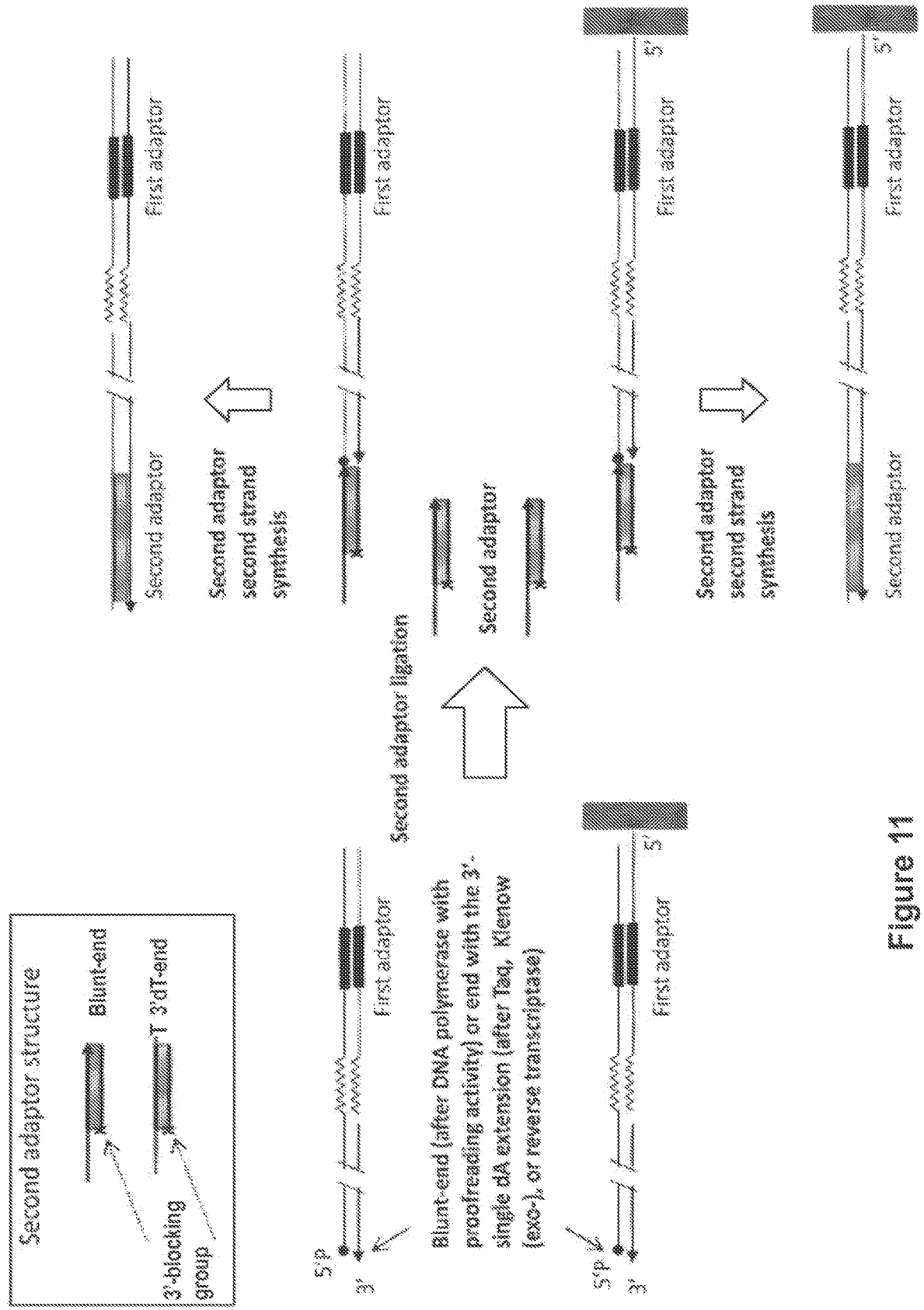
FIG. 11 depicts second adaptor attachment by blunt-end or dA/dT ligation.

Use of Controlled, Size-Limited Tailing for Adaptor Attachment to Both Ends of a DNA Library with and without Immobilization to a Solid Support In the case of adaptor ligation to double-stranded substrates (FIG. 11), the method involves a high concentration of a DNA ligase (for example and without limitation, T4 DNA ligase) and a blunt-end adaptor. Alternatively, the adaptor has a single dT-base 3'-overhang if the second DNA strand of the substrate nucleic acid was synthesized by a polymerase without 3' proofreading activity. In some aspects, such polymerases add an additional dA base to the 3' end of DNA.

Figure 12:
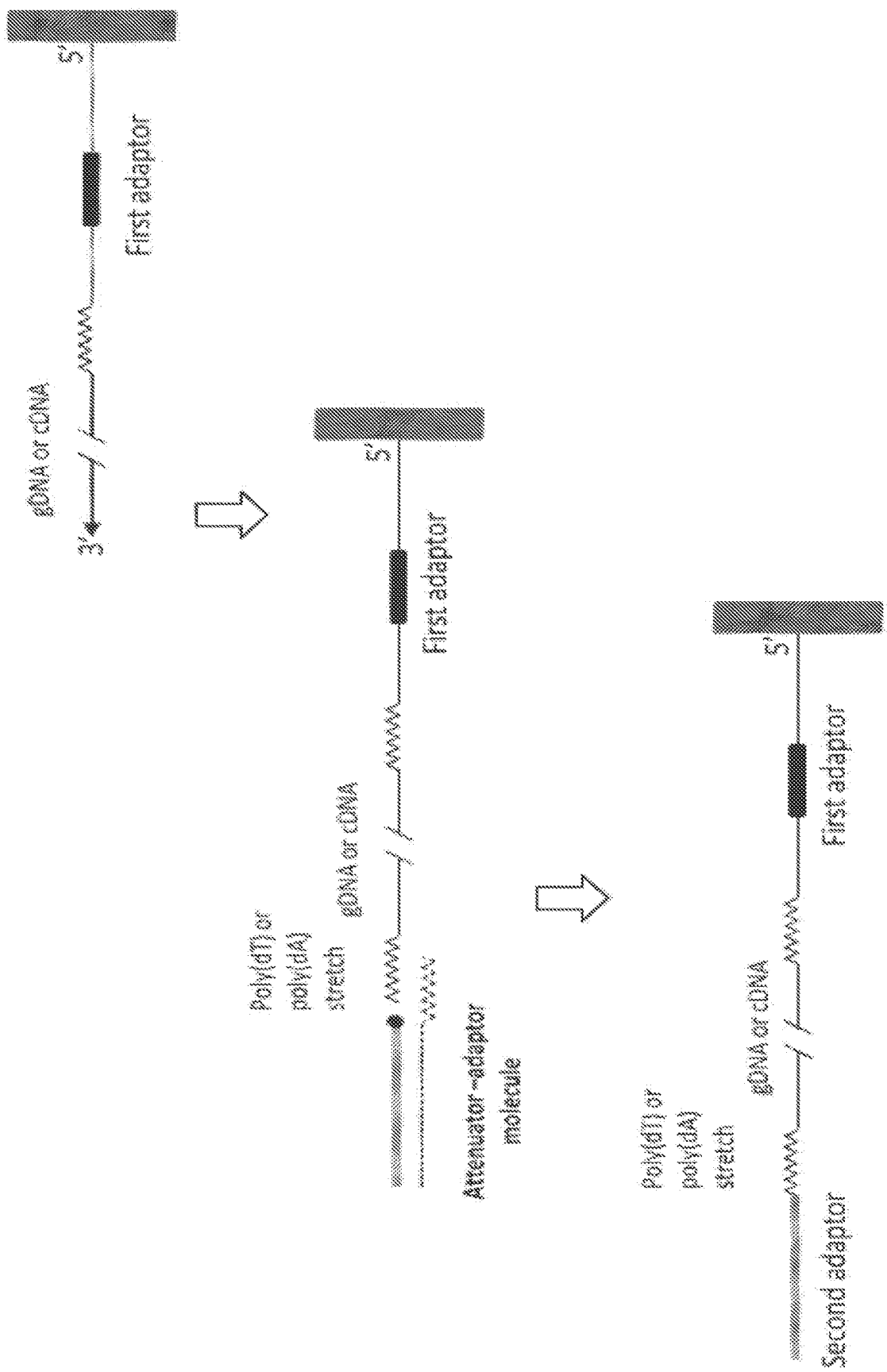
FIG. 12 depicts second adaptor attachment by a coupled limited tailing-ligation reaction. gDNA represents genomic DNA.
Figure 13:
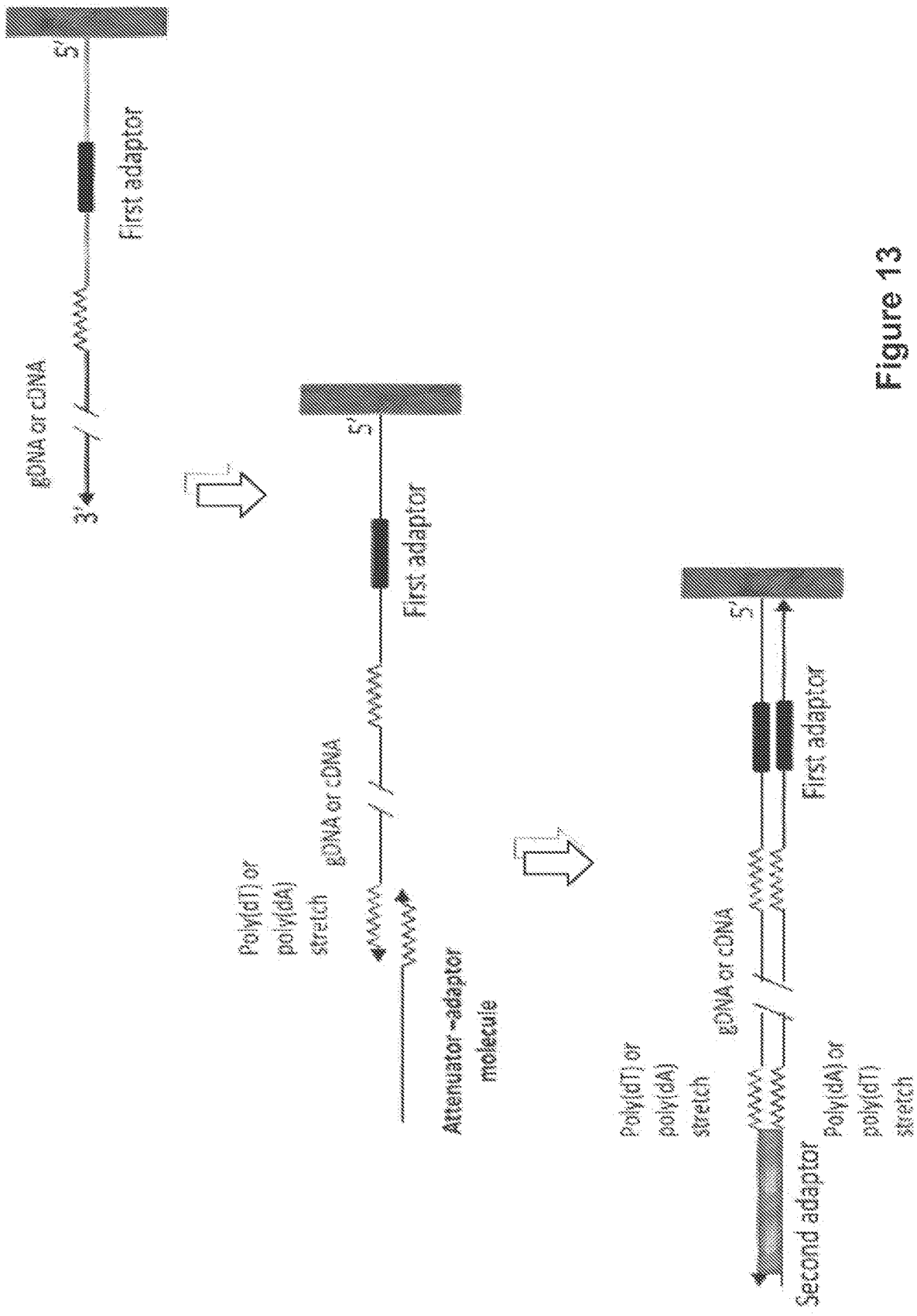
FIG. 13 depicts second adaptor attachment by a limited tailing-polymerase-extension reaction.

In the case of a single-stranded DNA substrate (such substrates can be covalently immobilized by their 5' end or through a biotin-streptavidin interaction as shown FIGS. 12 and 13, or may be free in solution), attachment of the second adaptor can involve processes shown in FIG. 9 that utilize limited tailing coupled either with the ligation process (FIG. 12) or with a polymerization process (FIG. 13).

Example 2

Figure 14:
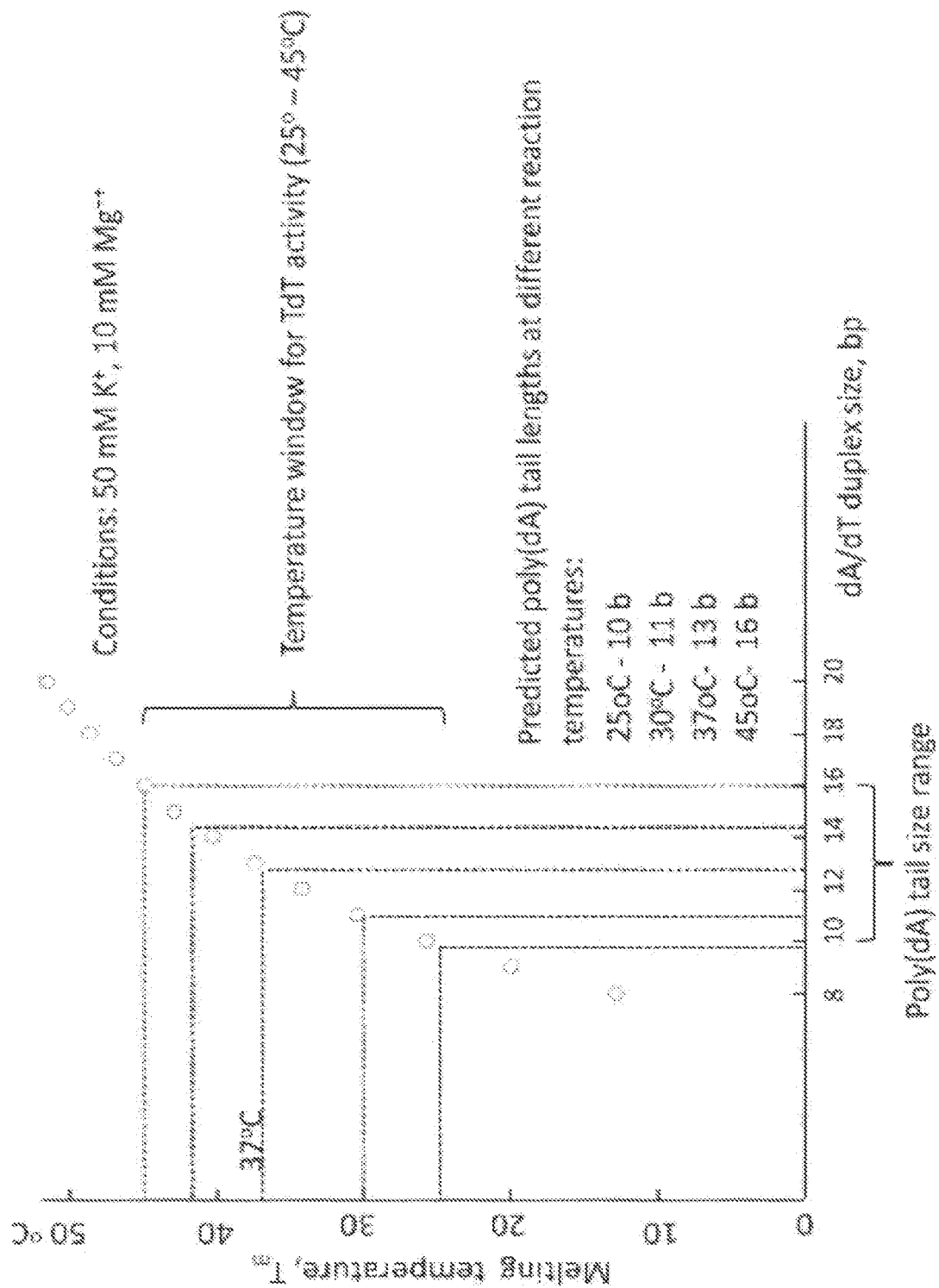
FIG. 14 depicts the predicted length of poly(dA) sequences introduced by a polymerase enzyme in the presence of a long poly(dT) attenuator molecule as a function of the reaction temperature. The Figure exemplifies, without limitation, using TdT enzyme for the tailing reaction.

Length of Poly(dA) Sequences Introduced by TdT Enzyme in the Presence of Long Poly(dT) Attenuator Molecule FIG. 14 shows the calculated dependence (open circles) between the length of the poly (dA)/poly (dT) duplex and its melting temperature, and it was concluded that the expected size of the attenuated poly(dA) tail varies as a function of the reaction temperature but is limited by a range of 10-16 bases.

Controlled Poly(dA) Tailing of Single-Stranded DNA Polynucleotide Template by TdT Enzyme in the Presence of a Long (Degradable) Attenuator Molecule
Materials:

---

Substrate polynucleotide 10-001 (Table 1)
Long degradable attenuator polynucleotide 10-103 (Table 2)
DNA polynucleotide size marker: equimolar mix of 5 polynucleotides 10-001, 10-099, 10-100, 10-101 and 10-102 (Table 4)
TdT enzyme (New England BioLabs, Cat # M0315S, 20 U/µl)
1 × TdT buffer: 20 mM Tris-acetate, 50 mM potassium acetate, 10 mM Mg-acetate, 0.25 mM $CoCl_2$, pH 7.9 at 25° C.
USER enzyme (New England BioLabs, Cat # M5505S, 1 U/µl)

---

Method: Poly(dA) tailing reactions were performed in 5 pi reaction volumes, containing 1×TdT buffer, 0.1 mM dATP, 4 pmol of the substrate polynucleotide 10-001, 10 U TdT enzyme and 0 or 20 pmol of the attenuator polynucleotide 10-103 at 37° C. for 1, 5, 15, 30, and 60 minutes, followed by 10 min incubation at 70° C. to inactivate the TdT enzyme. 0.25 U of the USER enzyme were added and incubated 5 minutes at 37° C. Samples were boiled in formamide loading buffer and run on a pre-casted 15% TBE-Urea polyacrylamide gel (Invitrogen, Cat #EC68852Box), stained with SYBR Gold stain (Invitrogen, Cat #S11494), visualized on a Dark Reader light box (Clare Chemical Research), and photographed using a digital camera.

Figure 15:
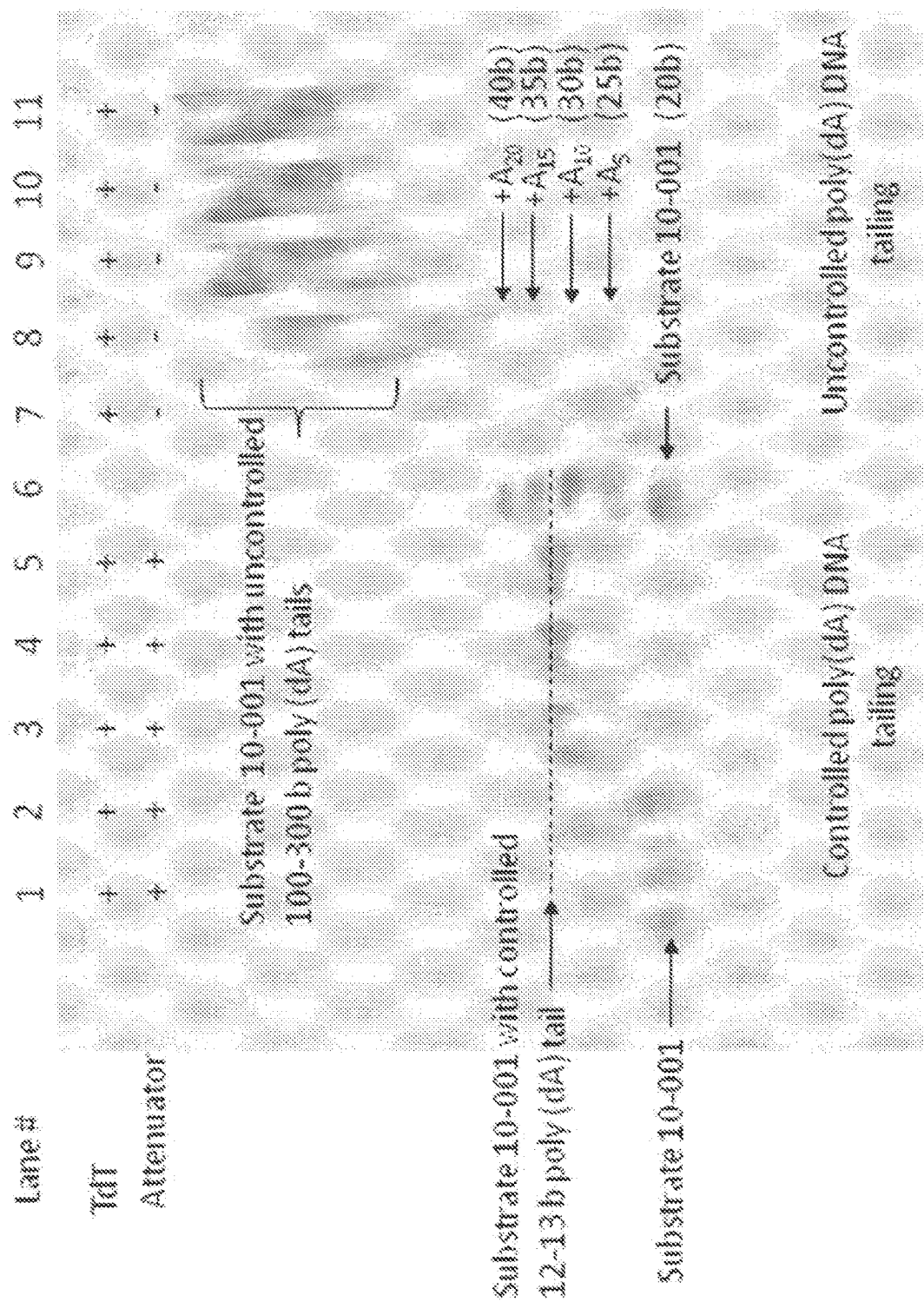
FIG. 15 shows an experimentally determined time course of poly(dA) tailing of single-stranded DNA template by TdT enzyme in the absence and in the presence of long degradable DNA attenuator molecule (TTTTTU)6TTT (SEQ ID NO: 43).

Results: Electrophoretic analysis of products of standard and attenuated poly(dA) tailing reactions by the TdT enzyme are shown on FIG. 15. Lanes 1, 2, 3, 4 and 5 show the products of tailing reaction after 1, 5, 10, 15 and 30 minutes of incubation with TdT enzyme in the presence of attenuator 10-103; lanes 7, 8, 9, 10 and 11 show the products of tailing reaction after 1, 5, 10, 15 and 30 minutes of incubation with TdT enzyme in the absence of attenuator; lane 6—DNA polynucleotide size marker. In both cases the tailing reaction was completed within 30 minutes. In the absence of attenuator molecule the TdT enzyme added to the substrate polynucleotide very long and heterogeneous in size poly(dA) tails. In the presence of the attenuator molecule, the size of the added poly(dA) tails was very discrete, its distribution was very narrow, with a maximum at about 12-13 bases (long attenuator molecule degraded by USER enzyme was not visible on the gel because degradation products did not exceed 5 bases). It is interesting to note that the melting temperature (or stability) of the complex formed by the attenuator molecule 10-103 and the poly(dA) tail containing 13 dA bases (SEQ ID NO: 66) was about 37.6° C., that is very close to the reaction temperature 37° C. The absence of any products with tails exceeding 13 bases indicated that the addition of dA bases was strongly inhibited by the attenuator molecule above this limit.

Conclusions: Complete attenuation of the poly(dA) tailing was achieved using long (40 b) poly (dT) molecules (SEQ ID NO: 85). The length of poly(dA) tails added by the TdT enzyme in the presence of long attenuator molecules constituted about 12-13 dA bases with extremely narrow size distribution contrasting several hundred dA bases added in the absence of attenuator molecules. Attenuator molecules containing dU bases were degraded after completion of the tailing reaction using USER enzyme to simplify downstream utilization of the dA-tailed DNA substrates.

Example 3

Controlled Poly(dA) Tailing of Single-Stranded DNA Polynucleotide Template by TdT Enzyme in the Presence of a Short Attenuator Molecule Materials:

Substrate polynucleotide 10-001 (Table 1)
Short attenuator polynucleotides: 10-130, 10-131, 10-132, 10-133, 10-134 and 10-135 (Table 2)
Two ribo-U nucleotides at the ends of short attenuator molecules were added to prevent tailing of the attenuator molecules by the TdT enzyme
Long degradable attenuator polynucleotide 10-103 (Table 2)
DNA polynucleotide size marker: equimolar mix of polynucleotides 10-001, 10-099, 10-100, 10-101 and 10-102 (Table 4)

25 bp ladder DNA size marker (Invitrogen, Cat # 10488-022)
TdT enzyme (New England BioLabs, Cat # M031S, 20 U/µl)
1 × TdT buffer: 20 mM Tris-acetate, 50 mM potassium acetate, 10 mM Mg-acetate, 0.25 mM $CoCl_2$, pH 7.9 at 25° C.
USER enzyme (New England BioLabs, Cat # M5505S, 1 U/µl)

Method: Poly(dA) tailing reactions were performed in 5 µl reaction volumes, containing 1×TdT buffer, 0.1 mM dATP, 4 pmol of the substrate polynucleotide 10-001, 10 U TdT enzyme, 60 pmol of the short attenuator polynucleotides 10-130-10-135 or 20 pmol of the long attenuator polynucleotide 10-103 at 30° C. for 30 minutes, followed by 10 minute incubation at 70° C. to inactivate the TdT enzyme. Controlled reactions with the substrate 10-001 were also conducted in the presence of the attenuator molecule 10-133 for 0, 30, 60, 90 and 120 minutes. 0.25 U of the USER enzyme was added to the tube containing the long attenuator molecule 10-103 and incubated 5 minutes at 37° C. Samples were boiled in formamide loading buffer and run on a pre-casted 15% TBE-Urea polyacrylamide gel (Invitrogen, Cat #EC68852Box), stained with SYBR Gold stain (Invitrogen, Cat #S11494), visualized on a Dark Reader light box (Clare Chemical Research), and photographed using a digital camera.

Figure 16A:
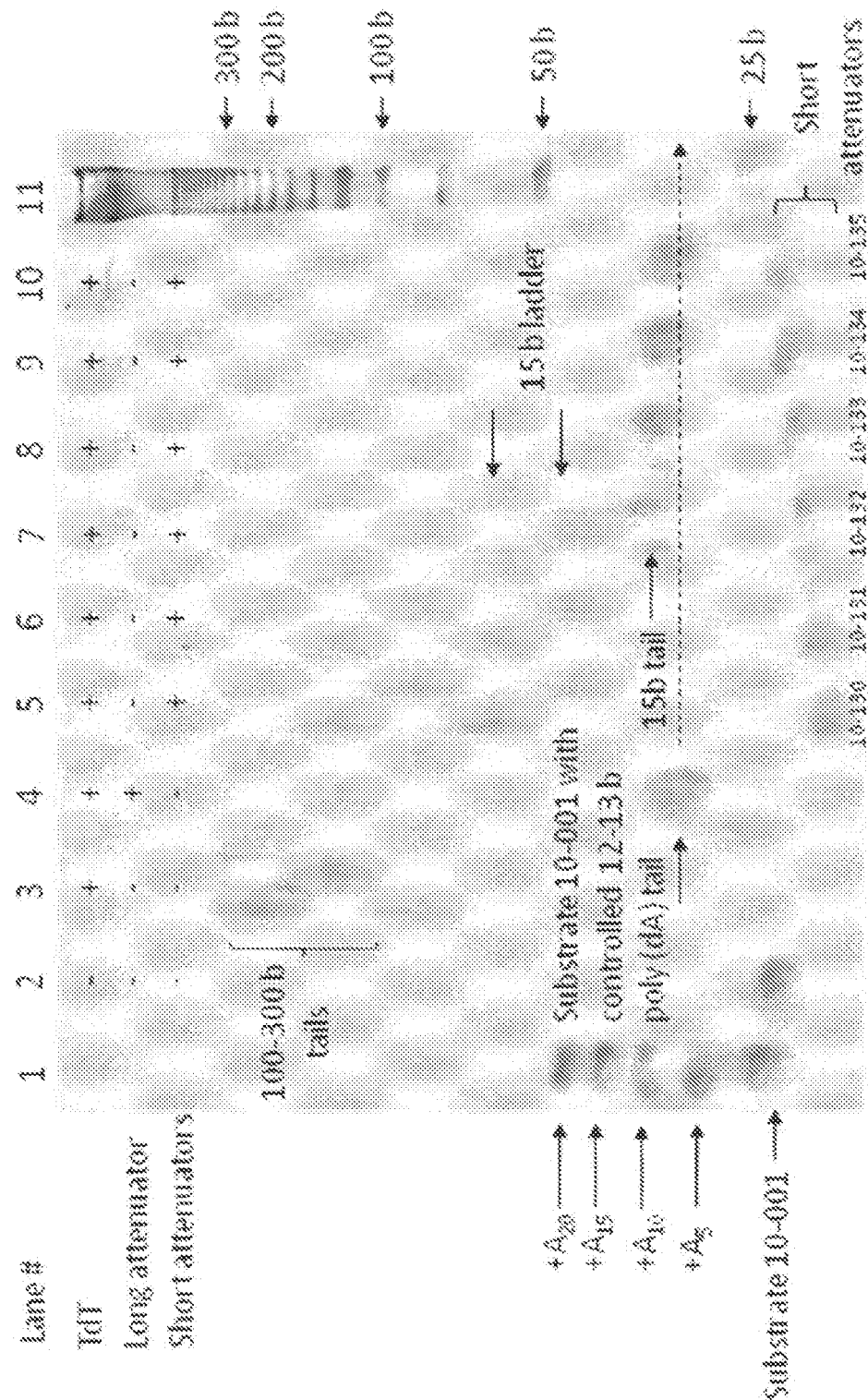
FIGS. 16A-B show controlled poly(dA) tailing of single-stranded DNA template by TdT in the presence of short attenuator molecules.
Figure 16B:
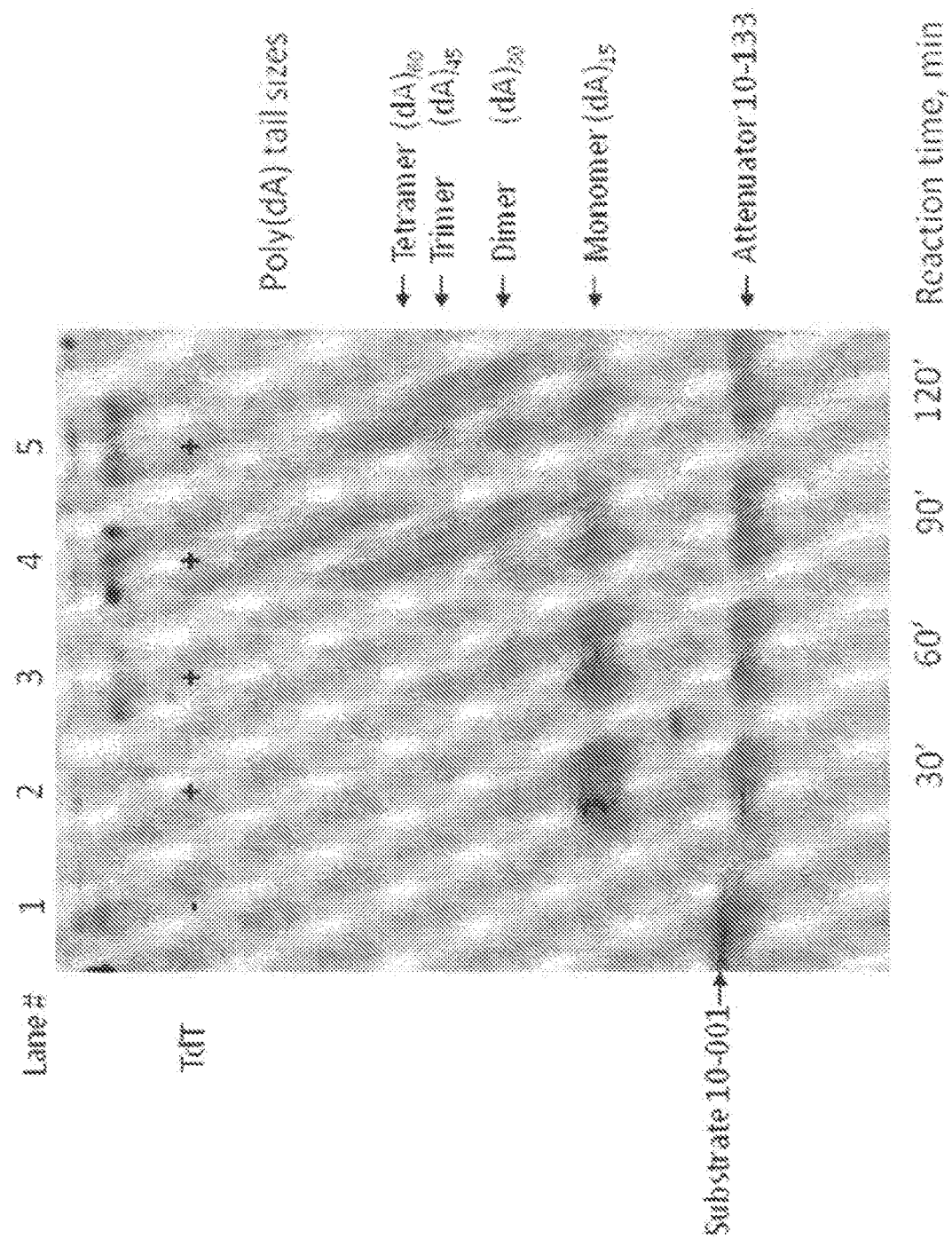

Results: Electrophoretic analysis of products of attenuated poly(dA) tailing reactions by the TdT enzyme using attenuator molecules of different length and stability are shown on FIG. 16a. Lane 2 shows untailed template polynucleotide-substrate 10-001, lanes 3-10—polynucleotide-substrate 10-1001 after TdT tailing. Lane 3 shows uncontrolled tailing product, lane 4—controlled tailing product in the presence of long attenuator molecule 10-103, and lanes 5, 6, 7, 8, 9, and 10—controlled tailing products on the presence of short attenuator molecules 10-130, 10-131, 10-132, 10-133, 10-134 and 10-135, respectively. Lanes 1 and 11 show DNA polynucleotide and 25 bp ladder size markers, respectively. FIG. 16b shows the kinetics of the tailing reaction in the presence of attenuator molecule 10-133, lane 1—substrate 10-001, lanes 2, 3, 4, and 5—tailing products after incubation with the TdT enzyme for 30, 60, 90, and 120 min, respectively. As in Example 2, in the presence of long attenuator molecule 10-103 the size of added poly(dA) tails was very discrete, its distribution was very narrow, with mean value at about 12-13 bases. The effect of short attenuator molecules was more complex and depended on their size. Attenuator molecules 10-130 and 10-131 with T7 rUrU and T8 rUrU stretches (SEQ ID NO: 88) (capable of forming complexes with the poly (dA) tail with melting temperatures Tm, =14.5° C. and 10° C., respectively) only slightly reduced the average size of poly(dA) tails while their size distribution still remained very broad (FIG. 16a, lanes 5 and 6). Attenuator molecule 10-132 with a T9 rUrU stretch (SEQ ID NO: 89), capable of forming a complex with the poly (dA) tail with melting temperature Tm=24.7° C., produced a predicted ladder of bands with an increment of approximately 15 bases (FIG. 16a, lane 7). The ladder became more prominent when incubation time was increased up to 90-120 minutes as seen from FIG. 16b, lanes 4 and 5. Such kinetics of attenuated tailing with short attenuator molecules was theoretically predicted and discussed herein. Attenuator molecules 10-133, 10-134 and 10-135 (capable of forming complexes with the poly (dA) tail with melting temperatures Tm=28.6° C., 32° C. and 35° C., respectively) produced a single discrete band with a size that gradually decreased from 15 to 12 bases upon increase of the attenuator size (FIG. 16a, lanes 8-10). Attenuator molecule 10-135, with a total number of 14 bases, was capable of forming a complex with the poly(dA) tail with Tm=35° C. and had the same effect as the long 40-base attenuator molecule 10-103. 12-base length for poly (dA) tails (SEQ ID NO: 81) observed at reaction temperature 30° C. is one base lower than the 13-base size (SEQ ID NO: 73) observed at reaction temperature 37° C., in agreement with the expected increased stability of complexes of shorter length at the lower reaction temperature. Attenuator molecules 10-130-10-135 were seen at the bottom of gel shown in FIG. 16a, lanes 5-10).

Conclusions: Complete attenuation of the poly(dA) tailing was achieved using short (12-14 base) poly (dT) molecules (SEQ ID NO: 90) blocked at the 3' end by 1-2 ribonucleotides, a phosphate group or other modifications preventing TdT tailing of the attenuator molecule. The length of poly(dA) tails added by the TdT enzyme in the presence of attenuator molecules was controlled by the reaction temperature and the size of attenuator molecules. Attenuated poly(dA) tails have a very narrow size distribution (+/−1 base) with the mean value varying from 11 to 15 bases. Prolonged incubation with TdT in presence of attenuators containing approximately 12 dT bases (SEQ ID NO: 91) resulted in repeats with an increment of 12-15 dA bases (SEQ ID NO: 92).

Example 4

Both Controlled and Uncontrolled Poly(dA) Tailing of Double-Stranded DNA Polynucleotide Templates by TdT Enzyme is Inefficient and Displays Strong Sequence Bias
Materials:

Double-stranded DNA substrate with GC-rich blunt end formed by polynucleotides 10-105 and 10-106 (Table 1 and Table 5):
Double-stranded DNA substrate with AT-rich blunt end formed by polynucleotides 10-107 and 10-108 (Table 1 and Table 5):
Double-stranded DNA substrate with 3'-overhanging end (3 bases) formed by polynucleotides 10-105 and 10-109 (Table 1 and Table 5):
Double-stranded DNA substrate with 3'-recessed end (3 bases) formed by polynucleotides 10-105 and 10-110 (Table 1 and Table 5):

Method: Double-stranded DNA templates were prepared by annealing the polynucleotide pairs 10-105/10-106, 10-107/10-108, 10-105/10-109, and 10-105/10-110. Specifically, after boiling, the mixed polynucleotides were allowed to cool slowly to room temperature in 10 mM Tris-HCl containing 0.1 mM EDTA and 50 mM NaCl. Poly(dA) tailing reactions were performed in a 5 uL reaction volume containing 1×TdT buffer, 0.1 mM dATP, 1 pmol of the substrate polynucleotide pair 10-105/106, 105/109, 105/110, or 107/108, 10 U TdT enzyme, 0.5 t_IL of 2.5 mM CoC12, and 0 or 20 pmol of the attenuator polynucleotide 10-103 at 37° C. for 60 minutes, followed by 10 minutes of incubation at 70° C. to inactivate TdT enzyme. 0.25 U of the USER enzyme were added and incubated 5 minutes at 37° C. Samples were boiled in formamide loading buffer and run on a precast 15% TBE-Urea gel (Invitrogen Cat #EC68852BOX), stained with SYBR Gold (Invitrogen Cat #S11494), visualized on a Dark Reader light box (Clare Chemical Research), and photographed using a digital camera.

Figure 17:
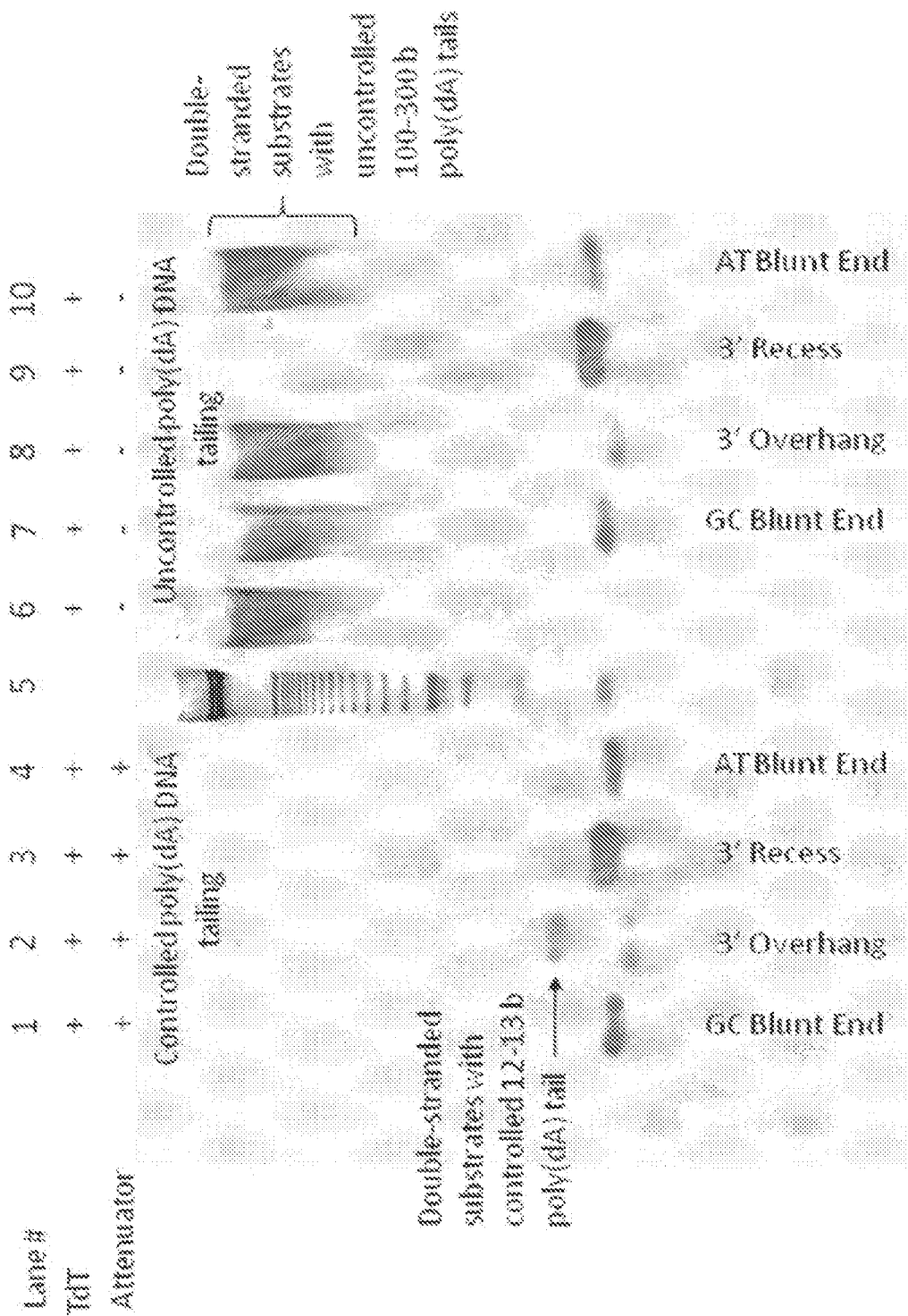
FIG. 17 shows controlled and uncontrolled poly(dA) TdT tailing of double-stranded DNA templates.

Results: Electrophoretic analysis of products of standard and attenuated poly(dA) tailing reactions by the TDT enzyme are shown in FIG. 17. Lanes 1-4 shows the tailing products in the presence of attenuator molecule, lanes 6-10—in the absence of attenuator molecule, lane 5—25 base pairs ladder size marker, lane 6—uncontrolled tailing of the single-stranded polynucleotide-substrate 10-001. All double-stranded templates exhibited less efficient TdT tailing than single-stranded templates. Double-stranded constructs with a 3' overhang (FIG. 17, lanes 2 and 8) were better templates for tailing reaction than double-stranded constructs with recessed end (FIG. 17, lanes 3 and 9) or blunt end (FIG. 17, lanes 1, 4, 7 and 10). The AT-rich blunt-ended construct (FIG. 17, lanes 4 and 10) was more efficiently tailed than the corresponding GC-rich construct (FIG. 17, lanes 1 and 7). Controlled tailing was more pronounced for the construct with the 3' overhang (FIG. 17, lane 2) although it did not go to completion.

Conclusions: Tailing of blunt-ended double stranded DNA (dsDNA) occurred much more slowly than tailing of dsDNA with a 3' overhang. AT rich blunt ends were tailed more efficiently than GC rich ends. Without wishing to be bound by theory, this may have been due to increased "breathing" of the 3' end of an AT rich sequence, allowing it to behave somewhat like single stranded DNA (ssDNA). Double stranded DNA (dsDNA) with a recessed end leads to little if any tailing. Controlled tailing can be observed and it is more efficient for double-stranded DNA molecules with the 3' single-stranded overhangs.

Example 5

Controlled Poly(dA) Tailing of Single-Stranded DNA Polynucleotide Templates by TdT Enzyme in the Presence of Attenuator Molecules Displays No Sequence Bias
Materials:

Substrate polynucleotide 10-001 (Table 1)
Substrate polynucleotide with random sequences 10-127, 128, 129, and 139 (Table 1)
Long degradable attenuator polynucleotide 10-103 (Table 2)

TdT enzyme (New England BioLabs, Cat# M0315S, 20 U/µl)
1 × TdT buffer: 20 mM Tris-acetate, 50 mM potassium acetate, 10 mM Mg-acetate, 0.25 mM CoCl₂, pH 7.9
USER enzyme (New England BioLabs, Cat# M5505S, 1 U/µl)

Method: Poly(dA) tailing reactions were performed in 5 iLit reaction volumes containing either 1×TdT buffer, 0.1 mM dATP, 4 pmol of the substrate polynucleotide 10-01, or 10-127, or 10-128, or 10-129, or 10-139 (or a mix of four polynucleotides 10-127, 10-128, 10-129, and 10-139), and 0 or 20 pmol of the attenuator polynucleotide 10-103 and then boiled for 3 minutes at 95° C. to ensure that all substrates were single-stranded. Ten units of TdT enzyme were added and the reaction mix was incubated at 37° C. for 30 minutes, followed by 10 min incubation at 70° C. to inactivate the TdT enzyme. 0.25 U of the USER enzyme were added and incubated for 5 minutes at 37° C. Samples were boiled in formamide loading buffer and run on a precast 15% TBE-Urea gel (Invitrogen Cat #EC68852BOX), stained with SYBR Gold (Invitrogen Cat #S11494), visualized on a Dark Reader light box (Clare Chemical Research) and photographed using a digital camera.

Figure 18:
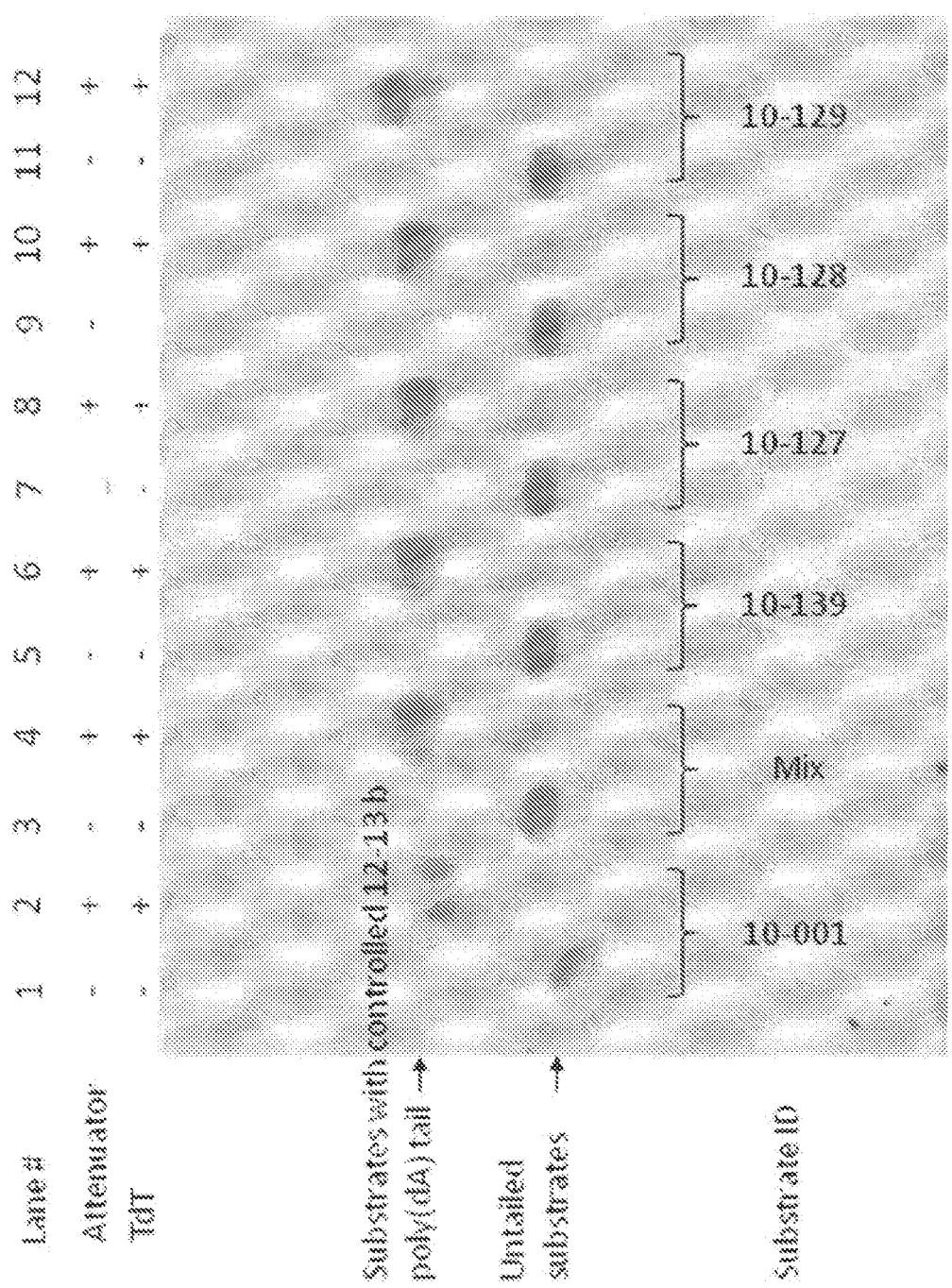
FIG. 18 shows controlled poly(dA) TdT tailing of single-stranded DNA templates with randomized ends.

Results: Electrophoretic analysis of products of standard and attenuated poly(dA) tailing reactions by the TDT enzyme are shown in FIG. 18. Lanes 1, 3, 5, 7, 9 and 11 show untailed template 10-1001, mixed template (see Methods), and templates 10-139, 10-127, 10-128 and 10-129, respectively; lanes 2, 4, 6, 8, 10 and 12 show controlled tailed template 10-1001, controlled tailed mixed template, and controlled tailed templates 10-139, 10-127, 10-128 and 10-129, respectively. All of the randomized polynucleotide-substrates are tailed similar to the non-random substrate 10-001.

Conclusions: TdT enzyme does not exhibit sequence bias during controlled poly (dA) tailing of single-stranded DNA substrates in the presence of attenuator molecules.

Example 6

Controlled Poly(dT), Poly(dC), Poly(dG) Tailing of Single-Stranded DNA Polynucleotide Template by TdT Enzyme in the Presence of Attenuator Molecules
Materials:

Substrate polynucleotide 10-085 (Table 1)
Attenuator polynucleotides: 10-103, 10-136, 10-137, and 10-138 (Table 2)
25 bp ladder DNA size marker (Invitrogen, Cat #10488-022)
TdT enzyme (New England BioLabs, Cat # M0315S, 20 U/µl)
1 × TdT buffer: 20 mM Tris-acetate, 50 mM potassium acetate, 10 mM Mg-acetate, 0.25 mM CoCl$_2$, pH 7.9
USER enzyme (New England BioLabs, Cat# M5505S, 1 U/µl)

Method: Poly(dA), poly(dT), poly(dG) and poly(dC) tailing reactions were performed in 5 µL reaction volumes containing 1×TdT buffer, 0.1 mM of either dATP, dTTP, dGTP, or dCTP, 4 pmol of the substrate polynucleotide 10-185 and 0 or 20 pmol of the attenuator polynucleotide 10-103, 10-136, 10-137, or 10-138, respectively. 10 U of the TdT enzyme were added and incubated at 37° C. for 30 minutes, followed by 10 minutes incubation at 70° C. to inactivate TdT enzyme. 0.25 U of the USER enzyme were added to the reaction containing 10-103 and incubated 5 mM at 37° C. Samples were boiled in formamide loading buffer and run on a precast 15% TBE-Urea gel (Invitrogen Cat #EC68852BOX), stained with SYBR Gold (Invitrogen Cat #S11494), visualized on a Dark Reader light box (Clare Chemical Research) and photographed using a digital camera.

Figure 19:
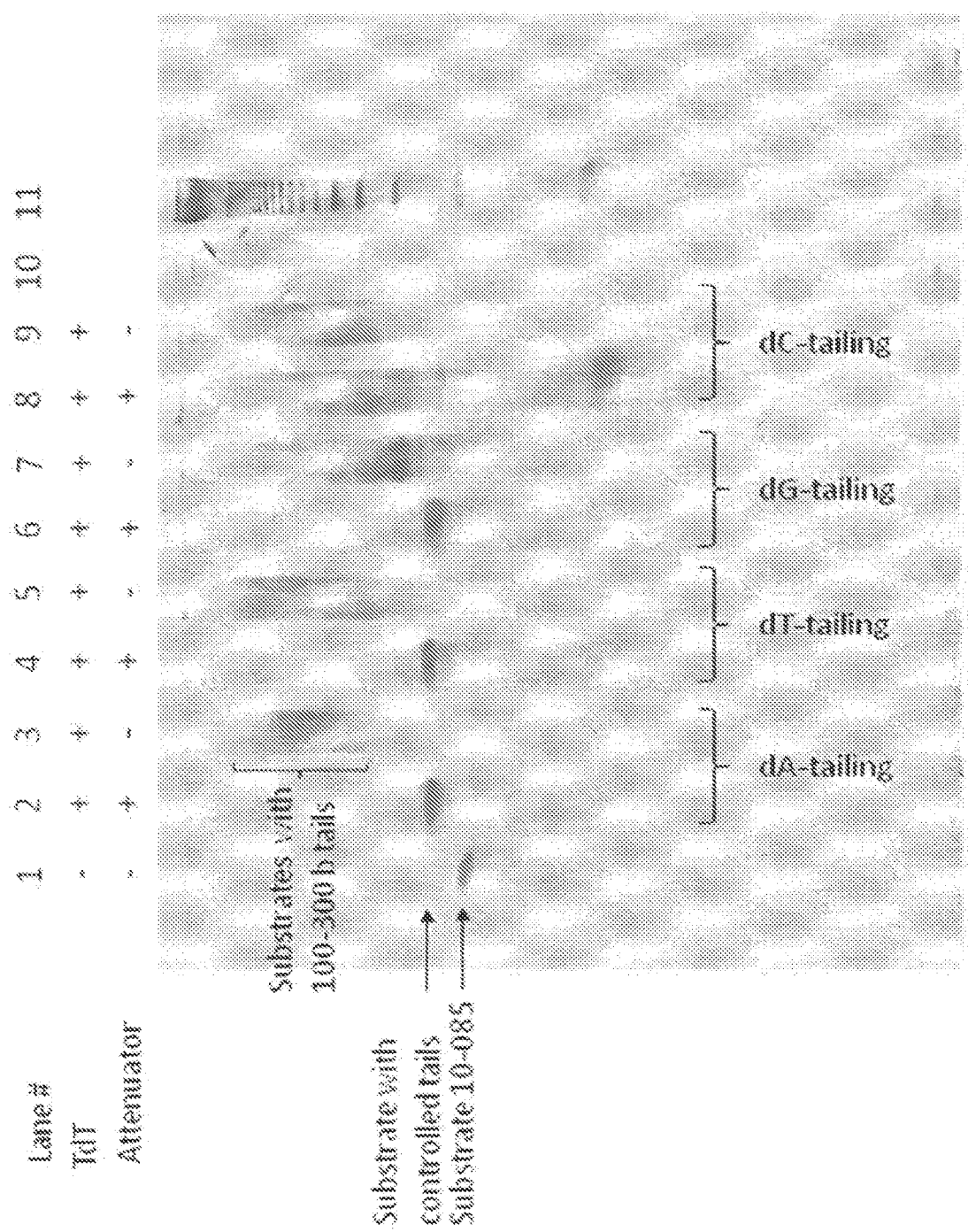
FIG. 19 shows controlled TdT tailing of single-stranded DNA templates with poly (dT), poly (dC) and poly (dG) tails.

Results: Electrophoretic analysis of products of standard and attenuated poly(dA), poly(dT), poly(dG) and poly(dC) tailing reactions by the TDT enzyme are shown in FIG. 19. Lane 1 shows untailed substrate polynucleotide 10-085; lanes 2, 4 6 and 8 show products of controlled tailing of the substrate 10-1085 by dA, dT, dG and dC nucleotides; lanes 3, 5 7 and 9 show products of uncontrolled tailing of the substrate 10-085 by dA, dT, dG and dC nucleotides; lane 11-25 by ladder DNA size marker. Controlled attenuated tailing with dT nucleotides in the presence of attenuator molecule 10-136 was undistinguishable from the controlled attenuated tailing with dA nucleotides in the presence of attenuator molecule 10-103. Both reactions produced sharp bands with the size of poly(dA) and poly(dT) tails around 12-13 bases (FIG. 19, lanes 2 and 4). Controlled attenuated tailing with dG nucleotides also produced a sharp band with the average size of poly(dG) tail around 10-12 bases which agreed with the higher stability of poly(dG/poly(dC) duplex. The attempt to control poly(dC) tailing was less successful and produced results that are difficult to interpret.

Conclusions: Attenuator-controlled poly(dA), poly(dT) and poly(dG) TdT tailing reactions behaved very similarly, resulting in efficient tailing of 100% of templates and adding a very short and accurate homopolymeric tail to the substrate DNA molecule. Tailing with the dA and the dT nucleotides produced tails of about 12-13 bases while tailing with dG nucleotides produced tails of about 10-12 bases. Controlled tailing with dC nucleotides was problematic due to difficulty of preparing and handling of attenuator polynucleotides containing long stretches (greater than 6) of dG-bases (for this reason dT bases were included into the attenuator 10-138).

Example 7

Controlled Poly(rA) Tailing of Single-Stranded RNA Polynucleotide Template by the *E. coli* Poly(A) Polymerase in the Presence of an Attenuator Molecule
Materials:

Substrate RNA polynucleotide 10-191 (Table 1)
Attenuator polynucleotide 10-103 (Table 2)
*E. Coli* poly(A)polymerase (New England BioLabs, Cat# M0276S. 5U/µl)
1 × Poly(A)polymerase buffer: 50 mM Tris-HCl, 250 mM NaCl, 10 mM MgCl$_2$, 1 mM ATP, pH 7.9
USER enzyme (New England BioLabs, Cat# M5505S, 1 U/µl)
Low Range ssRNA Marker (New England BioLabs, Cat# N0364S)
microRNA Marker: (New England BioLabs, Cat# N2102S)

Method: Reactions were carried out in a volume of 5 µL of 1× poly(A) polymerase buffer containing 4 pmols of substrate polynucleotide 10-191 and 0 or 20 pmols of attenuator polynucleotide 10-103, and 2.5 U of poly(A) polymerase. Reactions were performed at 30° C. (FIG. 20) for 5, 10, 15 or 30 minutes and then heated to 95° C. to inactivate the poly(A) polymerase. 0.5 U of USER enzyme were then added to the tubes containing attenuator molecules and incubated for 10 minutes at 37° C. Samples were then boiled in formamide loading buffer and run on a precast 15% TBE-Urea gel (Invitrogen Cat #EC68852BOX), stained with SYBR Gold (Invitrogen Cat #S11494), visualized on a Dark Reader light box (Clare Chemical Research) and photographed using a digital camera.

Figure 20:
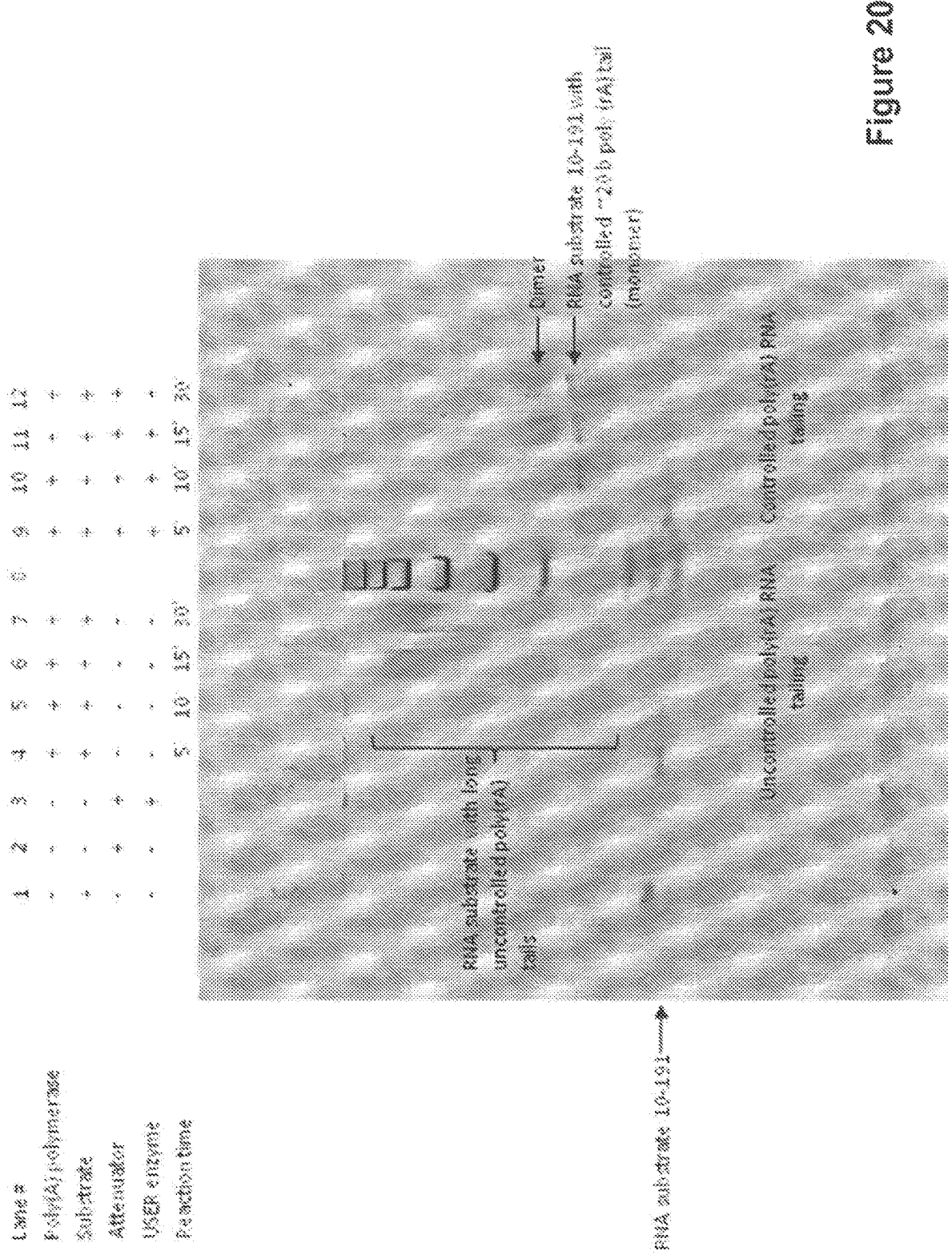
FIG. 20 shows controlled poly(rA) tailing of single-stranded RNA template by *E. coli* poly (A) polymerase.

Results: Electrophoretic analysis of products of standard and attenuated poly(rA) tailing of the RNA substrate polynucleotide 10-191 by poly(A) polymerase enzyme are shown in FIG. 20. Lanes 4, 5, 6 and 7 and lanes 9, 10, 11 and 12 show the tailing kinetics for 5, 10, 15 and 30 minutes of incubation with the poly(A) polymerase in the absence and in the presence of the attenuator molecule 10-103, respectively. Lanes 1, 2 and 3 show the RNA substrate 10-191, the attenuator polynucleotide 10-103 and the attenuator polynucleotide after incubation with the USER enzyme, respectively. Lane 8 shows a combination of the Low Range ssRNA Marker and the microRNA Marker. In both cases the tailing reaction was completed within 15 minutes. In the absence of the attenuator molecule the poly(A) polymerase added to the substrate polynucleotide very long and heterogeneous in size poly(rA) tails. In the presence of the attenuator molecule the size of added poly(rA) tails was substantially shorter with a very narrow band corresponding to the substrate with tail of approximately 20 bases (FIG. 20, lane 9). Long attenuator molecule was degraded by USER enzyme and was not visible on the gel because degradation products do not exceed 5 bases (FIG. 20, lanes 2 and 3). The dimer band, corresponding to the tail size of 40 bases was seen at longer incubation times (FIG. 20, lanes 10, 11 and 12). Larger size of controlled attenuated tails (20 b) introduced by the *E. coli* polymerase (A) comparing to tails added by the TdT enzyme (12-13 bases) and appearance of the dimer band in the presence of the same attenuator molecule 10-103 was explained by a lower thermal stability of the poly(rA)/poly(dT) duplex versus the poly(dA)/poly (dT) duplex.

Conclusions: Complete attenuation of poly(rA) tailing of the RNA templates was achieved using long DNA poly (dT) molecules. The length of poly(rA) tails added by the poly(A) polymerase in the presence of long attenuator molecules constituted about 20 rA bases with narrow size distribution contrasting several hundred rA bases added in the absence of attenuator molecules. Attenuator molecules containing dU bases were degraded after completion of the tailing reaction using USER enzyme to simplify downstream utilization of the rA-tailed RNA substrates. Attenuated tailing by poly(A) polymerase produced tails of approximately 20 bases, which can be efficiently used for RNA and microRNA analysis.

Example 8

Controlled Poly(rU) Tailing of Single-Stranded RNA Polynucleotide Template by the Yeast (S. pombe) Poly(U) Polymerase in the Presence of DNA and RNA Attenuator Molecules
Materials:

---

Substrate RNA polynucleotide 10-191 (Table 1)
Attenuator polynucleotide 10-136, 10-192 and 11-049 (Table 2), or High Molecular Weight poly(rA) (Midland Certified Reagent Company, Texas, Catalog # P3001)
RNA size ladder: 0.5 µl Low range ssRNA ladder (NEB N0364S) and 10 µl microRNA marker (NEB 2102S) combines with 10 µl formamide buffer
DNA size ladder: 25 bp ladder DNA size marker (Invitrogen, Cat #10488-022)
Yeast (S. pombe) poly(U) polymerase (New England BioLabs, Cat# M0337S, 2 U/µL)
1 × Poly(U)polymerase buffer: 10 mM Tris-HCL, 50 mM NaCl, 10 mM $MgCl_2$, 1 mM UTP, 1 mM DTT, pH 7.9
Formamide buffer: 97% Formamide, 10 mM EDTA, 0.01% bromophenol blue, 0.01% xylene cyanol

---

Method: Reactions were carried out in a volume of 5 uL of 1× poly(U) polymerase buffer containing 4 picomoles (pmols) of substrate polynucleotide 10-191 and 0 or 20 pmols of the DNA attenuator polynucleotides 10-136 and 10-192 or High Molecular Weight (HMW) RNA attenuator poly(rA) (average size about 200 b). Reactions were performed at either 37° C. (FIG. 21A) or 30° C. (FIG. 21B) for 10, 15 or 30 minutes. Reactions with RNA attenuator were prepared by adding 8 pmols of the substrate ribo-polynucleotide 10-191 and either 40 pmols of ribo-polynucleotide 11-049 or 41 ultrapure water to reaction tubes containing 1×NEB 2 buffer and 1 mM rUTP. To each tube, 2 U of NEB poly(U) polymerase was added and the reactions incubated at 30° C. (FIG. 7C) for 15 minutes. To stop the reactions, 10 ml of 2× formamide loading buffer was added to each tube, boiled and run on a precast 15% TBE-Urea gel (Invitrogen Cat #EC68852BOX), stained with SYBR Gold (Invitrogen Cat #S11494), visualized on a Dark Reader light box (Clare Chemical Research), and photographed using a digital camera.

Figure 21A:
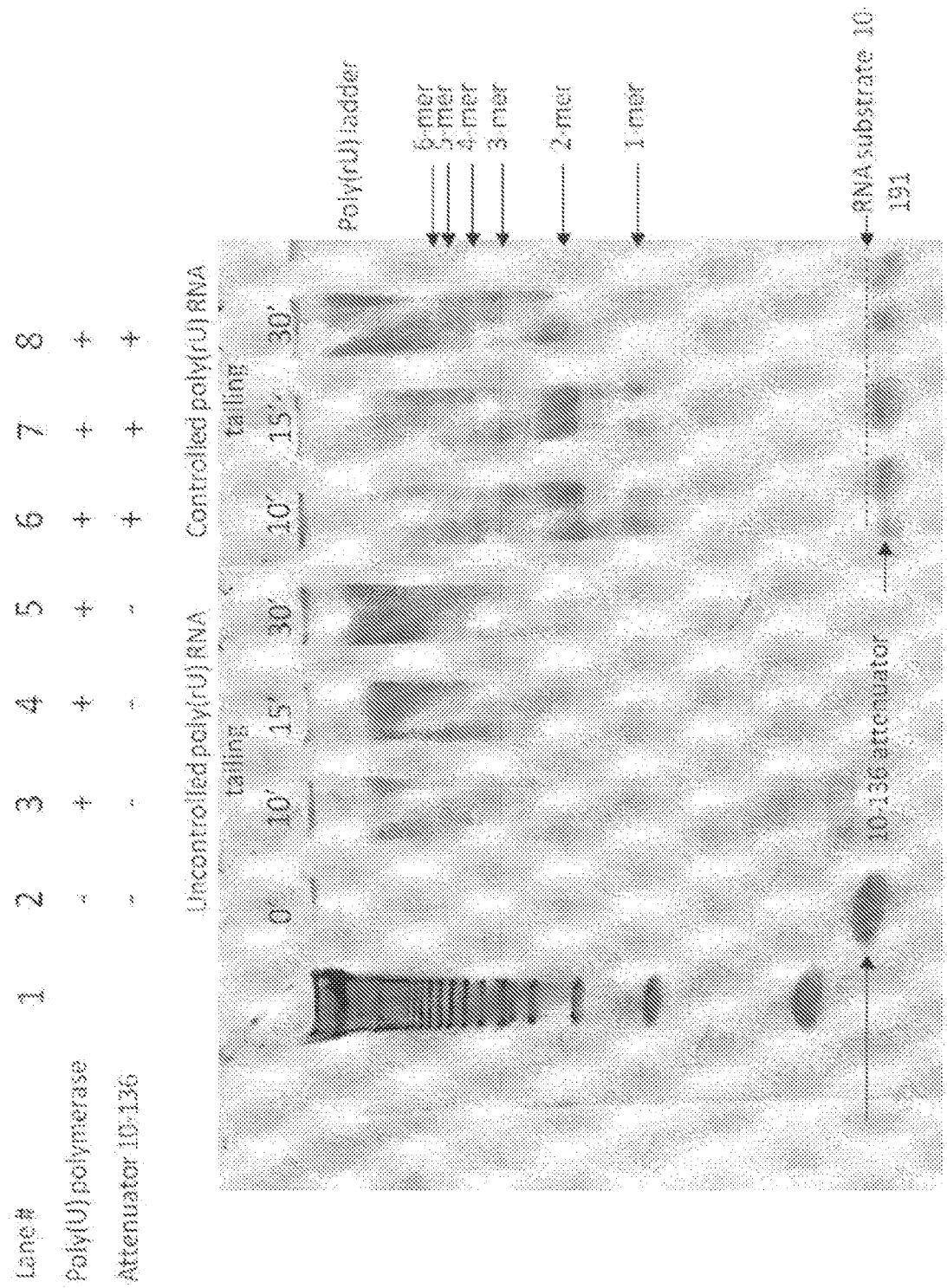
FIGS. 21A-C show controlled poly(rU) tailing of single-stranded RNA template by the yeast (*S. pombe*) poly (U) polymerase.
Figure 21B:
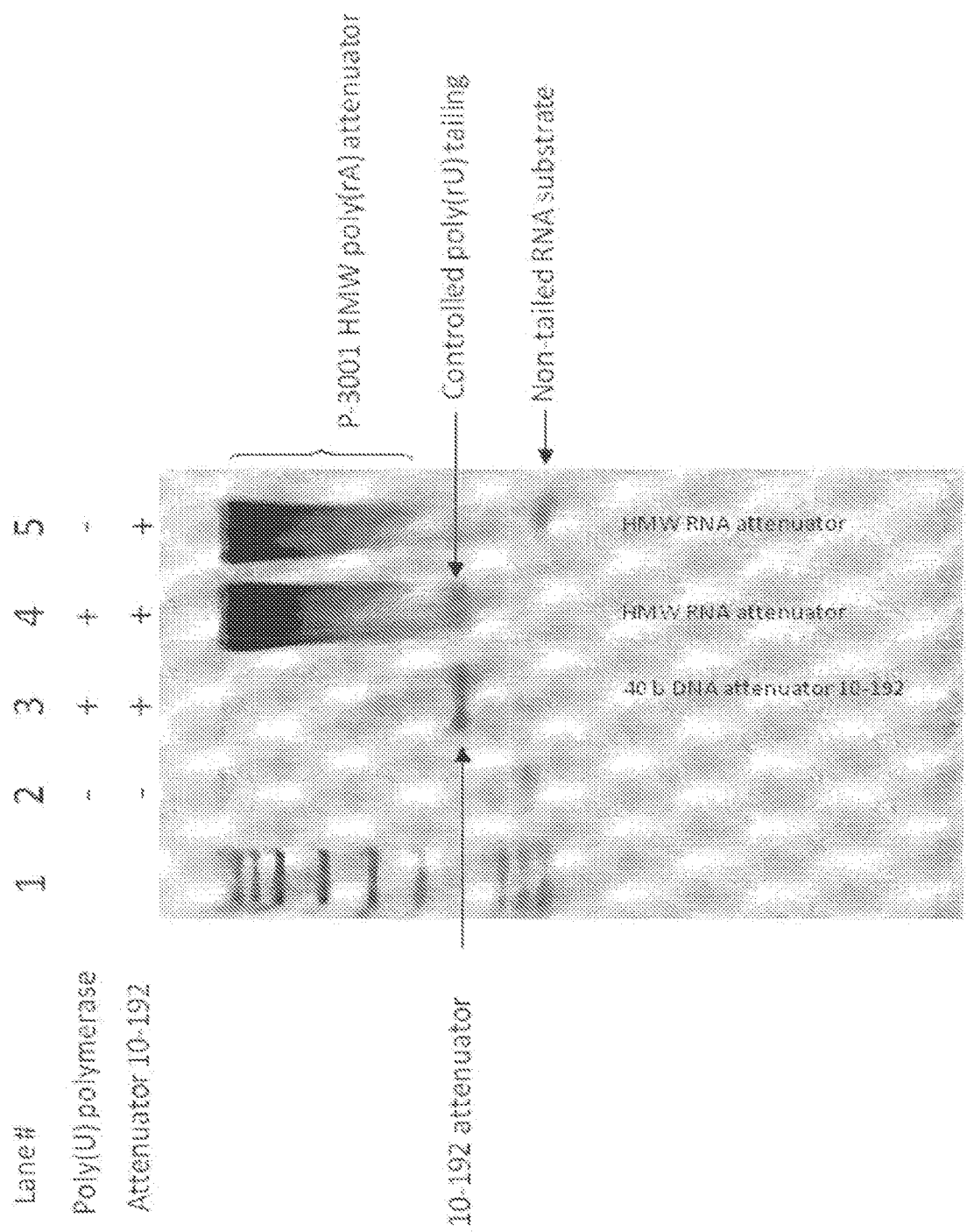
Figure 21C:
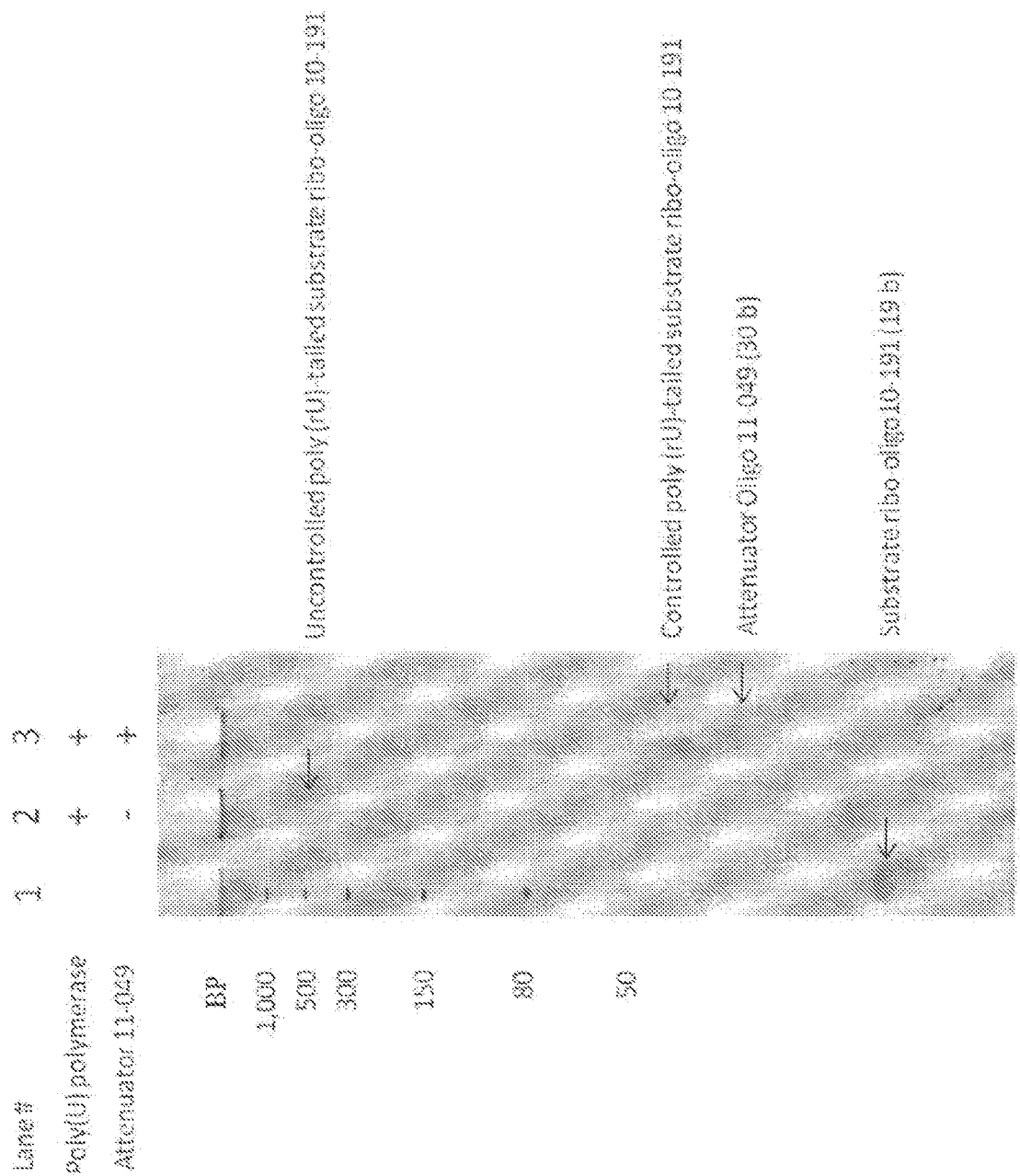

Results: Electrophoretic analysis of products of standard and attenuated poly(rU) tailing reactions by poly(U) polymerase enzyme are shown in FIG. 21a and FIG. 21b. FIG. 21a shows the time course of controlled (lanes 6, 7 and 8) and uncontrolled (lanes 3, 4 and 5) poly(U) tailing of the RNA substrate 10-191 for 10, 15 and 30 minute incubation times, respectively, in the presence of relatively short DNA attenuator polynucleotide 10-136 (20 b); lane 2—original RNA substrate 10-191; lane 1—25 bp ladder DNA size marker. FIG. 21b shows controlled tailing of the RNA substrate 10-191 (FIG. 21b, lane 2) in the presence of long 40 base DNA attenuator (FIG. 21b, lane 3) and High Molecular Weight poly(rA) RNA attenuator (FIG. 21b, lane 4). Lane 1 shows a combination of the Low Range ssRNA Marker and the microRNA Marker, lane 5—a mixture of the RNA substrate 10-191 and High Molecular Weight poly(rA) RNA attenuator. FIG. 20C shows controlled tailing of the RNA substrate 10-191 (lane 3) in the presence of long 30b RNA attenuator polynucleotide 11-049. As was seen from FIG. 21a, attenuated tailing in the presence of short DNA poly(dA)20 (SEQ ID NO: 21) attenuator resulted in a repetitive tailing pattern (ladder) that is indicative of the attenuation process working but the complete inhibition by 20-base DNA attenuator and narrow tail size distribution can't be achieved. Increasing the length of the DNA attenuator to 40 bases did improve the attenuation process and resulted in a single band that was broad (FIG. 21b, lane 3). It is known that poly(rU) and poly(dA) polymers form very unstable duplexes, while poly(rU) and poly(rA) form much more stable complexes. This was confirmed by using both High Molecular Weight poly(rA) and shorter ribo-polynucleotide (rA)30 (SEQ ID NO: 25) (11-049) as an attenuator for the poly(U) RNA tailing. As can be seen from FIG. 21b, lane 4, the tailing in the presence of long RNA attenuator resulted in a tailing product with very narrow size distribution and a tail size of about 20 bases (19 bases of substrate plus approximately 20 bases of poly(U) tail produce a molecule with about a size of 40 bases, similar to the size of the 40 base attenuator 10-192). Similar results were obtained using attenuator ribo-polynucleotide 11-049 (FIG. 21c lane 3) where poly(U)-tailed substrate ribo-polynucleotide 10-191 can be seen as a product of about 40 bases, suggesting that the size of the poly(U) tail is about 20 bases.

Conclusions: Controlled attenuated poly(U) tailing was achieved in the presence of DNA poly(dA) attenuators but it is much more efficient in the presence of RNA poly(rA) attenuators. Attenuated tailing by poly(U) polymerase produced tails of approximately 20 bases that are efficiently used for RNA and microRNA analysis.

Example 9

Simultaneous Controlled Poly(dA) Tailing and Attenuator-Adaptor Molecule Ligation to Single-Stranded DNA by Combined Action of TdT and E. coli DNA Ligase Enzymes
Materials:

---

Substrate polynucleotide 10-105 (Table 1)
Double stranded attenuator-adaptor formed by polynucleotides 10-211 and 10-212 (Table 3 and Table 6)
TdT enzyme (New England BioLabs, Cat# M0315S, 20 U/µl)
1 × TdT buffer: 20 mM Tris-acetate, 50 mM potassium acetate, 10 mM Mg-acetate, 0.25 mM $CoCl_2$, pH 7.9
E. coli DNA Ligase Enzyme (New England BioLabs, Cat# M0205S, 10 U/µL)

---

Method: The polynucleotides 10-211 and 10-212 were annealed together by boiling and then allowed to slowly cool to room temperature in 10 mM Tris-HCl containing 0.1 mM EDTA and 50 mM NaCl. Simultaneous poly(dA) tailing and attenuator-adaptor ligation reactions were performed in a 10 µL reaction volume containing 1×TdT buffer, 0.1 mM dATP, 26 uM NAD+, 4 pmol of the substrate polynucleotide and 20 pmol of the attenuator-adaptor molecule. 10 U TdT enzyme and either 0 or 10 U DNA ligase enzyme were added and incubated at 37° C. for 15 minutes. Samples were then boiled in formamide loading buffer and run on a precast 15% TBE-Urea gel (Invitrogen Cat #EC68852BOX), stained with SYBR Gold (Invitrogen Cat #S11494), visualized on a Dark Reader light box (Clare Chemical Research) and photographed using a digital camera.

Figure 22:
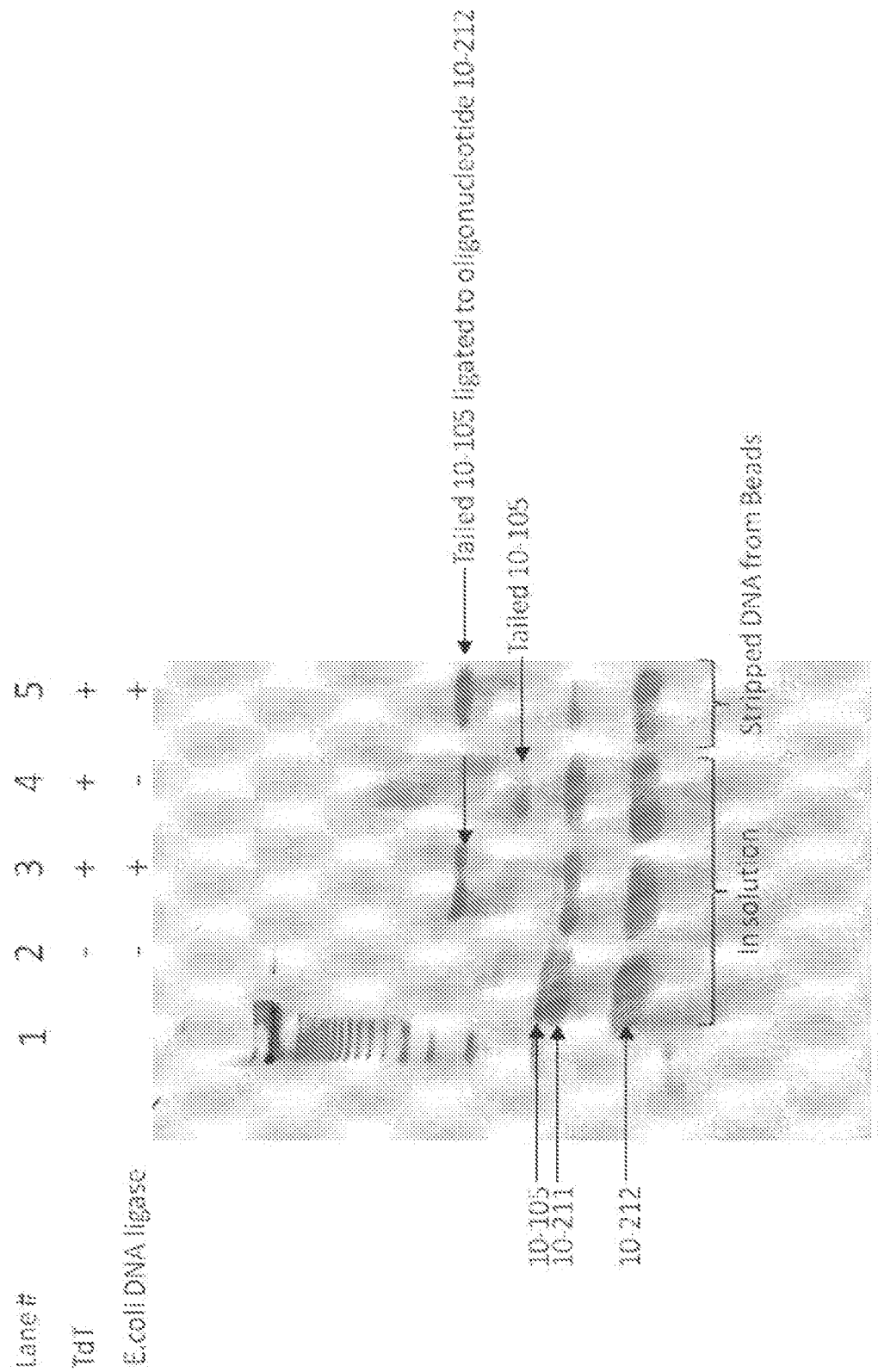
FIG. 22 shows simultaneous controlled DNA TdT tailing and ligation to attenuator-adaptor complex in solution and solid phase.
Figure 24A:
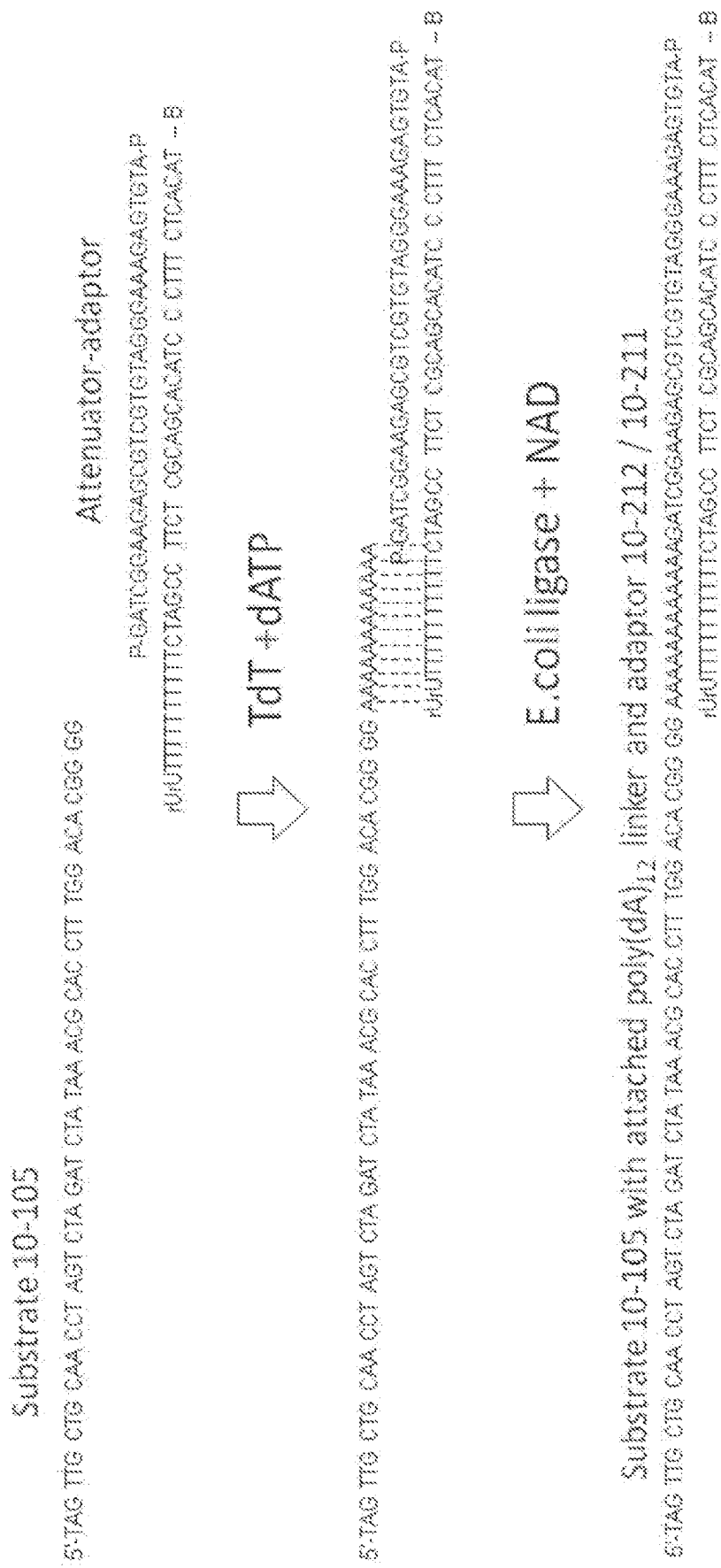
FIGS. 24A-C depict diagrams illustrating the process of simultaneous controlled tailing, ligation and immobilization of single-stranded DNA and RNA.

Results: Electrophoretic analysis of products of simultaneously attenuated TdT-mediated poly(dA) tailing and adaptor ligation reaction are shown in FIG. 22. Lane 1 represents the 25 bp ladder DNA marker, lane 2—the substrate and attenuator-adaptor molecules used in the reaction. Lane 3 shows the products of simultaneous tailing-ligation reaction, lane 4—the products of tailing reaction using attenuator-adaptor construct (no ligase). In the presence of TdT enzyme and E. coli ligase, the reaction resulted in a sharp band that is located between 75 and 100 base bands of the 25 base DNA ladder. The expected size of tailing and ligation product is 95 bases, which is very close to the size of the observed product (FIG. 22, lane 3, the largest band). The 50 base band corresponding to the non-reacted substrate is almost not visible in lane 4, indicating that efficiency of the attenuated tailing-ligation reaction is close to 100%. Data presented in lanes 4 (TdT only) and 5 (TdT and ligase) suggested that the reaction time used (15 minutes) is sufficient for adding a 12 base tail and attaching the adaptor but not sufficient to convert the substrate into a product with 12-13 added dA bases (SEQ ID NO: 86). Schematically the single-tube, single-step DNA tailing-ligation process is shown on FIG. 24a.

Conclusions: Poly(dA) tailing and subsequent ligation to the attenuator-adaptor molecule happened very quickly and efficiently when performed in parallel in a single sample tube. The reaction is used for efficient adaptation or tagging of random single-stranded DNA molecules in a single-tube, single-reaction format.

Example 10

Simultaneous Controlled Poly(dA) Tailing and Immobilization of Single-Stranded DNA by Combined Action of the TdT and DNA Ligase Enzymes and Use of Attenuator-Adaptors Immobilized to Magnetic Beads Materials:

Substrate polynucleotide 10-105 (Table 1)
Attenuator-adaptor formed by polynucleotides 10-211 and 10-212 (Table 3 and Table 6)
TdT enzyme (New England BioLabs, Cat# M0315S, 20 U/μl)
1 × TdT buffer: 20 mM Tris-acetate, 50 mM potassium acetate, 10 mM Mg-acetate, 0.25 mM $CoCl_2$, pH 7.9
E. coli DNA Ligase (New England BioLabs Cat# M0205S, 10 U/μL)
Dynabeads MyOne Streptavidin T1 (Invitrogen Cat#656.01)
Bead Wash Buffer: 5 mM Tris-HCl ph 7.5, 0.5 mM EDTA, 1M NaCl, 0.05% Tween-20

Method: The attenuator-adaptor complex was prepared as described in Example 9. 100 μL of Dynabeads were washed twice with bead wash buffer and then resuspended in 20 bead wash buffer. To the bead solution, 80 pmols of 10-211/212 annealed pair was added. Beads were incubated at room temperature on the orbital shaker (Nutator) for approximately 2 hours, then stored at 4° C. until needed. Immediately before running reactions, 5 μL of bead solution was transferred to a new tube, and washed twice with TdT buffer. Simultaneous poly(dA) tailing and attenuator ligation reactions were performed in 10 μL reaction volumes containing 1×TdT buffer, 0.1 mM dATP, 26 μM NAD+, 4 pmol of the substrate polynucleotide and 20 pmol of the attenuator-adaptor complex immobilized on the beads. 10 U TdT enzyme and either 0 or 10 U DNA ligase enzyme were added and incubated at 37° C. for 15 minutes. The beads were washed twice with deionized water and then with 10 μL of 125 mM NaOH to strip non-biotinylated ssDNA from the beads. DNA released by NaOH was neutralized and the remaining samples were then boiled in formamide loading buffer and run on a precast 15% TBE¬Urea gel (Invitrogen Cat #EC68852BOX), stained with SYBR Gold (Invitrogen Cat #S11494), visualized on a Dark Reader light box (Clare Chemical Research) and photographed using a digital camera.

Figure 24B:

Results: Electrophoretic analysis of products of simultaneously attenuated TdT-mediated poly(dA) tailing and ligation of the immobilized attenuator-adaptor are shown in FIG. 22, lane 5. The expected size of tailing and ligation product is 95 bases, which is very close to the size of the observed product (FIG. 22, lane 5, the largest band) and the product of tailing-ligation reaction described in Example 9 (lane 3). Intensities of 95 base pair bands in lanes 3 and 5 indicated that efficiency of the attenuated tailing-ligation-immobilization reaction was close to 100%. The strong band corresponding to polynucleotide 10-212 in lane 5 was due to the non-reacted adaptor which is present in excess. The immobilization process is shown in FIG. 24b.

Conclusions: Poly(dA) tailing and subsequent ligation to the immobilized attenuator-adaptor molecule happened very quickly and efficiently when performed in parallel in a single sample tube. The reaction is used for efficient adaptation, tagging and immobilization of random single-stranded DNA molecules in a single-tube, single-reaction format.

Example 11

Simultaneous Controlled Poly(rA) Tailing and Attenuator-Adaptor Molecule Ligation to Single-Stranded RNA by Combined Action of the Yeast Poly(A) Polymerase and T4 DNA Ligase Enzymes Materials:

Substrate polynucleotide 10-191 (Table 1)
Attenuator-adaptor formed by polynucleotides 11-010 and 11-011 (Table 3 and Table 6)
Yeast Poly(A) Polymerase (Affymetrix, 74225Y; 600 U/μl)
1 × TdT buffer: 20 mM Tris-acetate, 50 mM potassium acetate, 10 mM Mg-acetate, 0.25 mM $CoCl_2$, pH 7.9
T4 DNA Ligase (New England BioLabs, Cat# M0202T, 2,000,0000 end units/ml
Dynabeads MyOne Streptavidin T1 (Invitrogen Cat#656.01)
Bead Wash Buffer: 5 mM Tris-HCl ph 7.5, 0.5 mM EDTA, 1M NaCl, 0.05% Tween-20
5 × Poly(A) Polymerase Reaction Buffer (Affymetrix; 74226): 100 mM Tris-HCl pH 7.0, 3 mM $MnCl_2$, 0.1 mM EDTA, 1 mM Dithiotreitol, 500 ug/mL acetylated BSA, 50% Glycerol
TrackIt 25 bp Ladder: Invitrogen: 10488-022
Formamide buffer: 97% Formamide, 10 mM EDTA, 0.01% bromophenol blue, 0.01% xylene cyanol (made in-house)

Method: Reactions were prepared by adding 8 pmols of the substrate ribo¬oligonucleotide (10-191) and 40 pmols of attenuator/adaptor oligo pair (11-010/11-011) to reaction tubes containing 1× Poly(A) Polymerase reaction buffer and 1 mM rATP. To each tube 300 units of yeast poly(A) polymerase and 2,000 cohesive end units of T4 DNA ligase were added and the reactions incubated at 37° C. for 30 minutes. To stop the reaction 10 μL of 2× Formamide loading buffer was added to each tube and the reactions were boiled at 95° C. for 2 minutes. A 15% TBE-Urea gel was loaded with 25 by Ladder and 10 μL of each reaction. A current of 200 volts was applied to the gel for 30 minutes to separate the molecules and the gel was then stained with SYBR Gold for 10 minutes and then visualized on a Dark Reader light box (Clare Chemical Research) and photographed using a digital camera.

Figure 23:
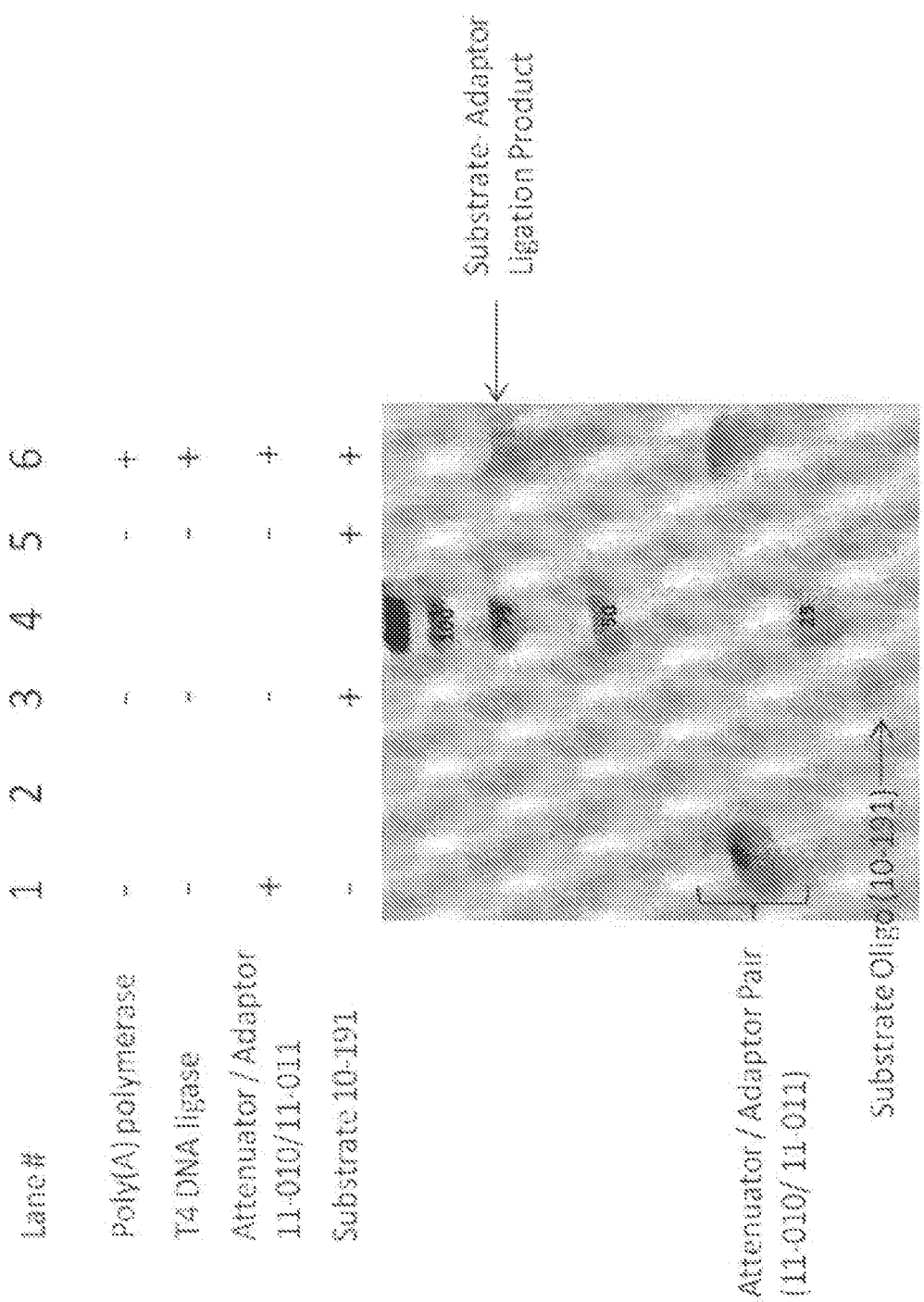
FIG. 23 shows experimental data illustrating simultaneous controlled poly(A) polymerase tailing and ligation of single-stranded RNA template to attenuator-adaptor complex in solution.
Figure 24C:
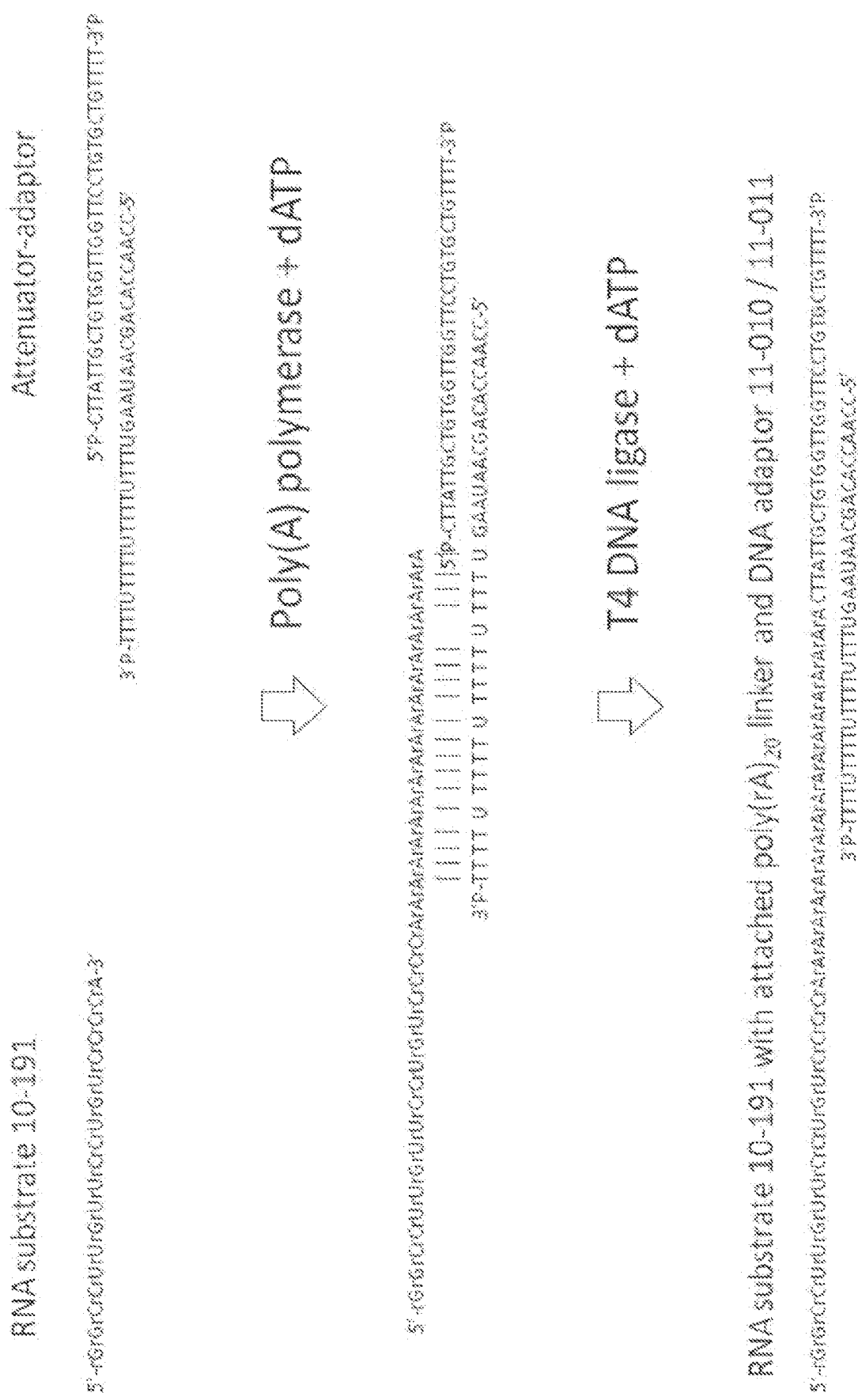
Figure 25:
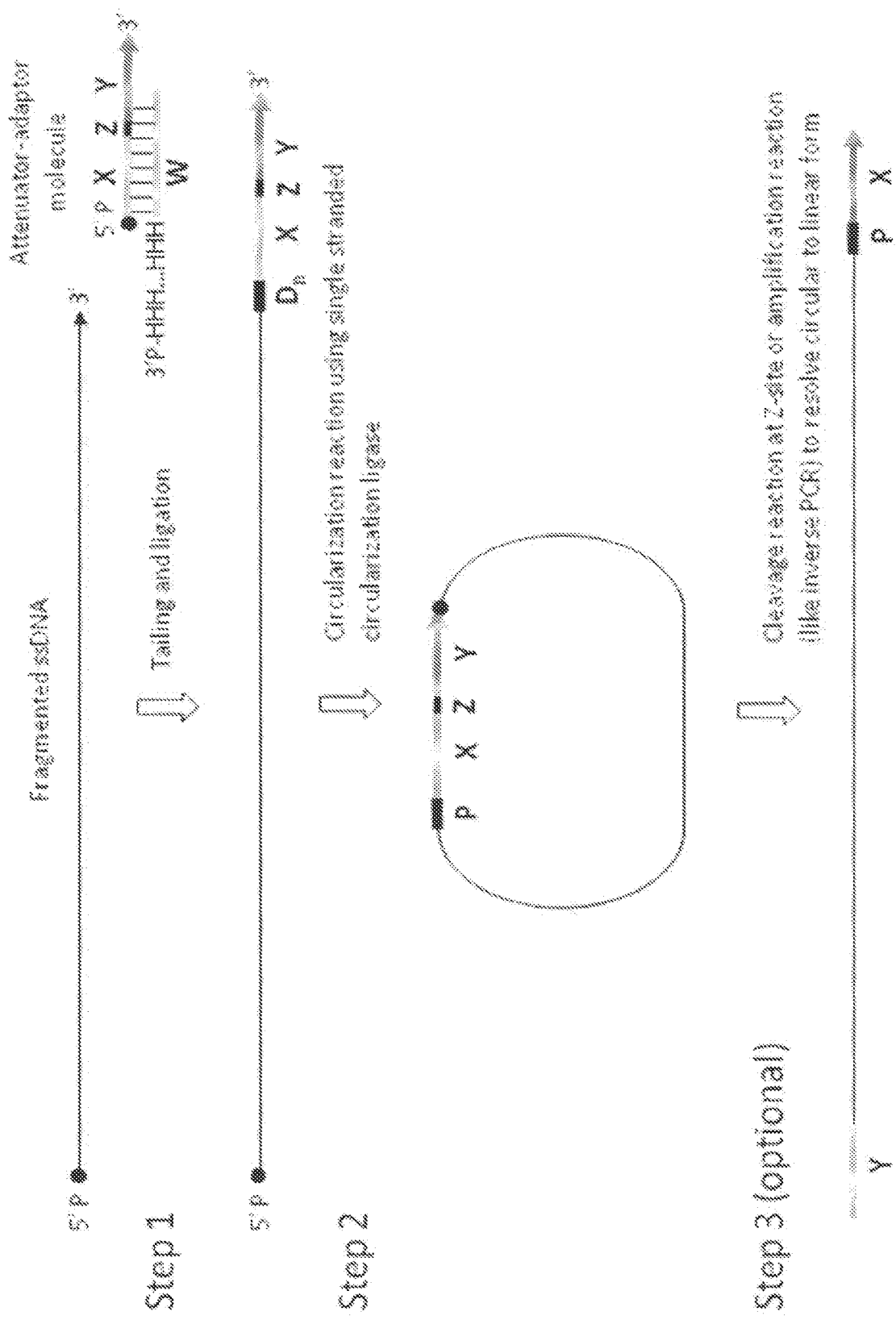
FIG. 25 depicts a method of NGS library synthesis using controlled homopolymer tailing and ligation followed by circularization of the substrate polynucleotide.
Figure 26:
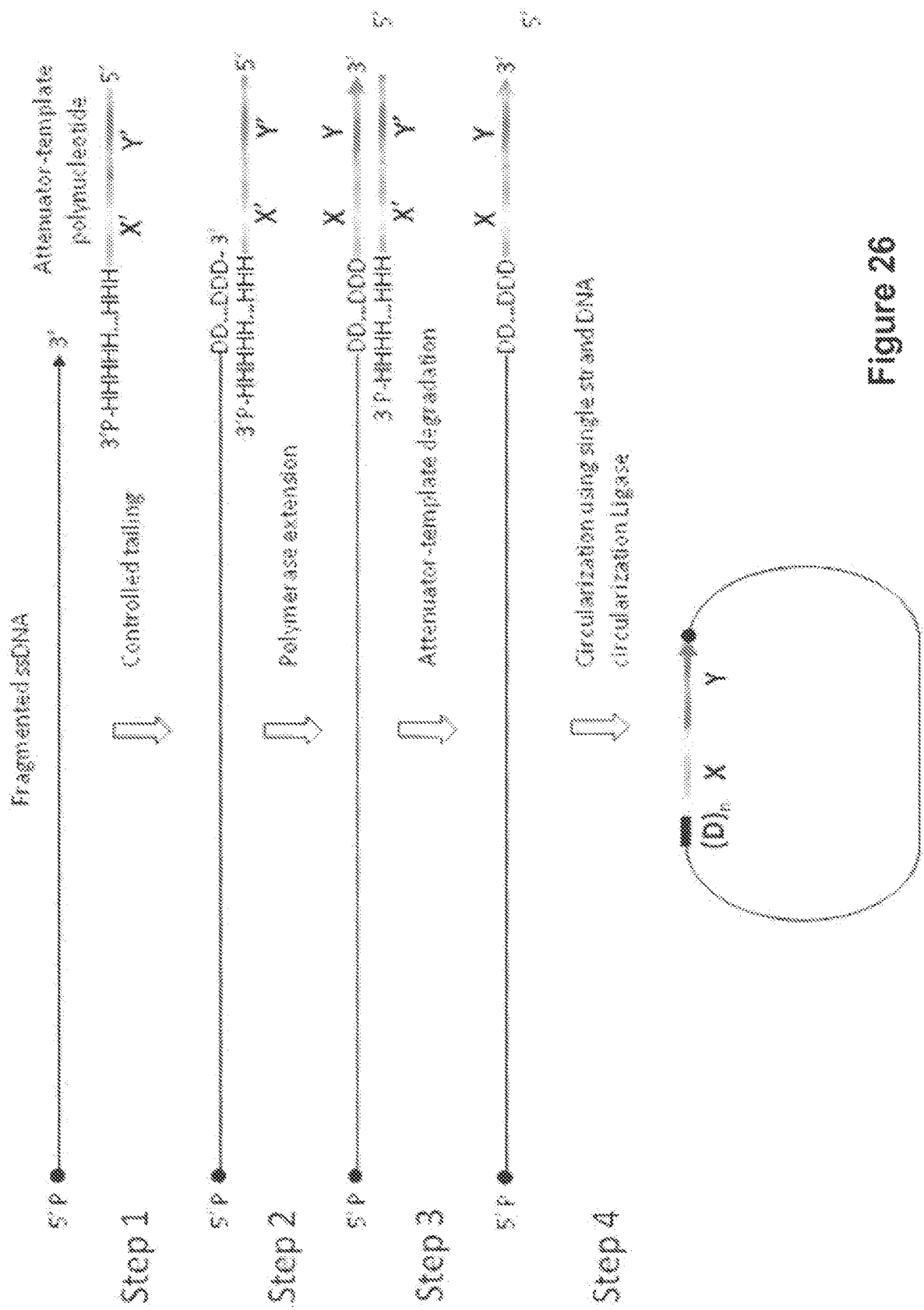
FIG. 26 shows an alternative method for NGS library synthesis using controlled homopolymer tailing followed by polymerase extension and circularization.
Figure 27:
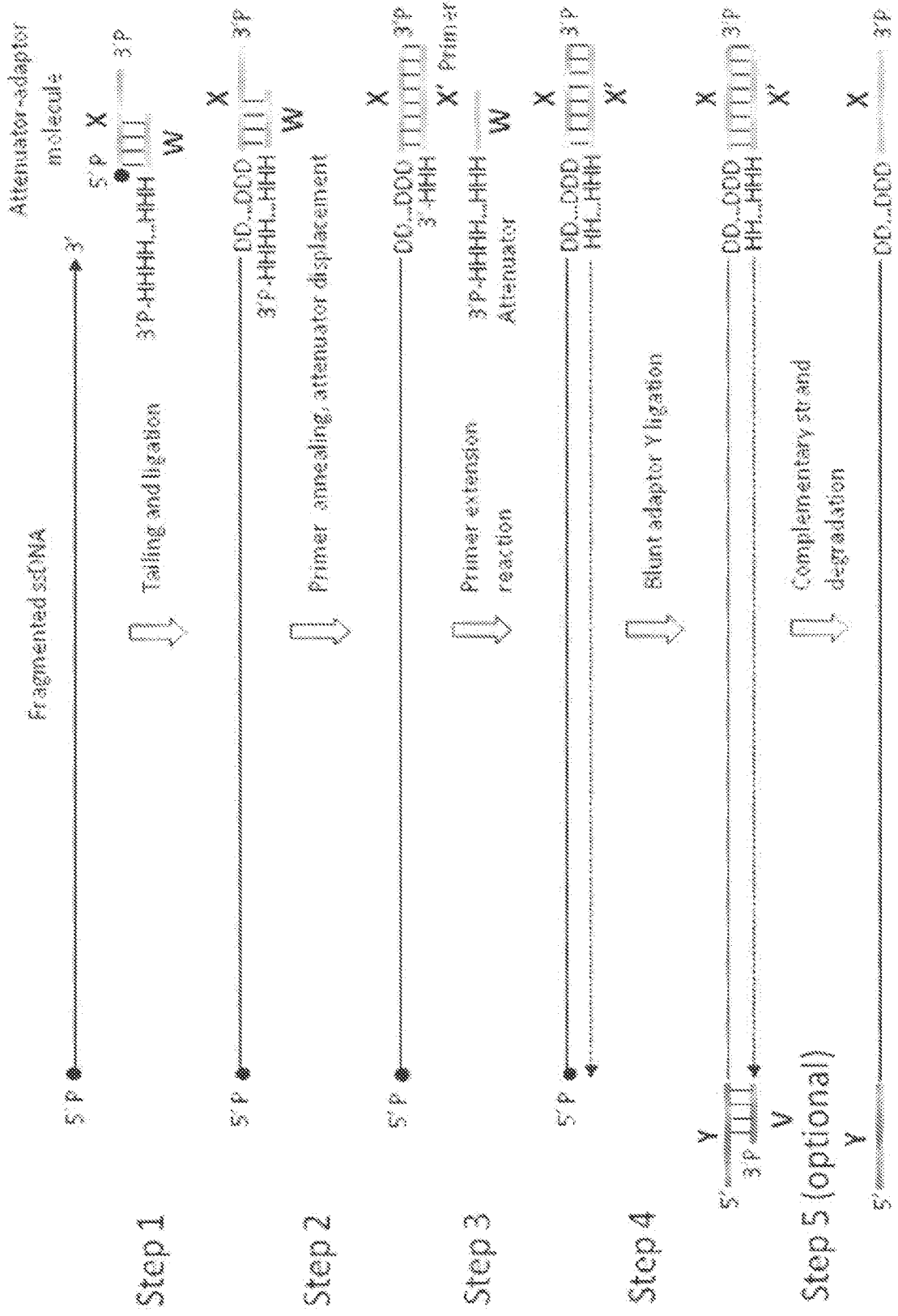
FIG. 27 depicts a method of NGS library synthesis using controlled homopolymer tailing and ligation followed by reverse strand synthesis and blunt adaptor ligation.
Figure 28:
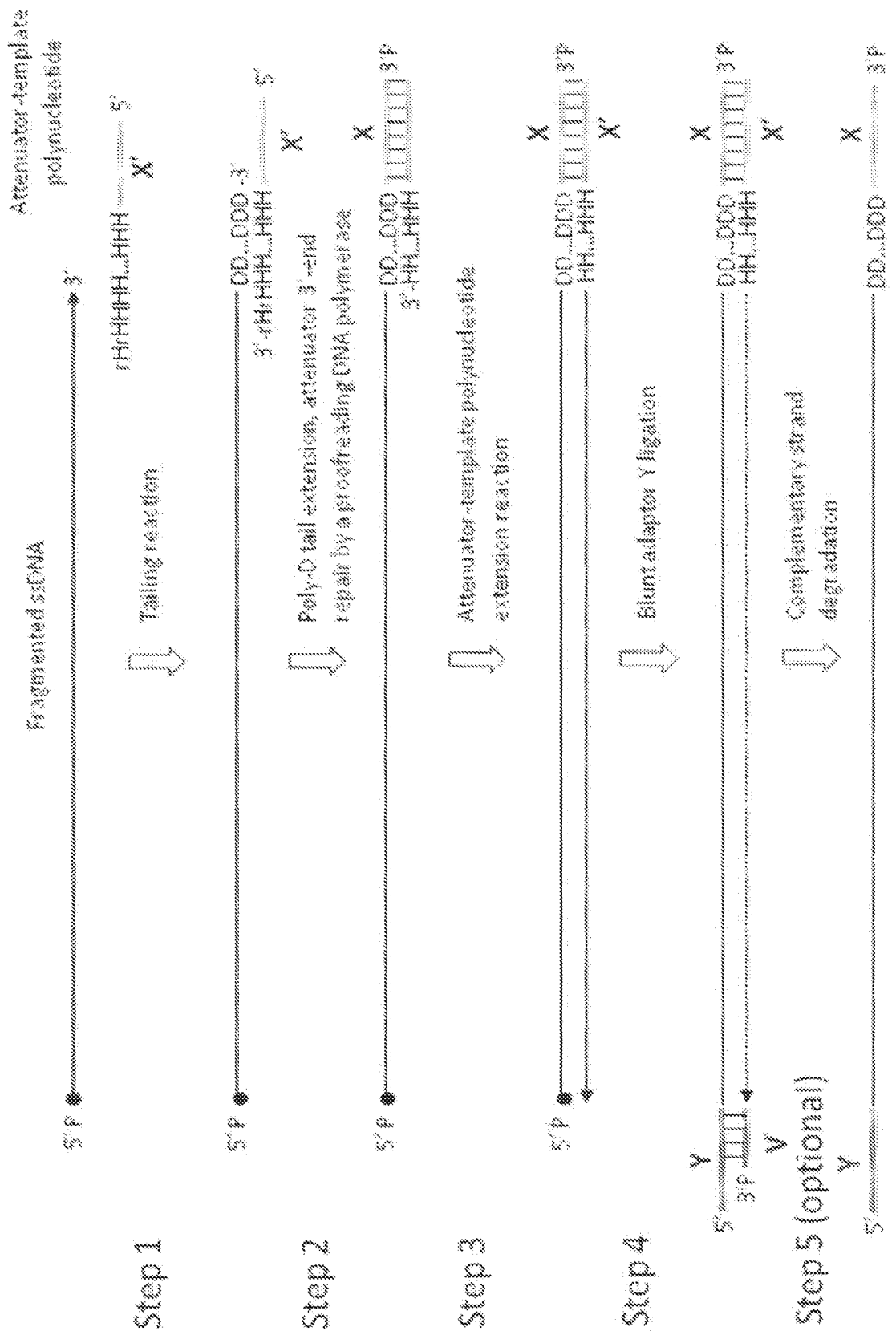
FIG. 28 shows an alternative method for NGS library construction comprising controlled tailing and polymerization followed by reverse strand synthesis and blunt ligation.
Figure 29:
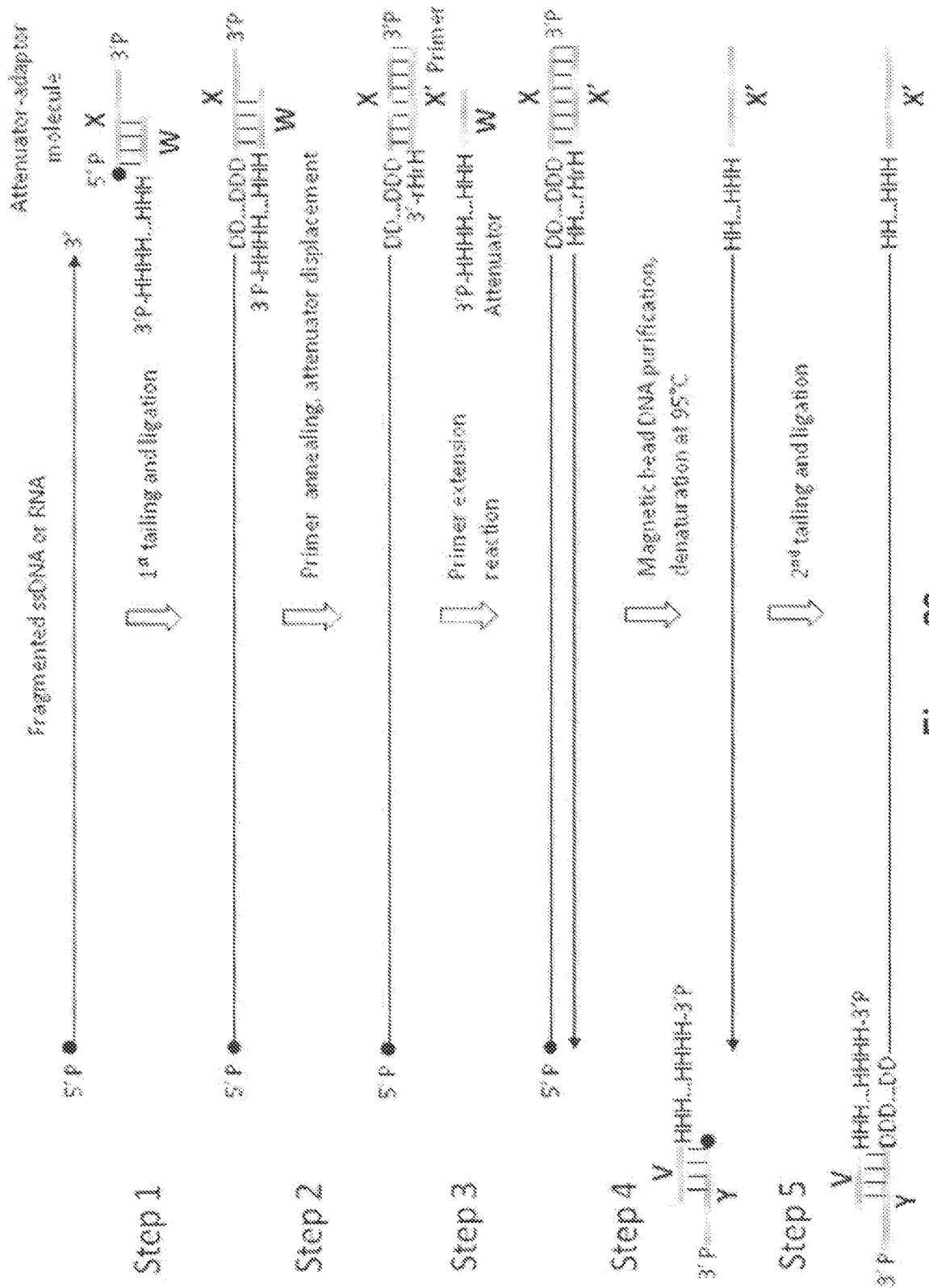
FIG. 29 depicts another method of NGS library preparation that comprises two sequential tailing and ligation reactions.
Figure 30:
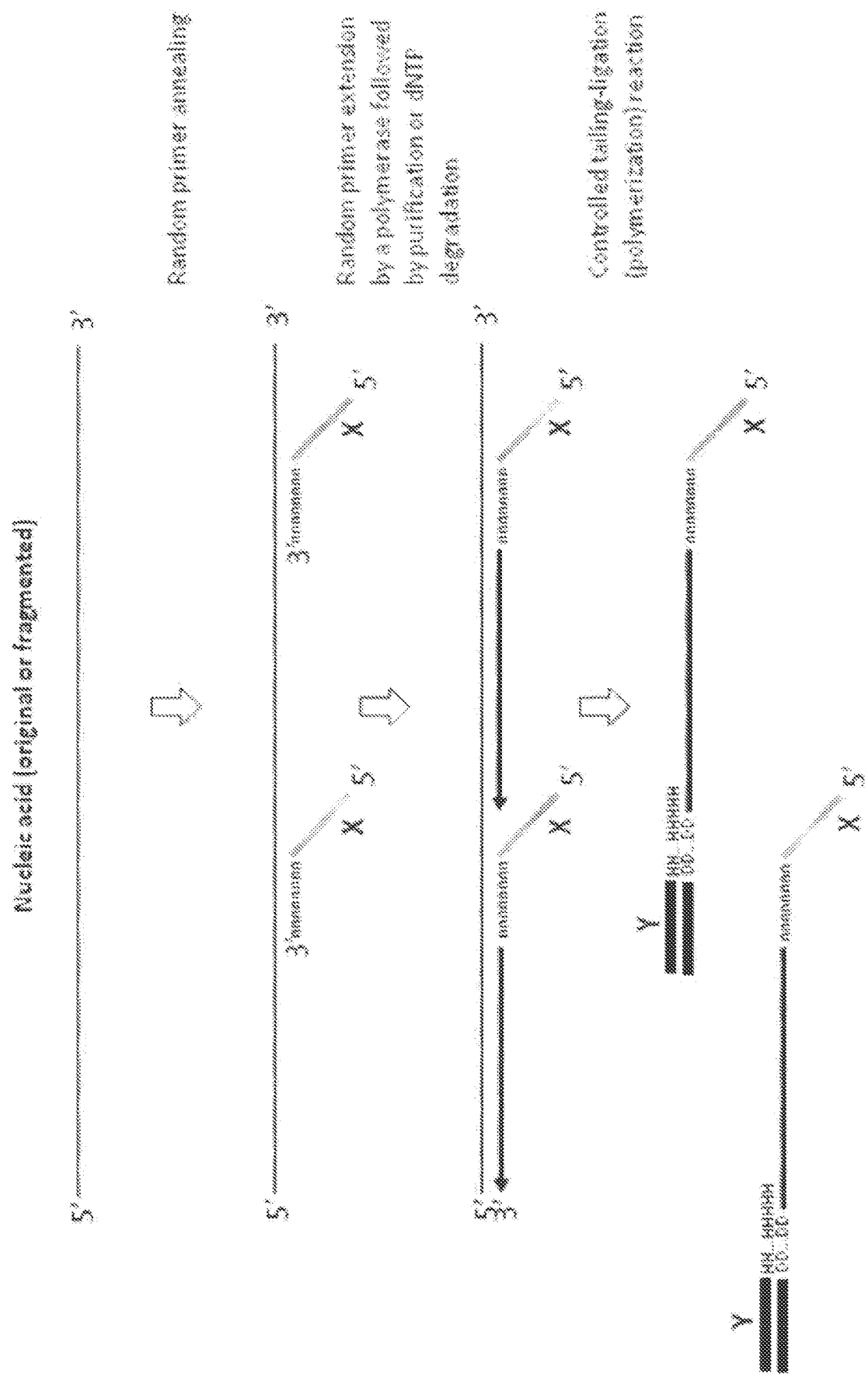
FIG. 30 is a schematic representation of the preparation of a fragment NGS library by random primer extension and controlled tailing and ligation of the extension products.
Figure 31:
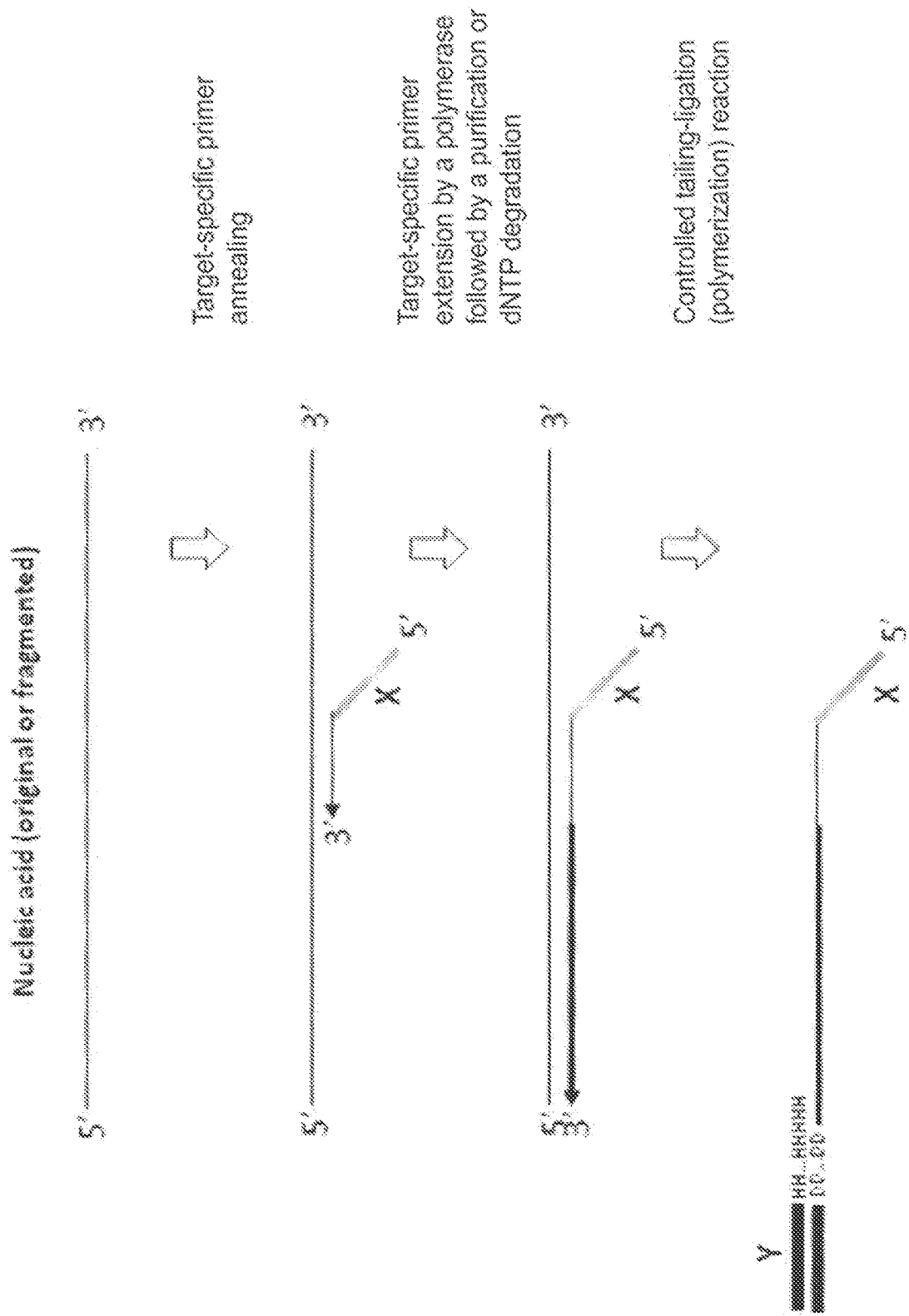
FIG. 31 is a schematic representation of the preparation of a targeted NGS library by target-specific primer extension and controlled tailing and ligation of the extension products.
Figure 32:
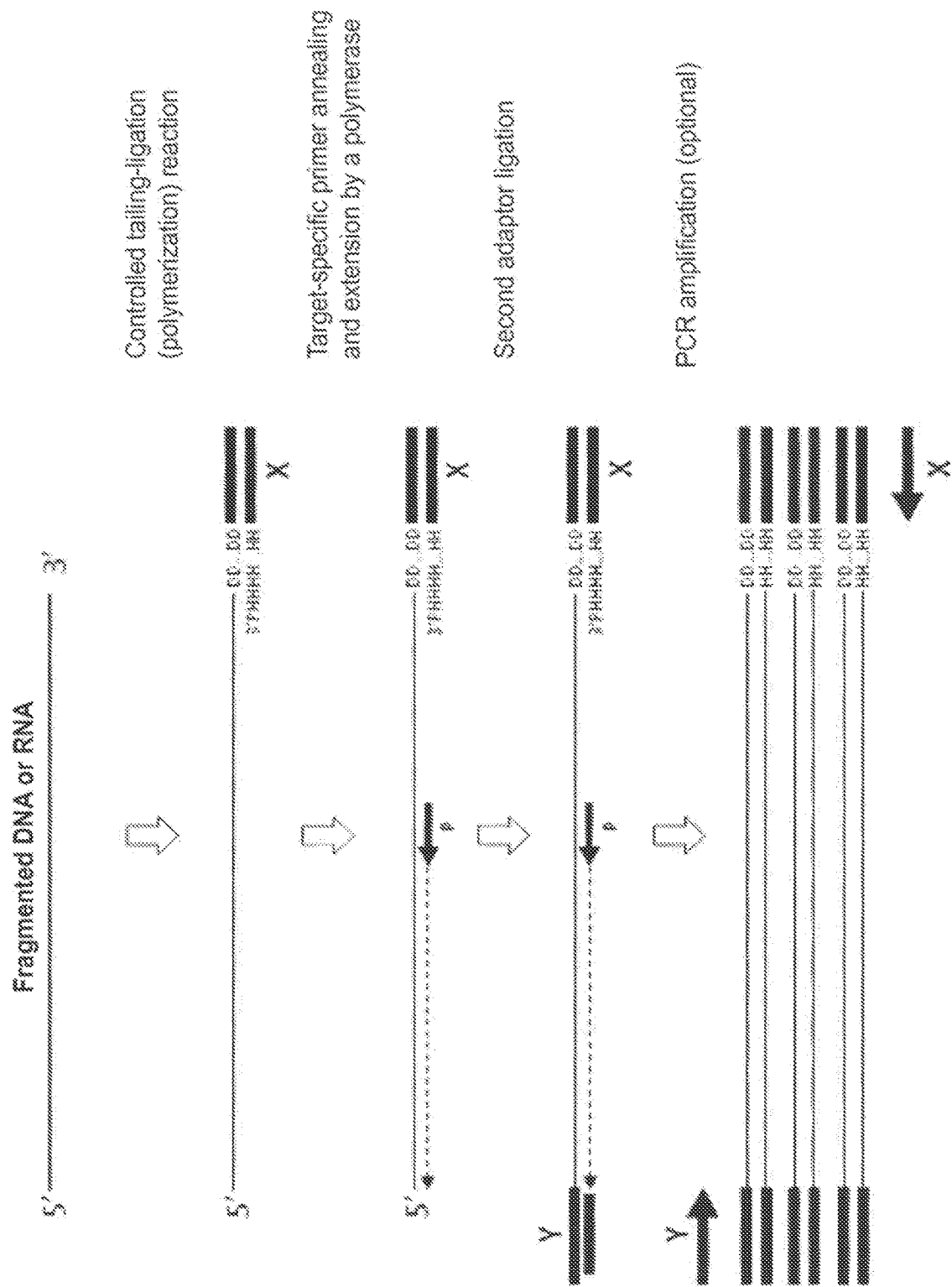
FIG. 32 is a schematic representation of the preparation of a targeted NGS library using a controlled tailing and ligation reaction followed by replication and adaptor ligation.
Figure 33:
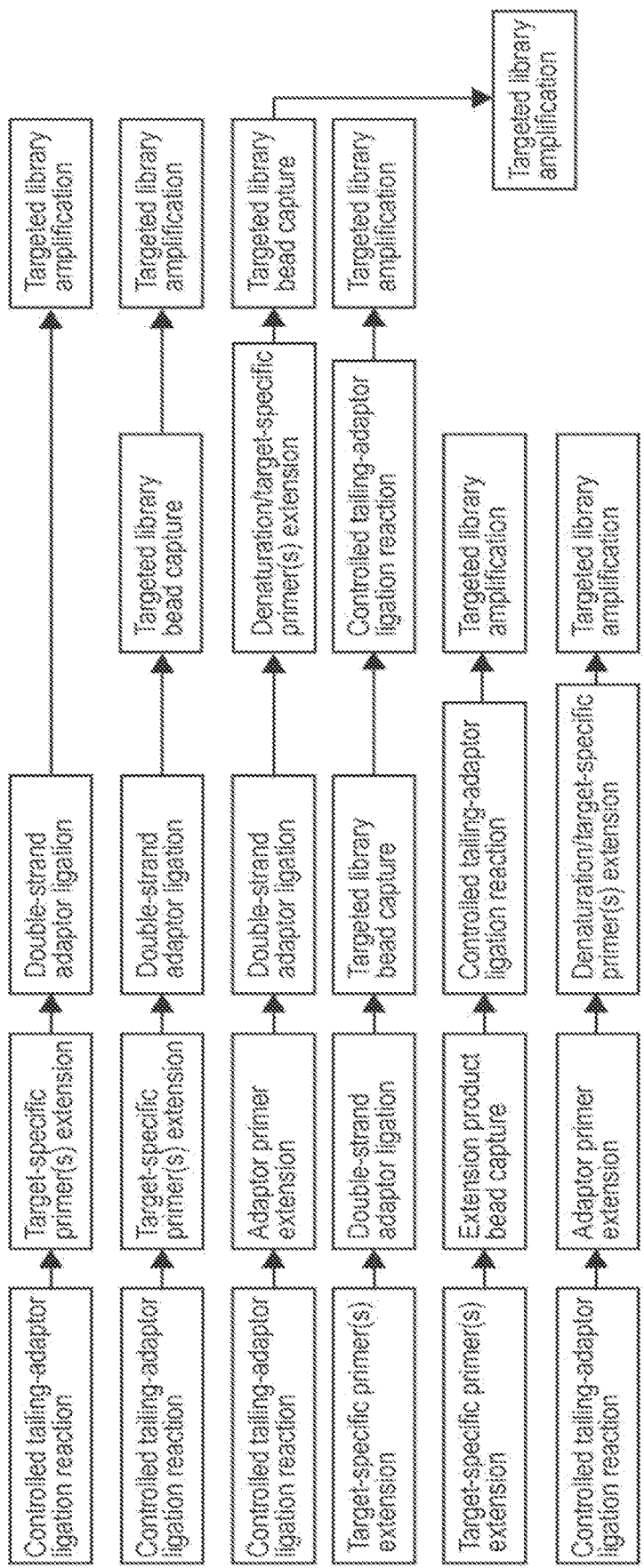
FIG. 33 is a schematic representation of various approaches for preparing a targeted NGS library using a controlled tailing-adaptor ligation reaction as contemplated by the disclosure.

Results: Electrophoretic analysis of products of simultaneously tailed and ligated substrate by Poly(A) polymerase and T4 DNA Ligase enzymes are shown in FIG. 23. Schematically the single-tube, single-step RNA tailing-ligation process is shown on FIG. 24c.

Conclusion: A synthetic RNA substrate can have a DNA adaptor sequence ligated to the 3' end of the RNA substrate by combined attenuated poly (rA)-tailing and ligation catalyzed by poly(A) polymerase and T4 DNA ligase. The reaction can be used for efficient adaptation and tagging of random single-stranded RNA molecules in a single-tube, single-reaction format.

TABLE 1

Synthetic polynucleotide substrates

| ID | SEQ ID NO | Sequence |
|---|---|---|
| 10-001: | 1 | 5'-GGT CGT AGC AGT CGT TGA TG-3' |
| 10-105: | 2 | 5'-TAG TTG CTG CAA CCT AGT CTA GAT CTA TAA ACG CAC CTT GGA CA CGG GG-3' |
| 10-106: | 3 | 5'-CCC CGT GTC CAA AGG TGC GTT TAT AGA TCT AGA TCT AGA CTA GGT TGC AGC AAC TA-3' Phosphate |
| 10-107: | 4 | 5'-TAG TTG CTG CAA CCT AGT CTA GAT CTA TAA ACG CAC CTT GGA CA CTT TT-3' |
| 10-108: | 5 | 5'-AAA AGT GTC CAA AGG TGC GTT TAT AGA TCT AGA CTA GGT TGC AGC AAC TA-3' Phosphate |
| 10-109: | 6 | 5'-CGT GTC CAA AGG TGC GTT TAT AGA TCT AGA TCT AGA TCT AGA CTA GGT TGC AGC AAC TA-3' Phosphate |
| 10-110: | 7 | 5'-GGT CCC CGT GTC CAA AGG TGC GTT TAT AGA TCT AGA TCT AGA TCT AGA CTA GGT TGC AGC AAC TA-3' Phosphate |
| 10-085: | 8 | 5'-GTA TCG CTA CGT TGT CAC ACA CTA CAC TGC TCG ACA GTA AAT ATG CCA AG-3' |
| 10-127: | 9 | 5'-GAT CGT AGC TAG $(N)_{11}$G-3' |
| 10-128: | 10 | 5'-GAT CGT AGC TAG $(N)_{11}$C-3' |
| 10-129: | 11 | 5'-GAT CGT AGC TAG $(N)_{11}$T-3' |
| 10-139: | 12 | 5'-GAT CGT AGC TAG $(N)_{11}$A-3' |
| 10-191: | 13 | 5'-rGrGrCrCrUrUrGrUrUrCrUrGrUrCrCrCrA-3' |

TABLE 2

Synthetic polynucleotide-attenuators

| ID | SEQ ID NO | Sequence |
|---|---|---|
| 10-103: | 14 | 5'-$(TTTTTU)_6$TTTT-3' Phosphate |
| 10-130: | 15 | 5'-GAT CGT AU $T_7$ rUrU-3' |
| 10-131: | 16 | 5'-GAT CGT AU $T_8$ rUrU-3' |
| 10-132: | 17 | 5'-GAT CGT AU $T_9$ rUrU-3' |
| 10-133: | 18 | 5'-GAT CGT AU $T_{10}$ rUrU-3' |
| 10-134: | 19 | 5'-GAT CGT AU $T_{11}$ rUrU-3' |
| 10-135: | 20 | 5'-GAT CGT AU $T_{12}$ rUrU-3' |
| 10-136: | 21 | 5'-$(AAA)_6$AA-3' Phosphate |
| 10-137: | 22 | 5'-$(CCC)_6$CC-3' Phosphate |
| 10-138: | 23 | 5'-$(GGG\ GGT)_6$GGG G-3' Phosphate |
| 10-192: | 24 | 5'-$(AAA)_{10}$A-3' Phosphate |
| 11-049 | 25 | 5'-$(rArArA)_{10}$-3' Phosphate |

TABLE 3

Synthetic polynucleotides comprising the attenuator-adaptor complex

| ID | SEQ ID NO | Sequence |
|---|---|---|
| 10-211 | 26 | 5' Biotin-TAC ACT CTT TCC CTA CAC GAC GCT CTT CCG ATC TTT TTT TTT TrUrU-3' |
| 10-212 | 27 | 5' Phosphate-GAT CGG AAG AGC GTC GTG TAG GGA AAG AGT GTA-3' Phosphate |
| 11-010 | 28 | 5' Phosphate-CTT ATT GCT GTG GTT GGT TCC TGT GCT GTT TT-3' Phosphate |
| 11-011 | 29 | 5'-CCAACCACAGCAAUAAGUTTTUTTTTUTT TTUTTTT-3' Phosphate |

TABLE 4

Synthetic polynucleotides comprising the DNA tailing size marker

| ID | SEQ ID NO | Sequence |
|---|---|---|
| 10-001 | 30 | 5'-GGT CGT AGC AGT CGT TGA TG-3' |
| 10-009 | 31 | 5'-GGT CGT AGC AGT CGT TGA TGA AAA A-3' |
| 10-100 | 32 | 5'-GGT CGT AGC AGT CGT TGA TGA AAA AAA-3' |
| 10-101 | 33 | 5'-GGT CGT AGC AGT CGT TGA TGA AAA AAA AAA AA-3' |
| 10-102 | 34 | 5'-GGT CGT AGC AGT CGT TGA TGA AAA AAA AAA AAA AAA A-3' |

TABLE 5

Double stranded DNA substrates

| ID | SEQ ID NO | Sequence |
|---|---|---|
| Blunt end, GC-Rich | | |
| 10-105 | 35 | 5'-TAG TTG CTG CAA CCT AGT CTA GAT CTA TAA ACG CAC CTT TGG ACA CGGGG-3' |
| 10-106 | 36 | 3P'-ATC AAC GAC GTT GGA TCA GAT CTA GAT ATT TGC GTG GAA ACC TGT GCC CC-5' |
| Blunt end AT-Rich | | |
| 10-107 | 37 | 5'-TAG TTG CTG CAA CCT AGT CTA GAT CTA TAA ACG CAC CTT TGG ACA CTT TT-3' |
| 10-108 | 38 | 3P'-ATC AAC GAC GTT GGA TCA GAT CTA GAT ATT TGC GTG GAA ACC TGT GAAAA-5' |
| 3'-Overhang End (3 bases) | | |
| 10-105 | 35 | 5'-TAG TTG CTG CAA CCT AGT CTA GAT CTA TAA ACG CAC CTT TGG ACA CGGGG-3' |
| 10-109 | 39 | 3P'-ATC AAC GAC GTT GGA TCA GAT CTA GAT ATT TGC GTG GAA ACC TGT GC-5' |
| 3'-Recessed End (3 bases) | | |
| 10-105 | 35 | 5'-TAG TTG CTG CAA CCT AGT CTA GAT CTA TAA ACG CAC CTT TGG ACA CGGGG-3' |
| 10-110 | 40 | 3P'-ATC AAC GAC GTT GGA TCA GAT CTA GAT ATT TGC GTG GAA ACC TGT GCC CCTGG-5' |
| Attenuator-adaptor | | |
| 10-212 | 41 | 5'P-GATCGGAAGAGCGTCGTGTAGGGAAAGAGTGTA-3'P |
| 10-211 | 42 | 3'-rUrUTTTTTTTTTTCTAGCC TTCT CGCAGCACATC C CTTTT CTCACAT - Biotin-5' |

The following Table 7 provides NGS Adaptor Sequences corresponding to NGS sequence X and sequence Y (see FIGS. 25-29).

| Adaptor | Sequence (5'-3') | SEQ ID NO |
|---|---|---|
| Ion Torrent Adaptor A | CCATCTCATCCCTGCGTGTCTCCGACTCAG | 44 |
| Ion Torrent P1 | CCACTACGCCTCCGCTTTCCTCTCTATGGGCAGTCGGTGAT | 45 |
| Illumina Adaptor 1 | P-GATCGGAAGAGCTCGTATGCCGTCTTCTGCTTG | 46 |
| Illumina Adaptor 2 | ACACTCTTTCCCTACACGACGCTCTTCCGATCT | 47 |
| Roche 454 Adaptor A | CCATCTCATCCCTGCGTGTCTCCGACTCAG | 48 |
| Roche 454 Adaptor B | CCTATCCCCTGTGTGCCTTGGCAGTCTCAG | 49 |
| SOLiD Adaptor P1 | CCACTACGCCTCCGCTTTCCTCTCTATGGGCAGTCGGTGAT | 50 |
| SOLiD Adaptor P2 | AGAGAATGAGGAACCCGGGGCAGTT | 51 |

Example 12

Controlled Tailing and Ligation Reaction with Attenuator-Adaptor Molecules

Materials:

10 μM Adaptor oligonucleotide 13-128 (Table X)
10 μM Attenuator-adaptor oligonucleotide 7N 13-281

TABLE 6

Structure of the Attenuator-Adaptor Complex

| ID | SEQ ID NO | Structure |
|---|---|---|
| 10-212 | 41 | 5'P-GATCGGAAGAGCGTCGTGTAGGGAAAGAGTGTA-3'P |
| 10-211 | 42 | 3'-rUrUTTTTTTTTTTCTAGCCTTCTCGCAGCACATCCTTTCTCACAT-Biotin-5' |

12b-attenuator domain / 33b-adaptor domain

| 11-010 | 28 | 5'P-CTTATTGCTGTGGTTGGTTCCTGTGCTGTTTT-3'P |
| 11-011 | 29 | 3'P-TTTTUTTTTUTTTTUTTTUGAAUAACGACACCAACC-5' |

19b-attenuator domain / 32b-adaptor domain

-continued

10 µM Attenuator-adaptor oligonucleotide 6N 13-280
10 µM Attenuator-adaptor oligonucleotide 5N 13-279
10 µM Attenuator-adaptor oligonucleotide 3N 13-278
Substrate oligonucleotide 12-492
T4 DNA ligase (Rapid) 600,000 U/ml (Enzymatics, Cat# L6030-HC-L)
Terminal deoxynucleotidyl transferase 20,000 U/ml (Enzymatics, Cat# P7070L)
10 × Green Buffer (Enzymatics, Cat# B1020)
Adenosine 5'-Triphosphate (ATP) 10 mM (New England BioLabs, Cat# P0756S)
100 mM dATP Set (Life technologies, Invitrogen, Cat# 10216-018)
25 bp ladder DNA size marker (Life technologies, Invitrogen, Cat# 10488-022)

Method:

A controlled tailing and ligation reaction was assembled in this order in a total volume of 40 µl at a final concentration of 0.25 µM of Substrate oligonucleotide 12-492, 0.75 µM Adaptor oligonucleotide 13-128, 1.5 µM Attenuator-adaptor oligonucleotide 13-281 or 1.5 µM Attenuator-adaptor oligonucleotide 13-280 or 1.5 µM Attenuator-adaptor oligonucleotide 13-279 or 1.5 µM Attenuator-adaptor oligonucleotide 13-278 or a combination of these four with 0.375 µM of each, or 0.750 µM of each, or 1.125 µM of each, 1× Green Buffer, 1 mM ATP, 1 mM dATP, 15 U/[µl T4 DNA ligase and 0.5 U/µl Terminal deoxynucleotidyl transferase.

The reaction was incubated at 25° C. for 10 minutes, 95° C. for 2 minutes. Next, 10[il of the sample were boiled with 2× formamide loading buffer and subsequently run on a pre-casted 15% polyacrylamide gel, TBE-Urea (Invitrogen, Cat #S11494), stained SYBR® Gold nucleic acid gel stain (Invitrogen, Cat #S11494), visualized on a Dark reader light box (Clare Chemical Research) and photographed using a digital camera.

Figure 34:
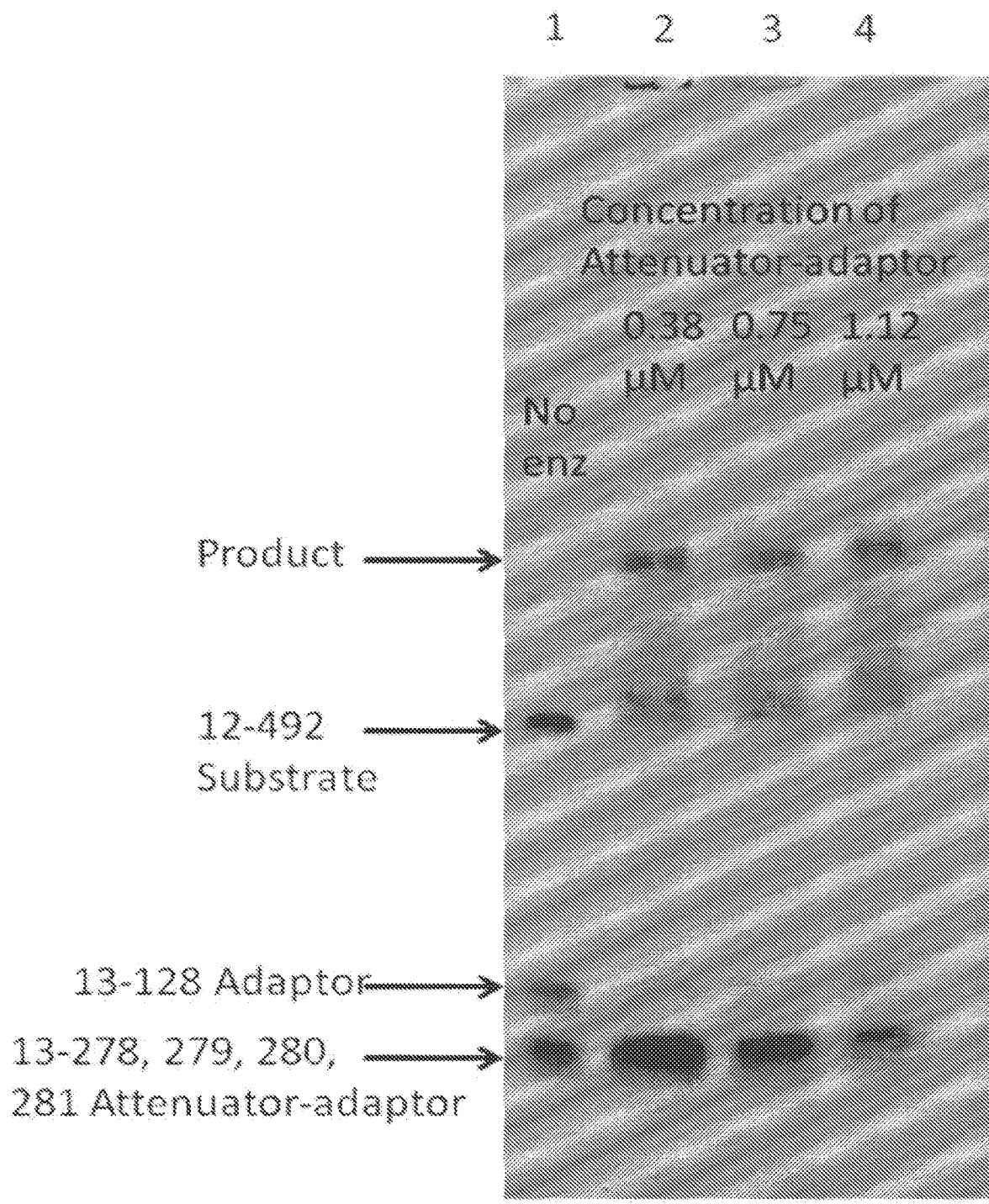
FIG. 34 shows experimental data regarding Example 12, gel 1, which is a controlled tailing and ligation reaction with attenuator-adaptor molecules that comprise an additional 3' domain of random base composition.
Figure 35:
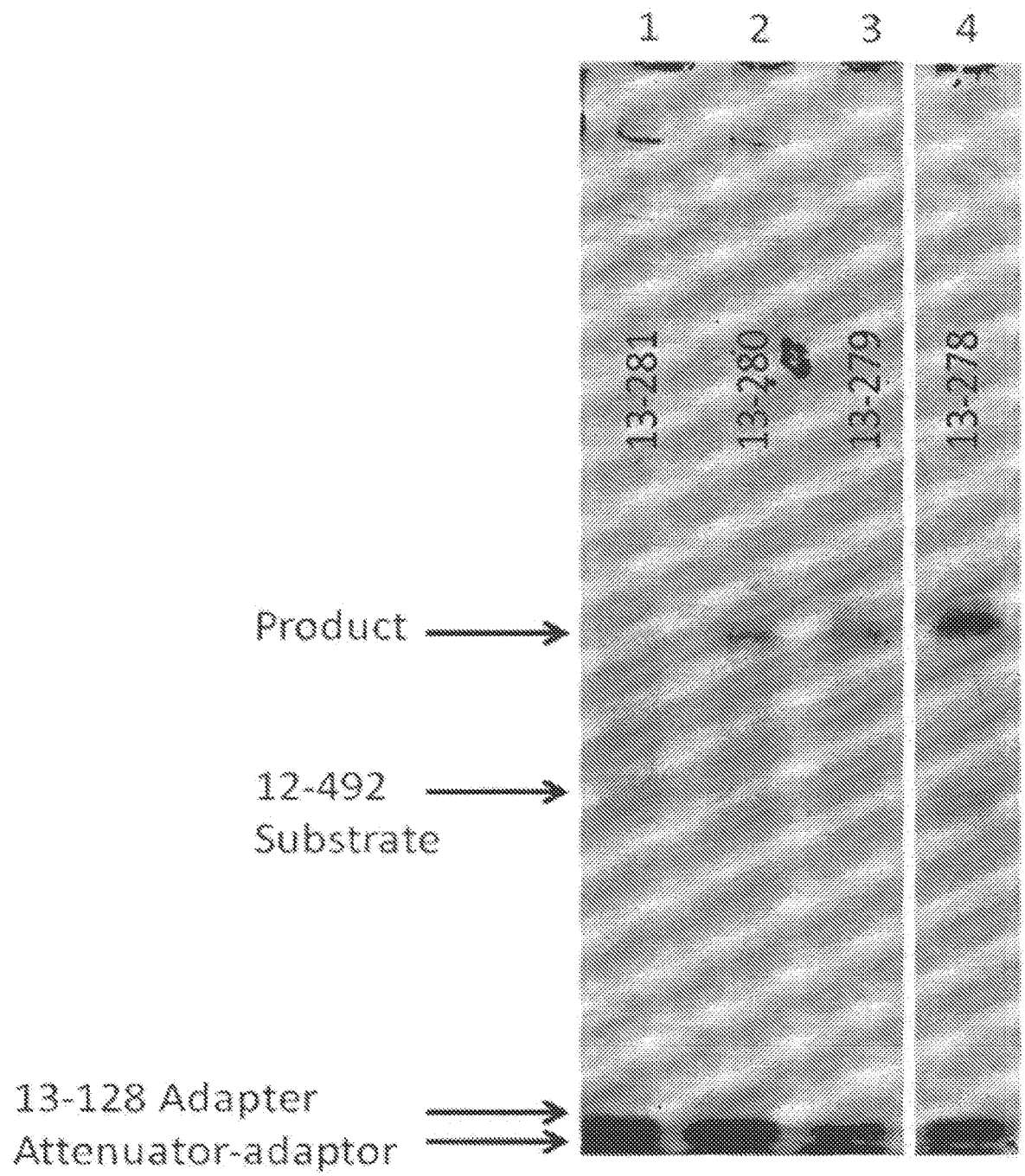
FIG. 35 shows experimental data regarding Example 12, gel 2, which is a controlled tailing and ligation reaction with attenuator-adaptor molecules that comprise an additional 3' domain of random base composition.

Results:

Controlled tailing and ligation reactions were performed and visualized on a 15% polyacrylamide gel by electrophoresis under denaturing conditions. Gel 1 lane 1 contains only oligonucleotides. Gel 1 lane 2, 3, and 4 show a band representing the product of addition of the homopolymer (approximately 2-6 base pairs) and ligation of the adaptor (23 base pairs) to the substrate (43 base pairs) (FIG. 34). Gel 2 lane 1, 2, 3, and 4 shows a band representing the product of addition of the homopolymer (approximately 2-6 base pairs) and ligation of the adaptor (23 base pairs) to the substrate (43 base pairs) (FIG. 35). Bands corresponding to the product of addition of a homopolymer tail and ligation to the target substrate are observed in the presence of the random base attenuator-adaptors 13-278, 13-279, 13-280, 13-281, and an equimolar combination of all four random base attenuator-adaptors.

Conclusion:

The addition of a homopolymer tail and ligation to the target substrate was accomplished with random base attenuator-adaptors 13-278, 13-279, 13-280, and 13-281 to varying efficiencies.

Example 13

Controlled Tailing and Ligation Reaction with Dinucleotide Attenuator-Adaptors

Materials:

Substrate oligonucleotide (12-492)
Adaptor oligonucleotide (13-128)
Attenuator-adaptor oligonucleotide 12T (13-114)
Attenuator-adaptor oligonucleotide 6C (13-263)
Attenuator-adaptor oligonucleotide 6K (13-274) where K corresponds to G/T dinucleotide
Attenuator-adaptor oligonucleotide 6R (13-275) where R corresponds to G/A dinucleotide
T4 DNA ligase (Rapid) 600,000 U/ml (Enzymatics, Cat# L6030-HC-L)
Terminal deoxynucleotidyl transferase 20,000 U/ml (Enzymatics, Cat# P7070L)
10 × Green Buffer (Enzymatics, Cat# B1020)
Adenosine 5'-Triphosphate (ATP) 10 mM (New England BioLabs, Cat# P0756S)
100 mM deoxyribonucleoside triphosphates (dNTP) Set (Life technologies, Invitrogen, Cat# 10297-117)
25 bp ladder DNA size marker (Life technologies, Invitrogen, Cat# 10488-022)

Method:

A controlled tailing and ligation reaction was assembled in this order in a total volume of 40 µl at a final concentration of 0.25 µM of Substrate oligonucleotide 13-325, 0.75 µM Adaptor oligonucleotide 13-128, 1.5 µM Attenuator-adaptor oligonucleotides with attenuator portions corresponding to 12T or 6C homopolymers or a plurality of 6R (G/A) or 6K (G/T) randomly synthesized dinucleotides, 1× Green Buffer, 0.5 mM, 1 mM ATP, 1 mM of appropriate dNTP mononucleotide or dinucleotide mixture complementary to the mononucleotide or dinucleotide attenuator-adaptor used (see gel label), 15 U/µl T4 DNA ligase and 0.5 U/µl Terminal deoxynucleotidyl transferase.

The reaction was incubated at 25° C. for 30 minutes, followed by incubation at 95° C. for 2 minutes. Next, 10 µl of the sample were boiled with formamide loading buffer 2× and subsequently run on a pre-casted 15% polyacrylamide gel, TBE-Urea (Invitrogen, Cat #S11494), stained SYBR® Gold nucleic acid gel stain (Invitrogen, Cat #S11494), visualized on a Dark reader light box (Clare Chemical Research) and photographed using a digital camera.

Figure 36:
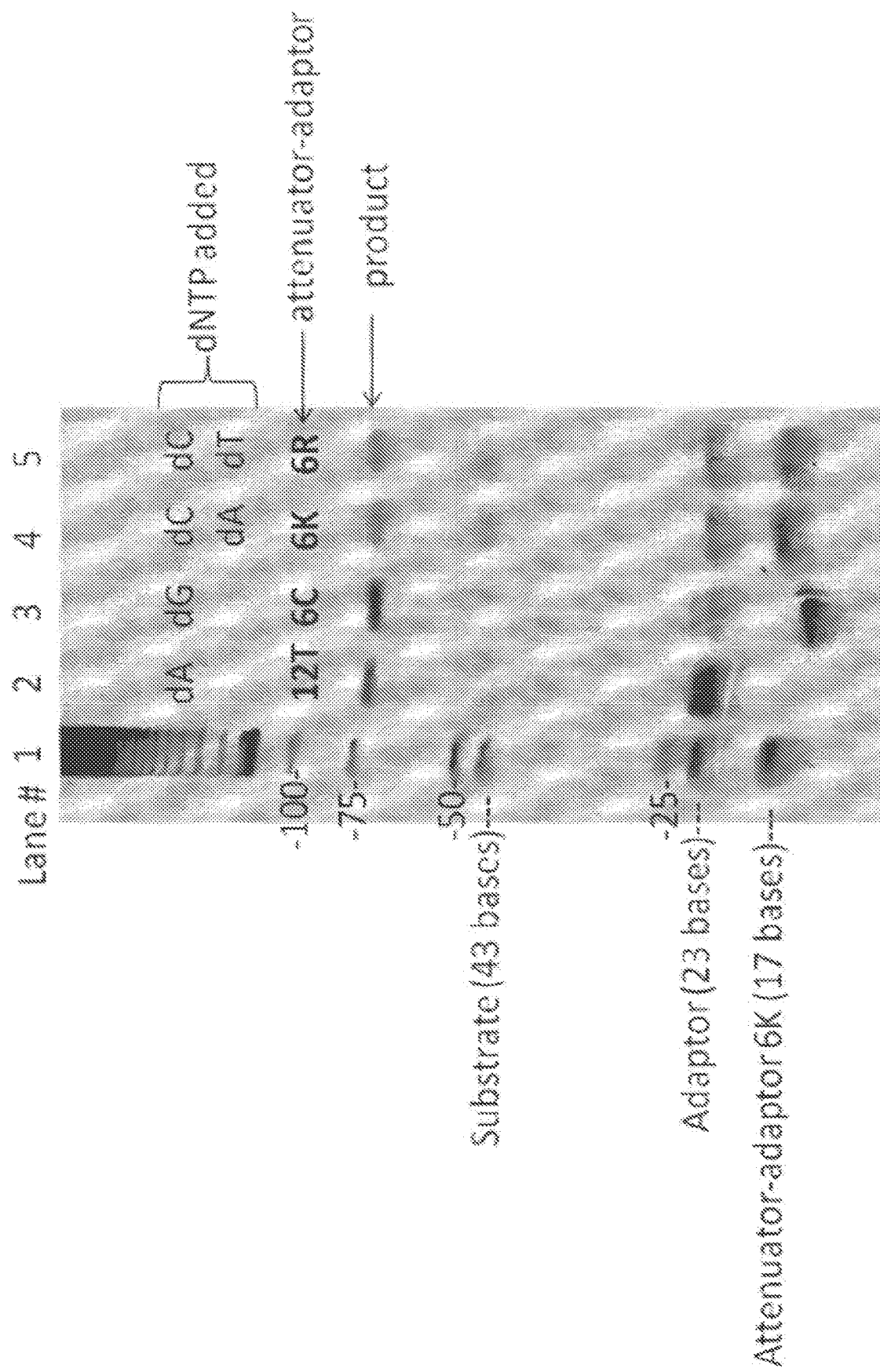
FIG. 36 shows experimental data regarding a controlled tailing and ligation reaction with dinucleotide attenuator-adaptors.
Figure 37:
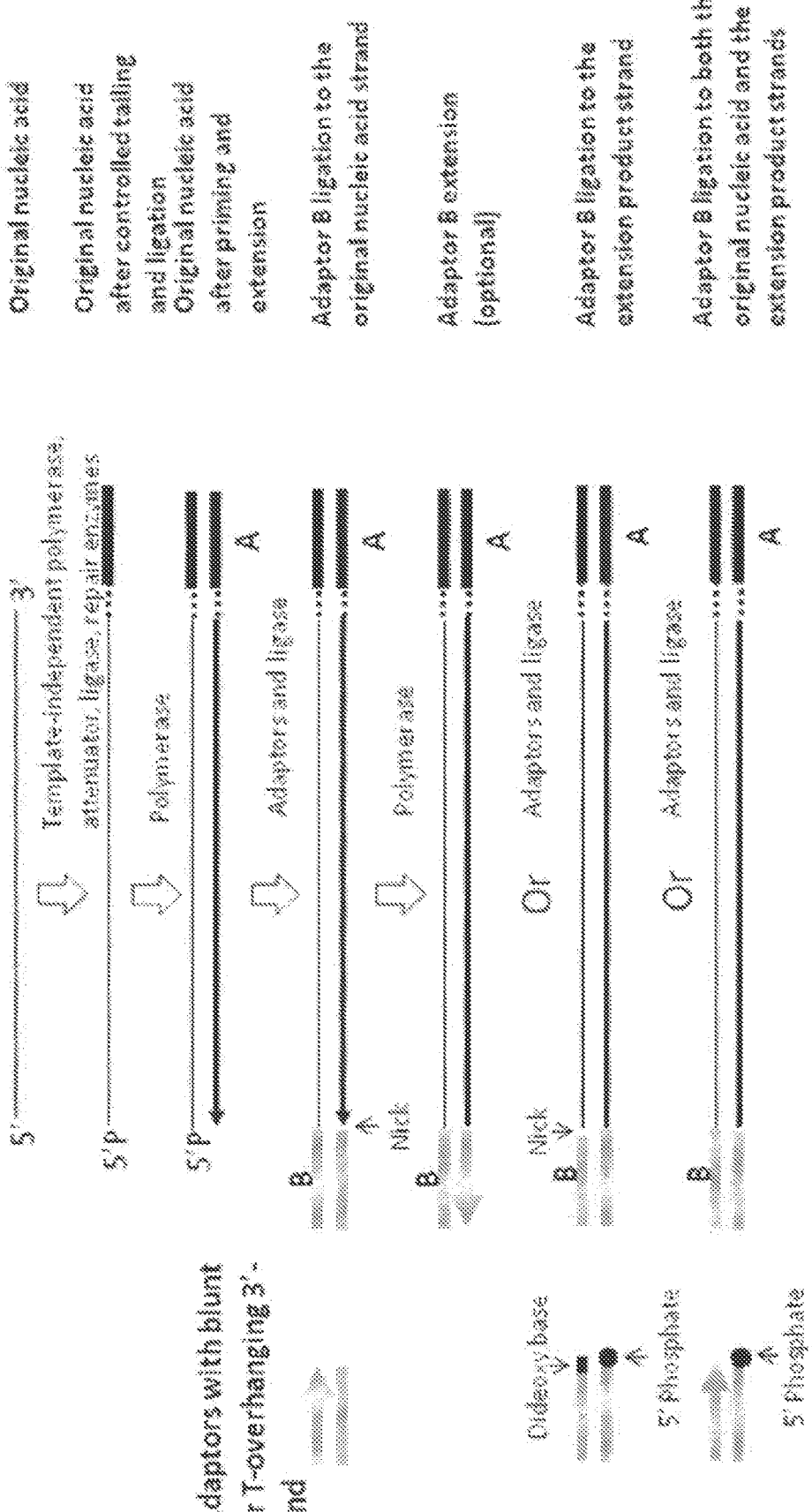
FIG. 37 depicts various methods of blunt or TA adaptor ligation as part of a whole genome or targeted library preparation.

Results:

Controlled tailing and ligation reactions were performed and visualized on a 15% polyacrylamide gel by electrophoresis under denaturing conditions. Lanes 2, 3, 4 and 5 show the tailed and ligated product just below 75 base marker, corresponding to the ligation of the 23 bases adaptor (13-128) to the 43 bases substrate (12-492) which was tailed by the TdT enzyme (approximately 6 bases) for a product size about 72 bases. Adaptor (13-128) and attenuator¬adaptor excess are also observed. Some leftover product is also observed at 43 bases in lane 2, 4 and 5. Lane 1 corresponds to the DNA polynucleotide marker spiked with Substrate oligonucleotide (12-492), Adaptor oligonucleotide (13-128) and Attenuator-adaptor oligonucleotide 6K (13-274) (FIG. 36).

Conclusions:

Controlled tailing and ligation reactions are efficient using dinucleotide tailing with the corresponding complementary plurality of random based dinucleotide attenuator-adaptors.

TABLE 8

Synthetic polynucleotide substrate for Examples 12 and 13

| ID | SEQ ID NO | Sequence |
|---|---|---|
| 12-492 | 52 | /5PHOS/NNNNNNNNNNNTGCCTCCTGGACTATGTCCGGGTANNNNNNNNNN |

TABLE 9

Synthetic polynucleotide attenuator-adaptors for Examples 12 and 13

| ID | SEQ ID NO | Sequence |
|---|---|---|
| 13-281 | 53 | CAGTCGGUGATTNNNNNNN/3SpC3/ |
| 13-280 | 54 | CAGTCGGUGATTTNNNNNN/3SpC3/ |
| 13-279 | 55 | CAGTCGGUGATTTTNNNNN/3SpC3/ |

TABLE 9-continued

Synthetic polynucleotide attenuator-adaptors for Examples 12 and 13

| ID | SEQ ID NO | Sequence |
|---|---|---|
| 13-278 | 56 | CAGTCGGUGATTTTTNNNN/3SpC3/ |
| 13-114 | 57 | CAGTCGGTGAUTTTTTUTTTTTT/3SpC3/ |
| 13-263 | 58 | CAGTCGGUGATCCCCCC/3SpC3/ |
| 13-274 | 59 | CAGTCGGUGATKKKKKK/3SpC3/ |
| 13-275 | 60 | CAGTCGGUGATRRRRRR/3SpC3/ |

TABLE 10

Synthetic polynucleotides comprising the adaptor for Examples 12 and 13.

| ID | SEQ ID NO | Sequence |
|---|---|---|
| 13-128 | 61 | /5Phos/ATCACCGACTGCCCATAGAGAGG/3Phos/ |

The invention claimed is:

1. A kit comprising
a template-independent nucleic acid polymerase;
an attenuator polynucleotide comprising an attenuator sequence and a sequence W positioned adjacent to the attenuator sequence, wherein the attenuator sequence is from about 10 nucleotides to about 100 nucleotides in length, and wherein the attenuator polynucleotide comprises a 3' blocking group;
an adaptor polynucleotide, wherein the adaptor polynucleotide comprises a sequence X which is complementary to sequence W of the attenuator polynucleotide;
nucleotides complementary to the attenuator sequence; and
a ligase.

2. The kit of claim 1, wherein the sequence W is positioned 5' adjacent to the attenuator sequence.

3. The kit of claim 1, wherein the template-independent nucleic acid polymerase is terminal deoxynucleotidyl transferase (TdT).

4. The kit of claim 1, wherein the template-independent nucleic acid polymerase is an RNA-specific nucleotidyl transferase selected from the group consisting of poly(A) polymerase and poly(U) polymerase.

5. The kit of claim 1, wherein the adaptor polynucleotide further comprises a 5' phosphate.

6. The kit of claim 1, further comprising a primer, a polymerase, and a second adaptor polynucleotide comprising a sequence Y and a sequence V, wherein sequence V is complementary to sequence Y when sequence V is the same length as sequence Y, or wherein sequence V is complementary to a portion of sequence Y when sequence V is less than the length of sequence Y, the second adaptor polynucleotide being a separate molecule from the attenuator polynucleotide.

7. The kit of claim 1, wherein the attenuator polynucleotide comprises an affinity label for immobilization.

8. The kit of claim 1, wherein the attenuator sequence of the attenuator polynucleotide comprises a homopolymeric sequence selected from the group consisting of poly (dA), poly (dT), poly (dC), poly (dG), and poly (dU).

9. The kit of claim 1, wherein the attenuator sequence of the attenuator polynucleotide comprises a homopolymeric sequence selected from the group consisting of poly (rA), poly (U), poly (rC), and poly (rG).

10. The kit of claim 1, wherein the attenuator sequence of the attenuator polynucleotide comprises a heteropolymeric sequence selected from the group consisting of (i) dA and rA bases, (ii) dT, dU and U bases, (iii) dC and rC bases, and (iv) dG and rG bases.

11. The kit of claim 1, wherein the attenuator sequence of the attenuator polynucleotide comprises a dinucleotide sequence comprising a plurality of random sequences comprised of the following dinucleotide combinations: (i) dG and dC; (ii) dA and dT; (iii) dG and dT; (iv) dG and dA; (v) dA and dC; or (vi) dC and dT.

12. The kit of claim 1, wherein the template-independent nucleic acid polymerase is terminal deoxynucleotidyl transferase (TdT), wherein the ligase is T4 DNA ligase, and wherein the 3' blocking group comprises a C3 spacer.

13. The kit of claim 1, wherein the attenuator sequence is from about 10 nucleotides to about 20 nucleotides in length.

* * * * *